United States Patent
Fujimura et al.

(10) Patent No.: US 9,029,541 B2
(45) Date of Patent: May 12, 2015

(54) BINUCLEAR METAL COMPLEX, AND ORGANIC ELECTROLUMINESCENCE ELEMENT COMPRISING SAME

(75) Inventors: Osamu Fujimura, Ube (JP); Kenji Fukunaga, Ichihara (JP); Takafumi Iwasa, Ichihara (JP); Yasuhiro Tanaka, Ichihara (JP); Harunori Fujita, Ichihara (JP); Tadashi Murakami, Ichihara (JP); Takashi Honma, Ichihara (JP); Toshikazu Machida, Ichihara (JP); Natsuko Kashihara, Ichihara (JP)

(73) Assignee: Ube Industries, Ltd., Ube-shi (JP)

( * ) Notice: Subject to any disclaimer, the term of this patent is extended or adjusted under 35 U.S.C. 154(b) by 0 days.

(21) Appl. No.: 13/990,928

(22) PCT Filed: Dec. 2, 2011

(86) PCT No.: PCT/JP2011/077979
§ 371 (c)(1),
(2), (4) Date: Aug. 13, 2013

(87) PCT Pub. No.: WO2012/074111
PCT Pub. Date: Jun. 7, 2012

(65) Prior Publication Data
US 2013/0324733 A1    Dec. 5, 2013

(30) Foreign Application Priority Data

Dec. 2, 2010  (JP) .................................. 2010-269627
Feb. 15, 2011 (JP) .................................. 2011-029564

(51) Int. Cl.
*H01L 51/00*    (2006.01)
*H05B 33/14*    (2006.01)
*C09K 11/06*    (2006.01)
*C07F 15/00*    (2006.01)

(52) U.S. Cl.
CPC .............. *H01L 51/009* (2013.01); *C09K 11/06* (2013.01); *C09K 2211/1029* (2013.01); *C09K 2211/1044* (2013.01); *C09K 2211/185* (2013.01); *H01L 51/0085* (2013.01); *H05B 33/14* (2013.01); *C07F 15/0033* (2013.01)

(58) Field of Classification Search
USPC ................................................ 546/4; 548/108
See application file for complete search history.

(56) References Cited

U.S. PATENT DOCUMENTS 7,825,250 B2 *  11/2010  Kakuta et al. .................... 546/10
8,633,380 B2 *   1/2014  Kakita et al. .................. 136/263
2003/0152802 A1  8/2003  Tsuboyama et al.
(Continued)

FOREIGN PATENT DOCUMENTS

JP   A-2003-73388   3/2003
JP   B-4310077      8/2009
(Continued)

OTHER PUBLICATIONS

Atwood; Inorganic Chemistry, 1984, 23, 4050-4057.*
(Continued)

*Primary Examiner* — John Mabry
*Assistant Examiner* — Daniel Carcanague
(74) *Attorney, Agent, or Firm* — Knobbe Martens Olson & Bear LLP

(57) ABSTRACT

A novel binuclear metal complex containing a biimidazole as a bridging ligand. The binuclear metal complex can be used as a material for an organic electroluminescence element.

5 Claims, 1 Drawing Sheet

(56) References Cited

U.S. PATENT DOCUMENTS

| | | | |
|---|---|---|---|
| 2006/0258043 A1 | 11/2006 | Bold et al. | |
| 2008/0015356 A1* | 1/2008 | Kakuta et al. | 546/10 |
| 2010/0006805 A1* | 1/2010 | Iwasa et al. | 252/501.1 |
| 2011/0100467 A1* | 5/2011 | Kakita et al. | 136/263 |
| 2011/0214740 A1* | 9/2011 | Aoki et al. | 136/263 |
| 2012/0204959 A1* | 8/2012 | Kakita et al. | 136/263 |

FOREIGN PATENT DOCUMENTS

| | | | |
|---|---|---|---|
| WO | WO 01/08230 A1 | | 2/2001 |
| WO | WO 2005/019373 A2 | | 3/2005 |
| WO | WO 2009154275 | * | 12/2009 |
| WO | WO 2010055856 | * | 5/2010 |
| WO | WO 2011049027 | * | 4/2011 |
| WO | WO 2011115137 | * | 9/2011 |

OTHER PUBLICATIONS

Haga; Inorg. Chem. 1991, 30, 475-480.*
Esteruelas; Organometallics 1992, 11, 702-705.*
Carmona; Organometallics 1995, 14, 2066-2080.*
Seo; Organic Electronics 2010, 11, 564-572.*
Freys; Chem. Commun., 2008, 4267-4269.*
Majumdar; J. Chem. Soc., Dalton Trans., 1998, 10, 1569-1574.*
Bushnell et al., Pyrazolyl-Bridged Iridium Dimers. 7.[1] Synthesis and Properties of Bridge-Substituted Analogues of [Ir(COD)(μ-pz)]$_2$ (pzH=Pyrazole), the "Mixed-Bridge" Complex [Ir$_2$(COD)$_2$(μ-pz)(μ-fpz)] (fpzH=3,5-Bis(trifluoromethyl)pyrazole), and the "Mixed-Metal" Dimer [IrRh(COD)$_2$(μ-pz)$_2$]. Crystal and Molecular Structures of Bis(cyclooctadiene)bis(μ-3-phenyl-5-methylpyrazolyl)-diiridium(I) (Dissymmetric Isomer) and Bis(cyclooctadiene)bis(μ-3,4,5-trimethylpyrazolyl)diiridium(I), Organometallics, vol. 4, pp. 1107-1114, 1985.
Costa et al., "Dumbbell-Shaped Dinuclear Iridium Complexes and Their Application to Light-Emitting Electrochemical Cells" Chemistry: A European Journal, vol. 16, pp. 9855-9863, 2010.
Ghavale et al., "Synthesis, structures and spectroscopic properties of platinum complexes containing orthometalated 2-phenylpyridine" Journal of Organometallic Chemistry, vol. 695, pp. 1237-1245, 2010.
Marshall et al., "Spectroscopy and Photochemistry of Binuclear Iridium(I) Complexes" Journal of the American Chemical Society, vol. 106, No. 10, pp. 3027-3029, 1984.
Müller et al., "Umsetzung von Chloro-Cyclooctadien-Methyl-Imidazoyl-Iridium mit Methyl-Oder Phenyllithium; Ungewöhnliche Bildung Eines Iridacyclopent Adienyl-Komplexes" Journal of Organometallic Chemistry, vol. 259, pp. C21-C25, 1983.
Rodman et al., "Electrogenerated Chemiluminescence. 52. Binuclear Iridium(I) Complexes" Inorganic Chemistry, vol. 29, No. 23, pp. 4699-4702, 1990.
International Preliminary Report on Patentability, issued on Jun. 4, 2013 in International Application No. PCT/JP2011/077979.

* cited by examiner

BINUCLEAR METAL COMPLEX, AND ORGANIC ELECTROLUMINESCENCE ELEMENT COMPRISING SAME

This application is the U.S. National Phase under 35 U.S.C. §371 of International Application No. PCT/JP2011/077979, filed Dec. 2, 2011, designating the U.S., and published in Japanese as WO 2012/074111 on Jun. 7, 2012, which claims priority to Japanese Patent Application No. 2010-269627 filed Dec. 2, 2010; and Japanese Patent Application No. 2011-029564, filed Feb. 15, 2011. The entire content of these applications is incorporated herein by reference.

TECHNICAL FIELD

The present invention relates to a binuclear metal complex, which is useful as a material for an organic electroluminescence element (hereinafter, sometimes referred to as "organic EL element"), for example, and an organic electroluminescence element comprising the same.

BACKGROUND ART

An organic EL element is promising for next-generation displays and next-generation lighting devices, and has been actively researched and developed in the country and in foreign countries. Various metal complexes have been reported as a luminescent material for an organic EL element with the view of enhancing efficiency, improving color purity, and extending the life span. (See Patent Documents 1 and 2, for example.)

Meanwhile, Non-Patent Documents 1, 3 and 4 disclose binuclear metal complexes, and methods of producing the complexes, but do not disclose any properties as a material for an organic EL element. Non-Patent Document 2 reports the synthesis of binuclear iridium complexes, and the examination of binuclear iridium complexes as a luminescent material for an organic EL element. Patent Documents 3 and 4 disclose binuclear metal complexes, and methods of producing the complexes, but do not disclose the complexes of the present invention such as a complex containing a biimidazole as a bridging ligand, for example.

CITATION LIST

Patent Document

Patent Document 1: WO2001/8230
Patent Document 2: WO2005/19373
Patent Document 3: JP-A-2003-73388
Patent Document 4: JP-B-4310077

Non-Patent Document

Non-patent Document 1: Journal of Organometallic Chemistry, 695, 1237 (2010)
Non-patent Document 2: Chemistry A European Journal, 16, 9855 (2010)
Non-patent Document 3: Journal of Organometallic Chemistry, 259, C21 (1983)
Non-patent Document 4: Organometallics, 4, 1107 (1985)

SUMMARY OF THE INVENTION

Problems to be Solved by the Invention

An object of the present invention is to provide a novel binuclear metal complex, which is useful as a material for an organic electroluminescence element, in particular.

Means for Solving the Problems

The present invention relates to the following items:
[1] A binuclear metal complex containing two metal atoms selected from the group consisting of Ru, Os, Rh, Ir and Pd, with the proviso that the two metal atoms may be the same as, or different from each other, and containing any one of the structures represented by the formulas (2) to (10):

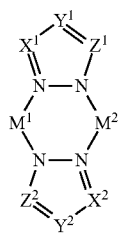

(2)

wherein
$X^1$ represents a nitrogen atom or $CR^1$, wherein $R^1$ represents a hydrogen atom or a substituent bound to the carbon atom,
$Y^1$ represents a nitrogen atom or $CR^2$, wherein $R^2$ represents a hydrogen atom or a substituent bound to the carbon atom,
$Z^1$ represents a nitrogen atom or $CR^3$, wherein $R^3$ represents a hydrogen atom or a substituent bound to the carbon atom,
$X^2$ represents a nitrogen atom or $CR^4$, wherein $R^4$ represents a hydrogen atom or a substituent bound to the carbon atom,
$Y^2$ represents a nitrogen atom or $CR^5$, wherein $R^5$ represents a hydrogen atom or a substituent bound to the carbon atom, and
$Z^2$ represents a nitrogen atom or $CR^6$, wherein $R^6$ represents a hydrogen atom or a substituent bound to the carbon atom, or alternatively,
two or more of $X^1$, $Y^1$ and $Z^1$, and two or more of $X^2$, $Y^2$ and $Z^2$ are joined together to form a cyclic structure, with the proviso that $X^1$, $Y^1$, $Z^1$, $X^2$, $Y^2$ and $Z^2$ may be the same as, or different from each other;

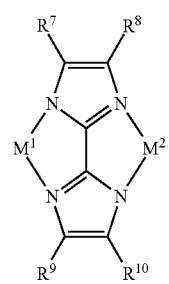

(3)

wherein

R$^7$, R$^8$, R$^9$ and R$^{10}$ may be the same as, or different from each other, and each independently represents a hydrogen atom or a substituent bound to the carbon atom, or alternatively, R$^7$ and R$^8$, and R$^9$ and R$^{10}$ are joined together with the carbon atom to which they are bound to form a cyclic structure other than benzene ring;

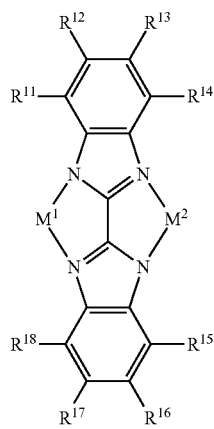

(4)

wherein

R$^{11}$, R$^{12}$, R$^{13}$, R$^{14}$, R$^{15}$, R$^{16}$, R$^{17}$ and R$^{18}$ may be the same as, or different from each other, and each independently represents a hydrogen atom or a substituent bound to the carbon atom, or alternatively, two or more of R$^{11}$ to R$^{14}$, and two or more of R$^{15}$ to R$^{18}$ are joined together with the carbon atom to which they are bound to form a cyclic structure;

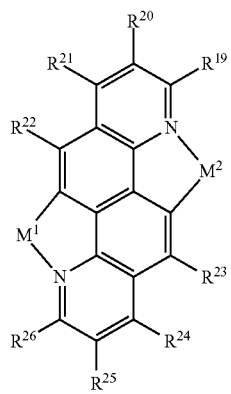

(5)

wherein

R$^{19}$, R$^{20}$, R$^{21}$, R$^{22}$, R$^{23}$, R$^{24}$, R$^{25}$ and R$^{26}$ may be the same as, or different from each other, and each independently represents a hydrogen atom or a substituent bound to the carbon atom, or alternatively, two or more of R$^{19}$ to R$^{22}$, and two or more of R$^{23}$ to R$^{26}$ are joined together with the carbon atom to which they are bound to form a cyclic structure;

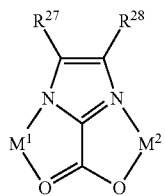

(6)

wherein

R$^{27}$ and R$^{28}$ may be the same as, or different from each other, and each independently represents a hydrogen atom or a substituent bound to the carbon atom, or alternatively, R$^{27}$ and R$^{28}$ are joined together with the carbon atom to which they are bound to form a cyclic structure;

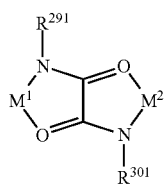

(7-1)

wherein

R$^{291}$ and R$^{301}$ may be the same as, or different from each other, and each independently represents a hydrogen atom or a substituent bound to the nitrogen atom, or alternatively, R$^{291}$ and R$^{301}$ are joined together with the nitrogen atom to which they are bound to form a cyclic structure;

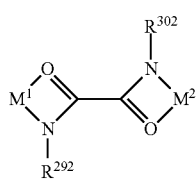

(7-2)

wherein

R$^{292}$ and R$^{302}$ may be the same as, or different from each other, and each independently represents a hydrogen atom or a substituent bound to the nitrogen atom, or alternatively, R$^{292}$ and R$^{302}$ are joined together with the nitrogen atom to which they are bound to form a cyclic structure;

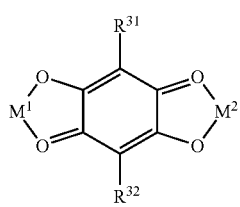

(8)

wherein

R$^{31}$ and R$^{32}$ may be the same as, or different from each other, and each independently represents a hydrogen atom or a substituent bound to the carbon atom;

(9)

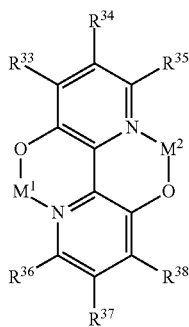

wherein $R^{33}$, $R^{34}$, $R^{35}$, $R^{36}$, $R^{37}$ and $R^{38}$ may be the same as, or different from each other, and each independently represents a hydrogen atom or a substituent bound to the carbon atom, or alternatively, two or more of $R^{33}$ to $R^{35}$, and two or more of $R^{36}$ to $R^{38}$ are joined together with the carbon atom to which they are bound to form a cyclic structure;

(10)

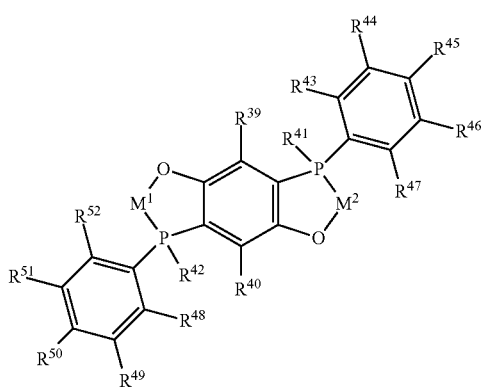

wherein $R^{39}$ and $R^{40}$ may be the same as, or different from each other, and each independently represents a hydrogen atom or a substituent bound to the carbon atom, $R^{41}$ and $R^{42}$ may be the same as, or different from each other, and each independently represents a hydrogen atom, an alkyl group or an aryl group which may have a substituent, and $R^{43}$, $R^{44}$, $R^{45}$, $R^{46}$, $R^{47}$, $R^{48}$, $R^{49}$, $R^{50}$, $R^{51}$ and $R^{52}$ may be the same as, or different from each other, and each independently represents a hydrogen atom or a substituent bound to the carbon atom, or alternatively, two or more of $R^{43}$ to $R^{47}$, and two or more of $R^{48}$ to $R^{52}$ are joined together with the carbon atom to which they are bound to form a cyclic structure;

with the proviso that in the formulas (2) to (10), $M^1$ and $M^2$ may be the same as, or different from each other, and each independently represents Ru, Os, Rh, Ir or Pd.

[2] The binuclear metal complex as described in [1], wherein the binuclear metal complex is represented by the formula (1):

$$(L^1)_m[M^1(L)_qM^2](L^2)_n \quad (1)$$

wherein $M^1$ and $M^2$ may be the same as, or different from each other, and each independently represents Ru, Os, Rh, Ir or Pd, and the moiety represented by the formula: $[M^1(L)_qM^2]$ represents any one of the structures represented by the formulas (2) to (10), wherein $L^1$ represents a ligand coordinated to the metal atom $M^1$, $L^2$ represents a ligand coordinated to the metal atom $M^2$, and m and n represent the numbers of $L^1$ and $L^2$, respectively, and each independently represents an integer of 1 or greater, with the proviso that in the cases where m is 2 or greater, two or more ligands $L^1$s may be the same as, or different from each other, and in the cases where n is 2 or greater, two or more ligands $L^2$s may be the same as, or different from each other.

[3] The binuclear metal complex as described in [2], wherein in the formula (1), each of $L^1$s and $L^2$s is a bidentate ligand, and m and n are 2, with the proviso that $L^1$ and $L^2$ may be the same as, or different from each other, two $L^1$s may be the same as, or different from each other, and two $L^2$s may be the same as, or different from each other.

[4] The binuclear metal complex as described in any one of [2] to [3], wherein in the formula (1), at least one of $L^1$s is a phenylpyridine compound represented by the formula (11), a pyridylpyridine compound represented by the formula (12), a phenylpyrazole compound represented by the formula (13), a phenylimidazole compound represented by the formula (14), or a phenylcarbene compound represented by the formula (15), and/or at least one of $L^2$s is a phenylpyridine compound represented by the formula (11), a pyridylpyridine compound represented by the formula (12), a phenylpyrazole compound represented by the formula (13), a phenylimidazole compound represented by the formula (14), or a phenylcarbene compound represented by the formula (15):

(11)

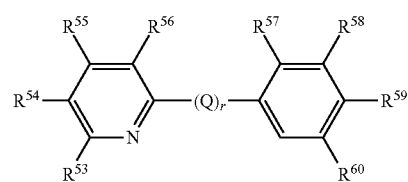

(12)

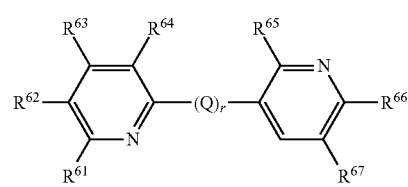

(13)

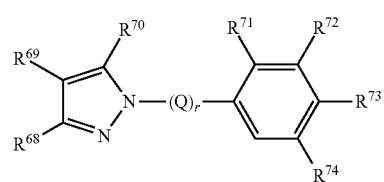

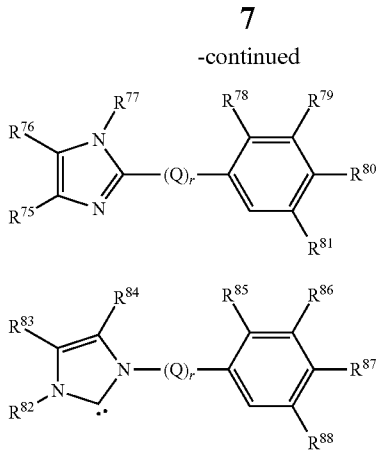

(14)

(15)

wherein
R[53] to R[88] may be the same as, or different from each other, and each independently represents a hydrogen atom or a substituent bound to the carbon atom or to the nitrogen atom, or alternatively, two or more of them are joined together to form a cyclic structure,
Q represents a divalent linking group, and
r represents 0 or 1.

[5] The binuclear metal complex as described in [4], wherein in the formula (1),
each of $M^1$ and $M^2$ is Ir,
each of $L^1$s and $L^2$s is any one of the bidentate ligands represented by the formulas (11) to (15), and
m and n are 2,
with the proviso that
$L^1$ and $L^2$ may be the same as, or different from each other,
two $L^1$s may be the same as, or different from each other, and
two $L^2$s may be the same as, or different from each other.

[6] The binuclear metal complex as described in [5], wherein in the formula (1),
each of $M^1$ and $M^2$ is Ir,
each of $L^1$ and $L^2$s is any one of the bidentate ligands represented by the formulas (11) to (15), and
m and n are 2,
with the proviso that
$L^1$ and $L^2$ may be the same as, or different from each other,
two $L^1$s may be the same as, or different from each other, and
two $L^2$s may be the same as, or different from each other,
and the moiety represented by the formula: $[M^1(L)_qM^2]$ represents any one of the structures represented by the formulas (16) to (24):

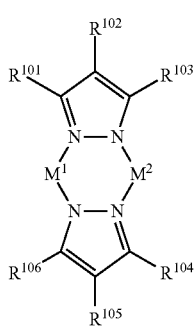

(16)

wherein
R[101] to R[106] may be the same as, or different from each other, and each independently represents a hydrogen atom, an alkyl group, an unsubstituted phenyl group or a halogen atom;

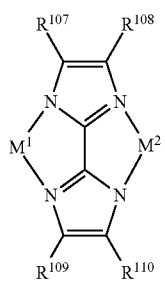

(17)

wherein
R[107] to R[110] may be the same as, or different from each other, and each independently represents a hydrogen atom, an alkyl group or a halogen atom;

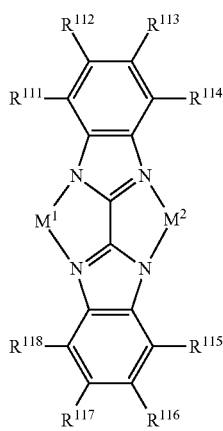

(18)

wherein
R[111] to R[118] may be the same as, or different from each other, and each independently represents a hydrogen atom, an alkyl group or a halogen atom;

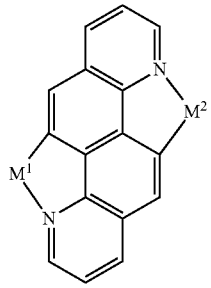

(19)

(20)

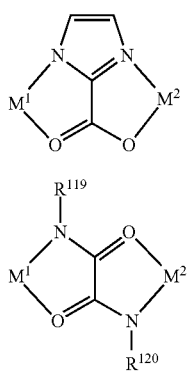

wherein
R"$^{119}$ to R$^{120}$ may be the same as, or different from each other, and each independently represents a hydrogen atom or an alkyl group, or alternatively, R$^{119}$ and R$^{120}$ are joined together to form a cyclic structure;

(21-2)

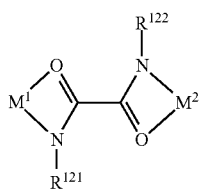

wherein
R$^{121}$ to R$^{122}$ may be the same as, or different from each other, and each independently represents a hydrogen atom or an alkyl group, or alternatively, R$^{121}$ and R$^{122}$ are joined together to form a cyclic structure;

(22)

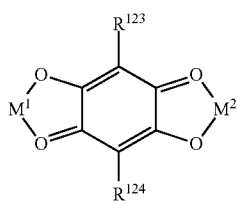

wherein
R$^{123}$ to R$^{124}$ may be the same as, or different from each other, and each independently represents a hydrogen atom, an alkyl group, a halogen atom or a nitro group;

(23)

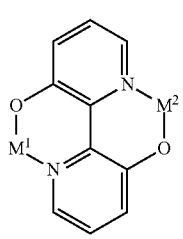

(24)

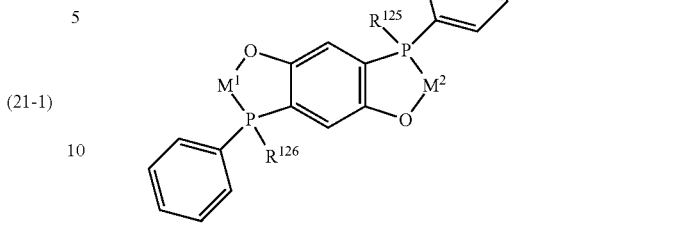

wherein
R$^{125}$ to R$^{126}$ may be the same as, or different from each other, and each independently represents a hydrogen atom, an alkyl group or an unsubstituted phenyl group;
with the proviso that in the formulas (16) to (24), each of M$^1$ and M$^2$ is It

[7] The binuclear metal complex as described in [5], wherein
two L$^1$s are the same as each other, and
two L$^2$s are the same as each other,
with the proviso that
L$^1$ and L$^2$ may be the same as, or different from each other,

[8] The binuclear metal complex as described in [6], wherein
two L$^1$s are the same as each other, and
two L$^2$s are the same as each other,
with the proviso that
L$^1$ and L$^2$ may be the same as, or different from each other,

[9] A synthetic precursor of binuclear metal complexs, represented by the formula (1a):

(1a)

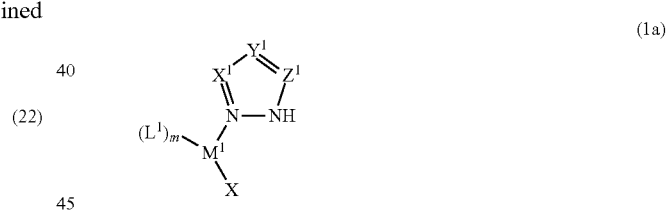

wherein
M$^1$, L$^1$, X$^1$, Y$^1$, Z$^1$ and m are defined as above, and
X represents a halogen atom.

[10] A synthetic precursor of binuclear metal complexs, represented by the formula (2a):

(2a)

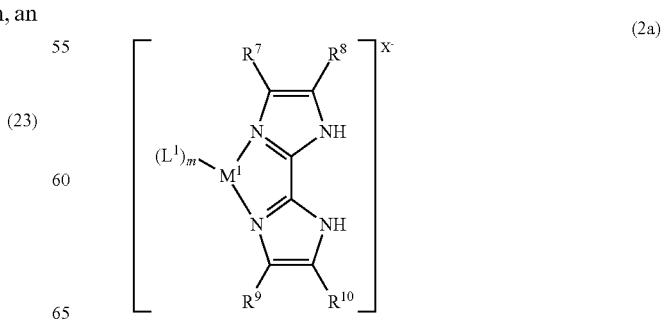

wherein $M^1$, $L^1$, $R^7$, $R^8$, $R^9$, $R^{10}$ and m are defined as above, and X represents a halogen atom.

[11] An organic electroluminescence element, comprising a binuclear metal complex as described in any one of [1] to [8].

Effect of the Invention

According to the present invention, there may be provided a novel binuclear metal complex, which is useful as a material for an organic electroluminescence element, for example. An organic electroluminescence element with a high performance may be produced when using the binuclear metal complex of the present invention for a luminescent layer.

DESCRIPTION OF EMBODIMENTS

Figure 1:
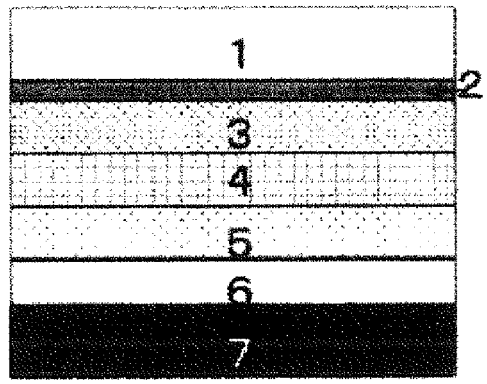
FIG. 1 is a diagram illustrating the construction of the organic electroluminescence element of Examples.
Figure 2:
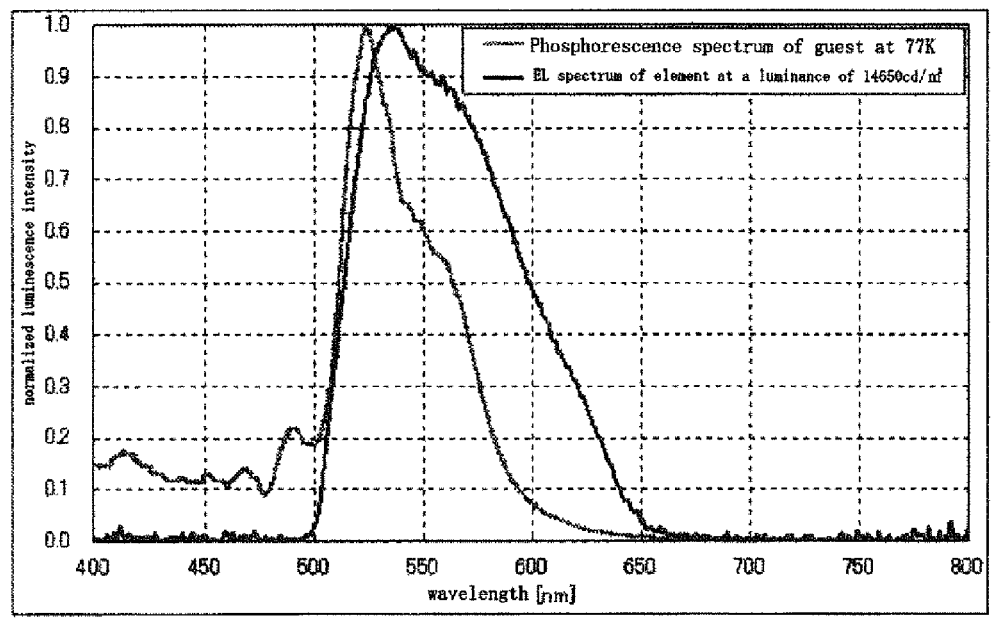
FIG. 2 is the EL spectrum of the organic EL element of Example 3.

<The Binuclear Metal Complex of the Present Invention>

The binuclear metal complex of the present invention contains two metal atoms selected from the group consisting of Ru, Os, Rh, Ir and Pd (with the proviso that the two metal atoms may be the same as, or different from each other) and contains any one of the structures represented by the above formulas (2) to (10).

The binuclear metal complex of the present invention may further contain one or more bridging ligands contained in any one of the structures represented by the formulas (2) to (10).

The binuclear metal complex of the present invention may be preferably represented by the above formula (1), or may preferably contain any one of the bridging structures represented by the formulas (2) to (10) and other ligands ($L^1$ and $L^2$ in the formula (1)), each of which is coordinated to one metal atom ($M^1$ and $M^2$ in the formula (1), respectively).

Preferable examples of the other ligands ($L^1$ and $L^2$ in the formula (1)) include, but not limited to, a phenylpyridine compound represented by the formula (11), a pyridylpyridine compound represented by the formula (12), a phenylpyrazole compound represented by the formula (13), a phenylimidazole compound represented by the formula (14), and a phenylcarbene compound represented by the formula (15). In the cases where the binuclear metal complex contains two or more ligands, the ligands may be the same as, or different from each other.

In addition, a bridging ligand contained in any one of the structures represented by the formulas (2) to (10) may be used as the other ligands ($L^1$ and $L^2$ in the formula (1)).

<The Metal Atoms; $M^1$ and $M^2$ in the Formulas (1) to (10)>

Each of the metal atoms contained in the binuclear metal complex of the present invention, i.e. $M^1$ and $M^2$ in the formulas (1) to (10), is Ru, Os, Rh, Ir or Pd, and may be preferably Rh or Ir, more preferably Ir. The two metal atoms, $M^1$ and $M^2$, may be the same as, or different from each other, and may be preferably the same as each other.

<The Structure Represented by the Formula (2); $[M^1(L)_qM^2]$ in the Formula (1)>

In the formula (2), $X^1$ represents a nitrogen atom or $CR^1$ (wherein $R^1$ represents a hydrogen atom or a substituent bound to the carbon atom), $Y^1$ represents a nitrogen atom or $CR^2$ (wherein $R^2$ represents a hydrogen atom or a substituent bound to the carbon atom), $Z^1$ represents a nitrogen atom or $CR^3$ (wherein $R^3$ represents a hydrogen atom or a substituent bound to the carbon atom), $X^2$ represents a nitrogen atom or $CR^4$ (wherein $R^4$ represents a hydrogen atom or a substituent bound to the carbon atom), $Y^2$ represents a nitrogen atom or $CR^5$ (wherein $R^5$ represents a hydrogen atom or a substituent bound to the carbon atom), and $Z^2$ represents a nitrogen atom or $CR^6$ (wherein $R^6$ represents a hydrogen atom or a substituent bound to the carbon atom), or alternatively, two or more of $X^1$, $Y^1$ and $Z^1$, and two or more of $X^2$, $Y^2$ and $Z^2$ are joined together to form a cyclic structure. In other words, two or more of the substituents, $R^1$, $R^2$ and $R^3$, and two or more of the substituents, $R^4$, $R^5$ and $R^6$, may be joined together to form a cyclic structure.

Although $X^1$, $Y^1$, $Z^1$, $X^2$, $Y^2$ and $Z^2$ may be the same as, or different from each other, it is preferred that $X^1$ and $X^2$ are the same as each other, and $Y^1$ and $Y^2$ are the same as each other, and $Z^1$ and $Z^2$ are the same as each other.

Examples of the $R^1$ to $R^6$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cycloheptyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamino, dipropylamino, dibutylamino, methylethylamino, methylpropylamino, methylbutylamino, diphenylamino and N-methyl-N-methanesulfonylamino; heterocyclic amino groups such as morpholino, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

In addition, two or more of the substituents, $R^1$, $R^2$ and $R^3$, and two or more of the substituents, $R^4$, $R^5$ and $R^6$, may be joined together to form a cyclic structure. Examples of the cyclic structure formed include 6- to 8-membered cyclic structures, and the cyclic structure may be particularly preferably benzene ring.

The structure represented by the formula (2) may be preferably the structure represented by the formula (16). In the formula (16), $R^{101}$ to $R^{106}$ each independently represents a hydrogen atom, an alkyl group, an unsubstituted phenyl group or a halogen atom. $R^{101}$ to $R^{106}$ may be preferably hydrogen, or a linear or branched alkyl group having 1 to 10 carbon atoms, more preferably hydrogen, or a linear or branched alkyl group having 1 to 5 carbon atoms, more preferably hydrogen or methyl, particularly preferably hydrogen.

Although $R^{101}$ to $R^{106}$ may be the same as, or different from each other, it is preferred that $R^{101}$ and $R^{104}$ are the same as each other, and $R^{102}$ and $R^{105}$ are the same as each other, and $R^{103}$ and $R^{106}$ are the same as each other.

<The structure Represented by the Formula (3); [$M^1(L)_qM^2$] in the formula (1)>

In the formula (3), $R^7$, $R^8$, $R^9$ and $R^{10}$ may be the same as, or different from each other, and each independently represents a hydrogen atom or a substituent bound to the carbon atom, or alternatively, $R^7$ and $R^8$, and $R^9$ and $R^{10}$ are joined together with the carbon atom to which they are bound to form a cyclic structure other than benzene ring. Although $R^7$ to $R^{10}$ may be the same as, or different from each other, it is preferred that $R^7$ to $R^{10}$ are the same as each other.

Examples of the $R^7$ to $R^{10}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, $R^7$ and $R^8$, and $R^9$ and $R^{10}$ may be joined together with the carbon atom to which they are bound to form a cyclic structure other than benzene ring. Examples of the cyclic structure formed include 6- to 8-membered cyclic structures.

The structure represented by the formula (3) may be preferably the structure represented by the formula (17). In the formula (17), $R^{107}$ to $R^{110}$ each independently represents a hydrogen atom, an alkyl group or a halogen atom. $R^{107}$ to $R^{110}$ may be preferably hydrogen, or a linear or branched alkyl group having 1 to 10 carbon atoms, more preferably hydrogen, or a linear or branched alkyl group having 1 to 5 carbon atoms, particularly preferably hydrogen.

Although $R^{107}$ to $R^{110}$ may be the same as, or different from each other, it is preferred that $R^{107}$ to $R^{110}$ are the same as each other.

<The Structure Represented by the Formula (4); [$M^1(L)_qM^2$] in the Formula (1)>

In the formula (4), $R^{11}$, $R^{12}$, $R^{13}$, $R^{14}$, $R^{15}$, $R^{16}$, $R^{17}$ and $R^{18}$ may be the same as, or different from each other, and each independently represents a hydrogen atom or a substituent bound to the carbon atom, or alternatively, two or more of $R^{11}$ to $R^{14}$, and two or more of $R^{15}$ to $R^{18}$ are joined together with the carbon atom to which they are bound to form a cyclic structure. Although $R^{11}$ to $R^{18}$ may be the same as, or different from each other, it is preferred that $R^{11}$ to $R^{18}$ are the same as each other.

Examples of the $R^{11}$ to $R^{18}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, two or more of $R^{11}$ to $R^{14}$, and two or more of $R^{15}$ to $R^{18}$ may be joined together with the carbon atom to which they are bound to form a cyclic structure. Examples of the cyclic structure formed include 6- to 8-membered cyclic structures.

The structure represented by the formula (4) may be preferably the structure represented by the formula (18). In the formula (18), $R^{111}$ to $R^{118}$ each independently represents a hydrogen atom, an alkyl group or a halogen atom. $R^{111}$ to $R^{118}$ may be preferably hydrogen, a linear or branched alkyl group having 1 to 10 carbon atoms, or a halogen atom, more preferably hydrogen, a linear or branched alkyl group having 1 to 5 carbon atoms, or a halogen atom, more preferably hydrogen, methyl, or fluorine atom, particularly preferably hydrogen or methyl.

Although $R^{111}$ to $R^{118}$ may be the same as, or different from each other, it is preferred that $R^{111}$ to $R^{118}$ are the same as each other.

<The Structure Represented by the Formula (5); [$M^1(L)_qM^2$] in the Formula (1)>

In the formula (5), $R^{19}$, $R^{20}$, $R^{21}$, $R^{22}$, $R^{23}$, $R^{24}$, $R^{25}$ and $R^{26}$ may be the same as, or different from each other, and each independently represents a hydrogen atom or a substituent bound to the carbon atom, or alternatively, two or more of $R^{19}$ to $R^{22}$, and two or more of $R^{23}$ to $R^{26}$ are joined together with the carbon atom to which they are bound to form a cyclic structure. Although $R^{19}$ to $R^{26}$ may be the same as, or different from each other, it is preferred that $R^{19}$ to $R^{26}$ are the same as each other.

Examples of the $R^{19}$ to $R^{26}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, two or more of $R^{19}$ to $R^{22}$, and two or more of $R^{23}$ to $R^{26}$ may be joined together with the carbon atom to which they are bound to form a cyclic structure. Examples of the cyclic structure formed include 6- to 8-membered cyclic structures.

The structure represented by the formula (5) may be preferably the structure represented by the formula (19).

<The Structure Represented by the Formula (6); [$M^1(L)_qM^2$] in the Formula (1)>

In the formula (6), $R^{27}$ and $R^{28}$ may be the same as, or different from each other, and each independently represents a hydrogen atom or a substituent bound to the carbon atom, or alternatively, $R^{27}$ and $R^{28}$ are joined together with the carbon atom to which they are bound to form a cyclic structure. Although $R^{27}$ to $R^{28}$ may be the same as, or different from each other, it is preferred that $R^{27}$ to $R^{28}$ are the same as each other.

Examples of the $R^{27}$ to $R^{28}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, $R^{27}$ and $R^{28}$ may be joined together with the carbon atom to which they are bound to form a cyclic structure. Examples of the cyclic structure formed include 6- to 8-membered cyclic structures.

The structure represented by the formula (6) may be preferably the structure represented by the formula (20).

<The Structure Represented by the Formula (7-1); $[M^1(L)_qM^2]$ in the Formula (1)>

In the formula (7-1), $R^{291}$ and $R^{301}$ may be the same as, or different from each other, and each independently represents a hydrogen atom or a substituent bound to the nitrogen atom, or alternatively, $R^{291}$ and $R^{301}$ are joined together with the nitrogen atom to which they are bound to form a cyclic structure. Although $R^{291}$ and $R^{301}$ may be the same as, or different from each other, it is preferred that $R^{291}$ and $R^{301}$ are the same as each other.

Examples of the $R^{291}$ and $R^{301}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, $R^{291}$ and $R^{301}$ may be joined together with the nitrogen atom to which they are bound to form a cyclic structure. Examples of the cyclic structure formed include 6- to 8-membered cyclic structures.

The structure represented by the formula (7-1) may be preferably the structure represented by the formula (21-1). In the formula (21-1), $R^{119}$ to $R^{120}$ each independently represents a hydrogen atom or an alkyl group, or alternatively, $R^{119}$ and $R^{120}$ are joined together to form a cyclic structure, preferably a 6- to 8-membered cyclic structure. $R^{119}$ to $R^{120}$ may be preferably hydrogen, or a linear or branched alkyl group having 1 to 10 carbon atoms, more preferably hydrogen, or a linear or branched alkyl group having 1 to 5 carbon atoms, more preferably hydrogen or methyl, particularly preferably methyl.

Although $R^{119}$ to $R^{120}$ may be the same as, or different from each other, it is preferred that $R^{119}$ to $R^{120}$ are the same as each other.

<The Structure Represented by the Formula (7-2); $[M^1(L)_qM^2]$ in the Formula (1)>

In the formula (7-2), $R^{292}$ and $R^{302}$ may be the same as, or different from each other, and each independently represents a hydrogen atom or a substituent bound to the nitrogen atom, or alternatively, $R^{292}$ and $R^{302}$ are joined together with the nitrogen atom to which they are bound to form a cyclic structure. Although $R^{292}$ and $R^{302}$ may be the same as, or different from each other, it is preferred that $R^{292}$ and $R^{302}$ are the same as each other.

Examples of the $R^{292}$ and $R^{302}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, $R^{292}$ and $R^{302}$ may be joined together with the nitrogen atom to which they are bound to form a cyclic structure. Examples of the cyclic structure formed include 6- to 8-membered cyclic structures.

The structure represented by the formula (7-2) may be preferably the structure represented by the formula (21-2). In the formula (21-2), $R^{121}$ to $R^{122}$ each independently represents a hydrogen atom or an alkyl group, or alternatively, $R^{121}$ and $R^{122}$ are joined together to form a cyclic structure, preferably a 6- to 8-membered cyclic structure. $R^{121}$ to $R^{122}$ may be preferably hydrogen, or a linear or branched alkyl group having 1 to 10 carbon atoms, more preferably hydrogen, or a linear or branched alkyl group having 1 to 5 carbon atoms, more preferably hydrogen or methyl, particularly preferably methyl.

Although $R^{121}$ to $R^{122}$ may be the same as, or different from each other, it is preferred that $R^{121}$ to $R^{122}$ are the same as each other.

<The Structure Represented by the Formula (8); $[M^1(L)_qM^2]$ in the Formula (1)>

In the formula (8), $R^{31}$ and $R^{32}$ may be the same as, or different from each other, and each independently represents a hydrogen atom or a substituent bound to the carbon atom. Although $R^{31}$ to $R^{32}$ may be the same as, or different from each other, it is preferred that $R^{31}$ to $R^{32}$ are the same as each other.

Examples of the $R^{31}$ to $R^{32}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

The structure represented by the formula (8) may be preferably the structure represented by the formula (22). In the formula (22), $R^{123}$ to $R^{124}$ each independently represents a hydrogen atom, an alkyl group, a halogen atom or a nitro group. $R^{123}$ to $R^{124}$ may be preferably hydrogen, or a linear or branched alkyl group having 1 to 10 carbon atoms, more preferably hydrogen, or a linear or branched alkyl group having 1 to 5 carbon atoms, more preferably hydrogen or methyl, particularly preferably hydrogen.

Although $R^{123}$ to $R^{124}$ may be the same as, or different from each other, it is preferred that $R^{123}$ to $R^{124}$ are the same as each other.

<The Structure Represented by the Formula (9); $[M^1(L)_qM^2]$ in the Formula (1)>

In the formula (9), $R^{33}$, $R^{34}$, $R^{35}$, $R^{36}$, $R^{37}$ and $R^{38}$ may be the same as, or different from each other, and each independently represents a hydrogen atom or a substituent bound to the carbon atom, or alternatively, two or more of $R^{33}$ to $R^{35}$, and two or more of $R^{36}$ to $R^{38}$ are joined together with the carbon atom to which they are bound to form a cyclic structure. Although $R^{33}$ to $R^{38}$ may be the same as, or different from each other, it is preferred that $R^{33}$ to $R^{38}$ are the same as each other.

Examples of the $R^{33}$ to $R^{38}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, two or more of $R^{33}$ to $R^{35}$, and two or more of $R^{36}$ to $R^{38}$ may be joined together with the carbon atom to which they are bound to form a cyclic structure. Examples of the cyclic structure formed include 6- to 8-membered cyclic structures.

The structure represented by the formula (9) may be preferably the structure represented by the formula (23). In other words, the structure in which the substituents on the pyridine rings are hydrogen atoms may be particularly preferred.

<The Structure Represented by the Formula (10); $[M^1(L)_qM^2]$ in the formula (1)>

In the formula (10), $R^{39}$ and $R^{40}$ may be the same as, or different from each other, and each independently represents a hydrogen atom or a substituent bound to the carbon atom, and $R^{41}$ and $R^{42}$ may be the same as, or different from each other, and each independently represents a hydrogen atom, an alkyl group or an aryl group which may have a substituent, and $R^{43}$, $R^{44}$, $R^{45}$, $R^{46}$, $R^{47}$, $R^{48}$, $R^{49}$, $R^{50}$, $R^{51}$ and $R^{52}$ may be the same as, or different from each other, and each independently represents a hydrogen atom or a substituent bound to the carbon atom, or alternatively, two or more of $R^{43}$ to $R^{47}$, and two or more of $R^{48}$ to $R^{52}$ are joined together with the carbon atom to which they are bound to form a cyclic structure. Although $R^{39}$ and $R^{40}$ may be the same as, or different from each other, it is preferred that $R^{39}$ and $R^{40}$ are the same as each other. Although $R^{41}$ and $R^{42}$ may be the same as, or different from each other, it is preferred that $R^{41}$ and $R^{42}$ are the same as each other. Although $R^{43}$ to $R^{52}$ may be the same as, or different from each other, it is preferred that $R^{43}$ to $R^{52}$ are the same as each other.

Examples of the $R^{39}$ and $R^{40}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

Examples of the $R^{41}$ and $R^{42}$ include a hydrogen atom, linear or branched alkyl groups such as methyl, ethyl, propyl, butyl, pentyl and hexyl, which preferably have 1 to 10 carbon atoms, and substituted or unsubstituted aryl groups such as phenyl, tolyl, fluorophenyl, xylyl, biphenylyl, naphthyl, anthryl and phenanthryl, preferably unsubstituted aryl groups.

Examples of the $R^{43}$ to $R^{52}$ include a hydrogen atom, a substituent bound through the carbon atom, a substituent bound through the oxygen atom, a substituent bound through the nitrogen atom, a substituent bound through the sulfur atom, and a halogen atom. Examples of the substituent bound through the carbon atom, the substituent bound through the oxygen atom, the substituent bound through the nitrogen atom, the substituent bound through the sulfur atom, and the halogen atom include those listed as the $R^1$ to $R^6$ in the formula (2).

In addition, two or more of $R^{43}$ to $R^{47}$, and two or more of $R^{48}$ to $R^{52}$ may be joined together with the carbon atom to which they are bound to form a cyclic structure. Examples of the cyclic structure formed include 6- to 8-membered cyclic structures.

The structure represented by the formula (10) may be preferably the structure represented by the formula (24). In the formula (24), $R^{125}$ to $R^{126}$ each independently represents a hydrogen atom, an alkyl group or an unsubstituted phenyl group. $R^{125}$ to $R^{126}$ may be preferably hydrogen, a linear or branched alkyl group having 1 to 10 carbon atoms, or an unsubstituted phenyl group, more preferably hydrogen, a linear or branched alkyl group having 1 to 5 carbon atoms, or an unsubstituted phenyl group, particularly preferably unsubstituted phenyl group.

Although $R^{125}$ to $R^{126}$ may be the same as, or different from each other, it is preferred that $R^{125}$ to $R^{126}$ are the same as each other.

<The other Ligands; $L^1$ and $L^2$ in the Formula (1)>

The binuclear metal complex of the present invention contains any one of the structures represented by the above formulas (2) to (10), and may further contain other ligands.

In the formula (1), the other ligands are represented by $L^1$ and $L^2$, and $L^1$ represents a ligand coordinated to the metal atom $M^1$, $L^2$ represents a ligand coordinated to the metal atom $M^2$, and m and n represent the numbers of $L^1$ and $L^2$, respectively, and each independently represents an integer of 1 or greater, with the proviso that in the cases where m is 2 or greater, two or more ligands $L^1$s may be the same as, or different from each other, and in the cases where n is 2 or greater, two or more ligands $L_2$s may be the same as, or different from each other.

The denticity and valence of the other ligands are not limited, and the other ligands may be a monodentate ligand, a bidentate ligand, a tridentate ligand, or a tetradentate ligand. In addition, the ligands coordinated to one metal atom ($M^1$ or $M^2$ in the formula (1)) may be a combination of two or more different monodentate ligands, a combination of two or more different bidentate ligands, a combination of one or two monodentate ligands and one bidentate ligand, or a combination of one monodentate ligand and one tridentate ligand, for example.

The total number of ligands depends on the oxidation state and coordination number of the metal atom used and on the valence and denticity of the ligands used.

In the formula (1), in the cases where the metal atoms $M^1$ and $M^2$ are metals having a coordination number of 6, including Ir,
  m and n are 4 when all of $L^1$ and $L^2$ are monodentate ligands,
  m and n are 2 when all of $L^1$ and $L^2$ are bidentate ligands,
  m and n are 1 when $L^1$ and $L^2$ are tetradentate ligands,
  m and n are 3 when $L^1$ and $L^2$ are combinations of monodentate ligand and bidentate ligand (two monodentate ligands and one bidentate ligand),
  m and n are 2 when $L^1$ and $L^2$ are combinations of monodentate ligand and tridentate ligand (one monodentate ligand and one tridentate ligand).
In the cases where the metal atoms $M^1$ and $M^2$ are tetravalent metals,
  m and n are 2 when all of $L^1$ and $L^2$ are monodentate ligands,
  m and n are 1 when $L^1$ and $L^2$ are bidentate ligands.

Examples of the other ligand include neutral ligands such as phosphine, phosphonate, arsenate, phosphite, CO, pyridine, nitrile, $\eta^4$-1,4-dinitrile-1,3-butadiene, 2,4-hexadiene, butadiene, $\eta^2$-cyclooctene, $\eta^4$-1,3-cyclooctadiene and $\eta^4$-1,5-cyclooctadiene; and anionic ligands such as chloro, bromo, cyano, acetylacetonato, hexafluoroacetylacetonato, 8-hydroxyquinolinato, imineacetylacetonato, tetramethylheptanedionato, 1-(2-hydroxyphenyl)pyrazolate, phenyl pyrazolate, 3-(2-pyridyl)-5-t-butylpyrazolate, 3-(2-pyridyl)-5- trifluoromethylpyrazolate and 2-(2-pyridyl)-4-trifluoromethyl-1,3,5-triazolate.

The other ligands, i.e. $L^1$ and $L^2$ in the formula (1), may be preferably a bidentate ligand, more preferably a monovalent anionic bidentate ligand. A phenylpyridine compound, a pyridylpyridine compound, a phenylpyrazole compound, a phenylimidazole compound, or a phenylcarbene compound may be preferably used as a compound to be converted into the monovalent anionic bidentate ligand.

In the formula (1), it is preferred that at least one of $L^1$, more preferably all of $L^1$, is a phenylpyridine compound represented by the formula (11), a pyridylpyridine compound represented by the formula (12), a phenylpyrazole compound represented by the formula (13), a phenylimidazole compound represented by the formula (14), or a phenylcarbene compound represented by the formula (15). It is also preferred that at least one of $L^2$, more preferably all of $L^2$, is a phenylpyridine compound represented by the formula (11), a pyridylpyridine compound represented by the formula (12), a phenylpyrazole compound represented by the formula (13), a phenylimidazole compound represented by the formula (14), or a phenylcarbene compound represented by the formula (15). In such cases, $L^1$ and $L^2$ may be the same as, or different from each other, and two $L^1$s may be the same as, or different from each other, and two $L^2$s may be the same as, or different from each other.

In the binuclear metal complex of the present invention, it is preferred that the ligands coordinated to one metal atom are the same as each other. In other words, it is preferred that in the formula (1), two $L^1$s are the same as each other, and two $L^2$s are the same as each other. The ligands $L^1$s coordinated to the metal atom $M^1$ and the ligands $L^2$s coordinated to the metal atom $M^2$ may be the same as, or different from each other.

<The Phenylpyridine Compound (11); $L^1$ and $L^2$ in the Formula (1)>

The phenylpyridine compound is represented by the formula (11).

In the formula (11), $R^{53}$ to $R^{60}$ may be the same as, or different from each other, and each independently represents a hydrogen atom or a substituent bound to the carbon atom, or alternatively, two or more of them are joined together to form a cyclic structure.

Examples of the $R^{53}$ to $R^{60}$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cyclopentyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamino, dipropylamino, dibutylamino, methylethylamino, methylpropylamino, methylbutylamino, diphenylamino and N-methyl-N-methanesulfonylamino; heterocyclic amino groups such as morpholino, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

The number and position of substituents are not limited.

In addition, two or more of the substituents may be joined together to form a cyclic structure. Examples of the cyclic structure formed include 6- to 8-membered cyclic structures.

$R^{53}$ to $R^{60}$ may be preferably a hydrogen atom or a halogen atom, more preferably a hydrogen atom or a fluorine atom.

In one particularly preferred embodiment of the phenylpyridine compound represented by the formula (11), $R^{53}$ to $R^{60}$ are hydrogen, or alternatively, $R^{53}$ to $R^{56}$, $R^{58}$ and $R^{60}$ are hydrogen, and $R^{57}$ and $R^{59}$ are fluorine.

In addition, Q represents a divalent linking group. Examples of the Q include methylene which may be substituted by methyl or fluorine; oxy group; thio group; sulfonyl; and silylene which may be substituted by methyl or phenyl; and the Q may be preferably methylene. In addition, r represents 0 or 1, and may be preferably 0. Accordingly, it is particularly preferred that the moiety represented by the formula: $(Q)_r$ is a single bond (r is 0, and no divalent linking group Q is present.).

<The Pyridylpyridine Compound (12); $L^1$ and $L^2$ in the Formula (1)>

The pyridylpyridine compound is represented by the formula (12).

In the formula (12), $R^{61}$ to $R^{67}$ may be the same as, or different from each other, and each independently represents a hydrogen atom or a substituent bound to the carbon atom, or alternatively, two or more of them are joined together to form a cyclic structure.

Examples of the $R^{61}$ to $R^{67}$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cyclopentyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamine, dipropylamino, dibutylamino, methylethylamino, methylpropylamino, methylbutylamino, diphenylamino and N-methyl-N-methanesulfonylamino; heterocyclic amino groups such as morpholino, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

The number and position of substituents are not limited.

In addition, two or more of the substituents may be joined together to form a cyclic structure. Examples of the cyclic structure formed include 6- to 8-membered cyclic structures.

$R^{61}$ to $R^{67}$ may be preferably a hydrogen atom, or a linear or branched alkyl group having 1 to 10 carbon atoms, or a halogen atom, more preferably a hydrogen atom, a methyl group, or a fluorine atom.

In one particularly preferred embodiment of the pyridylpyridine compound represented by the formula (12), $R^{61}$ to $R^{64}$ and $R^{67}$ are hydrogen, and $R^{65}$ and $R^{66}$ are fluorine, or alternatively, $R^{61}$ to $R^{62}$, $R^{64}$ and $R^{67}$ are hydrogen, $R^{63}$ is methyl, and $R^{65}$ and $R^{66}$ are fluorine.

In addition, Q represents a divalent linking group. Examples of the Q include methylene which may be substituted by methyl or fluorine; oxy group; thio group; sulfonyl; and silylene which may be substituted by methyl or phenyl; and the Q may be preferably methylene. In addition, r represents 0 or 1, and may be preferably 0. Accordingly, it is particularly preferred that the moiety represented by the formula: $(Q)_r$ is a single bond (r is 0, and no divalent linking group Q is present.).

<The Phenylpyrazole Compound (13); $L^1$ and $L^2$ in the Formula (1)>

The phenylpyrazole compound is represented by the formula (13).

In the formula (13), $R^{68}$ to $R^{74}$ may be the same as, or different from each other, and each independently represents a hydrogen atom or a substituent bound to the carbon atom, or alternatively, two or more of them are joined together to form a cyclic structure.

Examples of the $R^{68}$ to $R^{74}$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cyclopentyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamino, dipropylamino, dibutylamino, methylethylamino, methylpropylamino, methylbutylamino, diphenylamino and N-methyl-N-methanesulfonylamino; heterocyclic amino groups such as morpholino, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

The number and position of substituents are not limited.

In addition, two or more of the substituents may be joined together to form a cyclic structure. Examples of the cyclic structure formed include 6- to 8-membered cyclic structures.

$R^{68}$ to $R^{74}$ may be preferably a hydrogen atom or a halogen atom, more preferably a hydrogen atom or a fluorine atom.

In one particularly preferred embodiment of the phenylpyrazole compound represented by the formula (13), $R^{68}$ to $R^{74}$ are hydrogen, or alternatively, $R^{68}$ to $R^{70}$, $R^{72}$ and $R^{74}$ are hydrogen, and $R^{71}$ and $R^{73}$ are fluorine.

In addition, Q represents a divalent linking group. Examples of the Q include methylene which may be substituted by methyl or fluorine; oxy group; thio group; sulfonyl; and silylene which may be substituted by methyl or phenyl; and the Q may be preferably methylene. In addition, r represents 0 or 1, and may be preferably 0. Accordingly, it is particularly preferred that the moiety represented by the formula: $(Q)_r$ is a single bond (r is 0, and no divalent linking group Q is present.).

<The Phenylimidazole Compound (14); $L^1$ and $L^2$ in the Formula (1)>

The phenylimidazole compound is represented by the formula (14).

In the formula (14), $R^{75}$ to $R^{81}$ may be the same as, or different from each other, and each independently represents a hydrogen atom or a substituent bound to the carbon atom or to the nitrogen atom, or alternatively, two or more of them are joined together to form a cyclic structure.

Examples of the $R^{75}$ to $R^{81}$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cyclopentyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamino, dipropylamino, dibutylamino, methylethylamino, methylpropylamino, methylbutylamino, diphenylamino and N-methyl-N-methanesulfonylamino; heterocyclic amino groups such as morpholino, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

The number and position of substituents are not limited.

In addition, two or more of the substituents may be joined together to form a cyclic structure. Examples of the cyclic structure formed include 6- to &membered cyclic structures.

$R^{75}$ to $R^{81}$ may be preferably a hydrogen atom, a linear or branched alkyl group having 1 to 10 carbon atoms, or a halogen atom, more preferably a hydrogen atom, a methyl group, or a fluorine atom.

In one particularly preferred embodiment of the phenylimidazole compound represented by the formula (14), $R^{75}$, $R^{76}$ and $R^{78}$ to $R^{81}$ are hydrogen, and $R^{77}$ is methyl.

In addition, Q represents a divalent linking group. Examples of the Q include methylene which may be substituted by methyl or fluorine; oxy group; thio group; sulfonyl; and silylene which may be substituted by methyl or phenyl; and the Q may be preferably methylene. In addition, r represents 0 or 1, and may be preferably 0. Accordingly, it is particularly preferred that the moiety represented by the formula: $(Q)_r$ is a single bond (r is 0, and no divalent linking group Q is present.).

<The Phenylcarbene Compound (15); $L^1$ and $L^2$ in the Formula (1)>

The phenylcarbene compound is represented by the formula (15).

In the formula (15), $R^{82}$ to $R^{88}$ may be the same as, or different from each other, and each independently represents a hydrogen atom or a substituent bound to the carbon atom or to the nitrogen atom, or alternatively, two or more of them are joined together to form a cyclic structure.

Examples of the $R^{82}$ to $R^{88}$ include a hydrogen atom, a substituent bound through the carbon atom, a substituent bound through the oxygen atom, a substituent bound through the nitrogen atom, a substituent bound through the sulfur atom, and a halogen atom.

Examples of the substituent bound through the carbon atom include alkyl groups such as methyl, ethyl, propyl, butyl, pentyl and hexyl; cycloalkyl groups such as cyclopropyl, cyclobutyl, cyclopentyl, cyclohexyl and cycloheptyl; alkenyl groups such as vinyl, allyl, propenyl, cyclopropenyl, cyclobutenyl and cyclopentenyl; heterocyclic groups such as quinolyl, pyridyl, pyrrolidyl, pyrrolyl, furyl and thienyl; aryl groups such as phenyl, tolyl, fluorophenyl, xylyl, biphenylyl, naphthyl, anthryl and phenanthryl; acyl groups (which may be acetalized) such as acetyl, propionyl, acryloyl, pivaloyl, cyclohexylcarbonyl, benzoyl, naphthoyl and toluoyl; carboxyl group; alkoxycarbonyl groups such as methoxycarbonyl and ethoxycarbonyl; aryloxycarbonyl groups such as phenoxycarbonyl; halogenated alkyl groups such as trifluoromethyl; and cyano group. These groups may include various isomers.

Examples of the substituent bound through the oxygen atom include hydroxyl group; alkoxy groups such as methoxy, ethoxy, propoxy, butoxy, pentyloxy, hexyloxy, heptyloxy and benzyloxy; and aryloxy groups such as phenoxy, toluyloxy and naphthyloxy. These groups may include various isomers.

Examples of the substituent bound through the nitrogen atom include primary amino groups such as methylamino, ethylamino, propylamino, butylamino, cyclohexylamino, phenylamino and naphthylamino; secondary amino groups such as dimethylamino, diethylamino, dipropylamino, dibutylamino, methylethylamino, methylpropylamino, methylbutylamino, diphenylamino and N-methyl-N-methanesulfonylamino; heterocyclic amino groups such as morpholine, piperidino, piperazinyl, pyrazolidinyl, pyrrolidino and indolyl; and imino group. These groups may include various isomers.

Examples of the substituent bound through the sulfur atom include mercapto group; thioalkyl groups such as thiomethyl, thioethyl and thiopropyl; and thioaryl groups such as thiophenyl, thiotoluyl and thionaphthyl. These groups may include various isomers.

Examples of the halogen atom include fluorine atom, chlorine atom, bromine atom, and iodine atom.

The number and position of substituents are not limited.

In addition, two or more of the substituents may be joined together to form a cyclic structure. Examples of the cyclic structure formed include 6- to 8-membered cyclic structures.

$R^{82}$ to $R^{88}$ may be preferably a hydrogen atom, a linear or branched alkyl group having 1 to 10 carbon atoms, or a halogen atom, more preferably a hydrogen atom, a methyl group, or a fluorine atom.

In one particularly preferred embodiment of the phenylcarbene compound represented by the formula (15), $R^{83}$ to $R^{88}$ are hydrogen, and $R^{82}$ is methyl, or alternatively, $R^{83}$ to $R^{85}$ and $R^{87}$ are hydrogen, $R^{86}$ and $R^{88}$ are fluorine, and $R^{82}$ is methyl.

In addition, Q represents a divalent linking group. Examples of the Q include methylene which may be substituted by methyl or fluorine; oxy group; thio group; sulfonyl; and silylene which may be substituted by methyl or phenyl; and the Q may be preferably methylene. In addition, r represents 0 or 1, and may be preferably 0. Accordingly, it is particularly preferred that the moiety represented by the formula: $(Q)_r$ is a single bond (r is 0, and no divalent linking group Q is present.).

<The Method of Producing the Binuclear Metal Complex of the Present Invention>

In the cases where the moiety L in the $[M^1(L)_qM^2]$ consists of two molecules of monodentate ligand, the binuclear metal complex may be synthesized by reacting a binuclear metal complex which are bridged with two halogen atoms and one molecule of monodentate ligand in a room-temperature-to-heated state in the presence of a solvent and, optionally a base, and then reacting the resulting intermediate in a room-temperature-to-heated state in the presence of a solvent and a base.

In the cases where the moiety L in the $[M^1(L)_qM^2]$ consists of one molecule of tetradentate ligand, the binuclear metal complex may be synthesized by reacting a binuclear metal complex which are bridged with two halogen atoms and one molecule of tetradentate ligand in a room-temperature-to-heated state in the presence of a solvent and a base, or alternatively, by reacting a binuclear metal complex which are bridged with two halogen atoms and one molecule of tetradentate ligand in a room-temperature-to-heated state in the presence of a solvent and, optionally a base, and then reacting the resulting intermediate in a room-temperature-to-heated state in the presence of a solvent and a base.

The binuclear metal complex of the present invention, which is represented by the formula (1) in which each of $M^1$ and $M^2$ is Ir, the moiety represented by the formula: $[M^1(L)_qM^2]$ is the structure represented by the formula (2), each of $X^1, Y^1, Z^1, X^2, Y^2$ and $Z^2$ is —CH—, and $L^1$ and $L^2$ are the same as each other and each of them is a phenylpyridine derivative represented by the formula (11), and m and n are 2, for example, may be synthesized according to the following scheme.

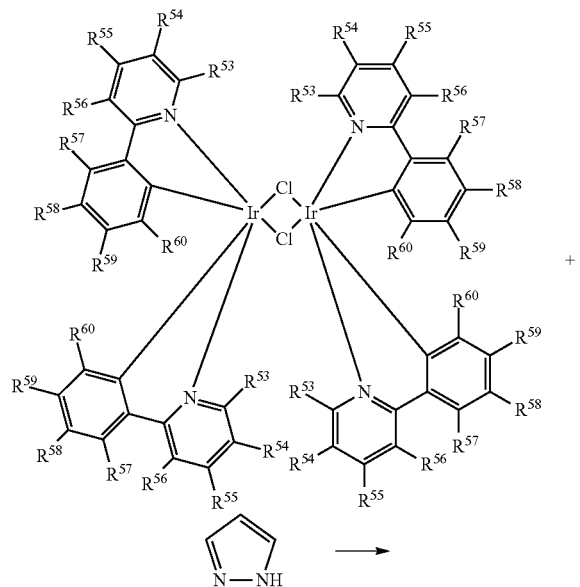

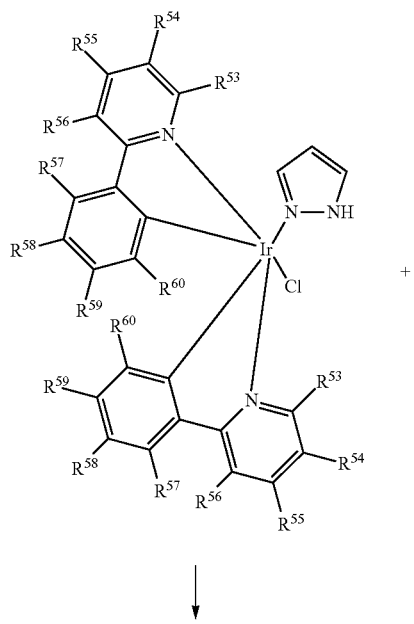

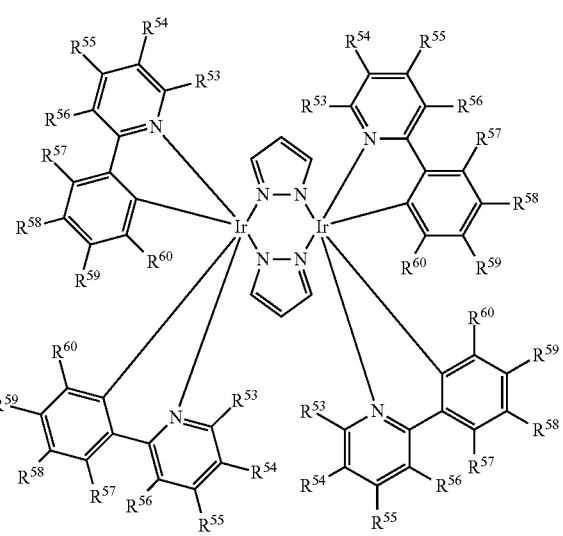

wherein $R^{53}$ to $R^{60}$ are defined as above.

The synthetic precursor of the binuclear metal complex represented by the formula (1) in which the moiety represented by the formula: $[M^1(L)_qM^2]$ is the structure represented by the formula (2), i.e. the synthetic precursor represented by the formula (1a), is a novel compound.

The binuclear metal complex, which is represented by the formula (1) in which each of $M^1$ and $M^2$ is Ir, the moiety represented by the formula: $[M^1(L)_qM^2]$ is the structure represented by the formula (3), $L^1$ and $L^2$ are the same as each other and each of them is a phenylpyridine derivative represented by the formula (11), and m and n are 2, may be synthesized in two stages with isolating the intermediate as shown in the following scheme, or may be synthesized in one stage without isolating the intermediate.

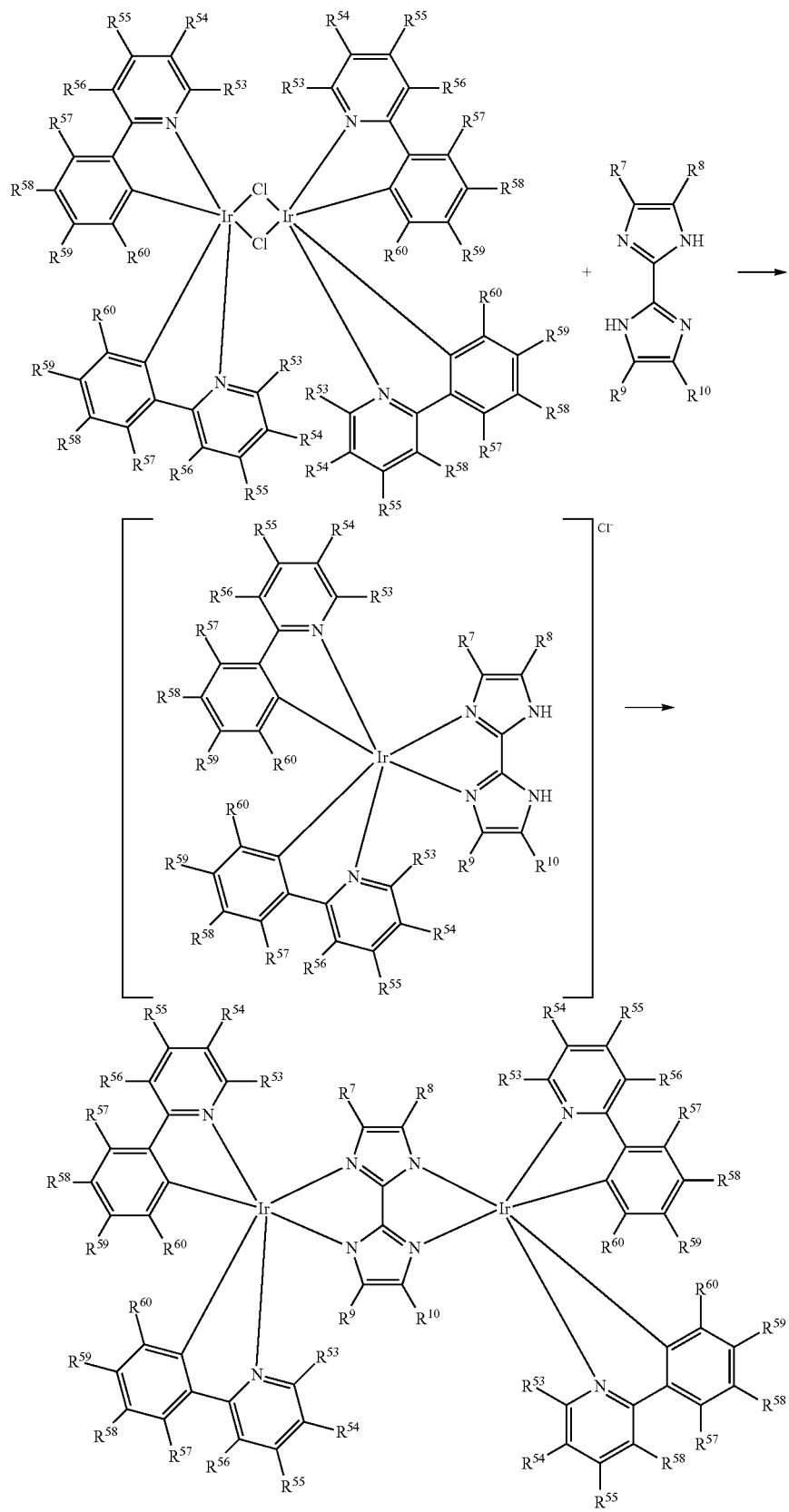
wherein $R^7$, $R^8$, $R^9$, $R^{10}$ and $R^{53}$ to $R^{60}$ are defined as above.

The synthetic precursor of the binuclear metal complex represented by the formula (1) in which the moiety represented by the formula: $[M^1(L)_qM^2]$ is the structure represented by the formula (3), i.e. the synthetic precursor represented by the formula (2a), is a novel compound.

In addition, the other binuclear metal complexes of the present invention may be produced in the same way as described above.

<The Organic Electroluminescence Element of the Present Invention>

There will be described the organic electroluminescence element of the present invention. The organic EL element of the present invention comprises the binuclear metal complex, particularly iridium complex, of the present invention. The binuclear metal complex of the present invention is generally used as a luminescent material.

A known structure and a known material may be used for the organic EL element of the present invention, except that the binuclear metal complex of the present invention is used, for example, in a luminescent layer, and the like.

The organic EL element of the present invention may be preferably an organic EL element comprising a single or multiple organic compound layers between a pair of electrodes, which comprises the binuclear metal complex of the present invention in at least one of the organic compound thin layer(s). The organic compound layers may include a buffer layer, a hole-injection layer, a hole-transport layer, a luminescent layer, an electron-transport layer, an electron-injection layer, and the like.

The single-layer organic EL element comprises a luminescent layer between an anode and a cathode. The luminescent layer comprises a luminescent material, and may further comprise a material used in an organic compound layer for the transportation of holes injected from the anode, or electrons injected from the cathode to the luminescent material, e.g. a hole-transport material or an electron-transport material.

As for the multi-layer organic EL element, examples of the multi-layer construction include, but not limited to, (anode/buffer layer/hole-transport layer/luminescent layer/hole-blocking layer/electron-transport layer/cathode) and (anode/buffer layer/hole-transport layer/luminescent layer/electron-transport layer/cathode), as well as (anode/hole-injection layer/hole-transport layer/luminescent layer/hole-blocking layer/electron-transport layer/metal-oxide layer/cathode), (anode/hole-injection layer/luminescent layer/cathode), (anode/luminescent layer/electron-transport layer/cathode) and (anode/hole-injection layer/luminescent layer/electron-transport layer/cathode).

In addition, the buffer layer, the hole-transport layer, the electron-transport layer and the luminescent layer each may have a single-layer construction, or a multi-layer construction. In addition, as the hole-transport layer and the electron-transport layer, a layer having an injection function (a hole-injection layer and an electron-injection layer) and a layer having a transport function (a hole-transport layer and an electron-transport layer) may be provided separately in each layer.

There will be described the constituent elements of the organic EL element of the present invention in detail, using the element construction of (anode/buffer layer/hole-transport layer/luminescent layer/hole-blocking layer/electron-transport layer/cathode) as an example.

In the organic EL element of the present invention, any host material may be selected from known host materials and used as the host material in the luminescent layer of the organic layer. Examples of the host material include, but not limited to, 4,4'-di(N-carbazolyl)-1,1'-biphenyl (CBP), 1,3-di(N-carbazolyl)benzene (mCP), 2,2'-di[4"-(N-carbazolyl)phenyl]-1,1'-biphenyl (4CzPBP), diphenyl di(o-tolyl)silane, p-bis(triphenylsilyl)benzene, 4,4',4"-tris(N-carbazolyl)-triphenylamine (TCTA), and 49,10-bis-[1,1,3',1']terphenyl-5'-yl-anthracene.

The binuclear metal complex of the present invention is generally used in combination with a host material in the luminescent layer. In such cases, the binuclear metal complex of the present invention as a luminescent material may be preferably used in an amount of from 0.005 wt % to 40 wt %, more preferably from 0.05 wt % to 10 wt %, relative to the host material.

As for the material to be used as the hole-blocking layer (hereinafter, referred to as "hole-blocking material"), any material may be selected from known materials and used as the hole-blocking material. Examples of the hole-blocking material include, but not limited to, 2,9-dimethyl-4,7-diphenyl-1,10-phenanthroline, bis(2-methyl-8-quinolinolato)(μ-phenylphenolato)aluminum, and bis(2-methyl-8-quinolinolato)(triphenylsilanolato)aluminum.

As for the material to be used as the electron-transport layer (hereinafter, referred to as "electron-transport material"), any material may be selected from known materials and used as the electron-transport material. Examples of the electron-transport material include fluorene, phenanthroline, bathophenanthroline, bathocuproine, anthraquinodimethane, diphenoquinone, oxazole, oxadiazole, triazole, imidazole, anthraquinodimethane and 4,4'-N,N'-dicarbazole biphenyl (CBP), and compounds, metal complex compounds or nitrogen-containing 5-membered cyclic derivatives thereof. Specific examples of the metal complex compound include, but not limited to, 8-hydroxyquinolinato lithium, tris(8-hydroxyquinolinato)aluminum, tri(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)(o-cresolato)gallium, bis(2-methyl-8-quinolinato)(1-naphtholato)aluminum, and bis(2-methyl-8-quinolinato)-4-phenylphenolate. In addition, the nitrogen-containing 5-membered cyclic derivative may be preferably an oxazole derivative, a thiazole derivative, an oxadiazole derivative, a thiadiazole derivative, or a triazole derivative. Specific examples of the nitrogen-containing 5-membered cyclic derivative include, but not limited to, 2,5-bis(1-phenyl)-1,3,4-oxazole, 2,5-bis(1-phenyl)-1,3,4-thiazole, 2,5-bis(1-phenyl)-1,3,4-oxadiazole, 2-(4'-tert-butylphenyl)-5-(4'-biphenyl)1,3,4-oxadiazole, 2,5-bis(1-naphthyl)-1,3,4-oxadiazole, 1,4-bis[2-(5-phenylthiadiazolyl)]benzene, 2,5-bis(1-naphthyl)-1,3,4-triazole, and 3-(4-biphenylyl)-4-phenyl-5-(4-t-butylphenyl)-1,2,4-triazole. In addition, a polymer material used in a polymer organic luminescence element may also be used. Examples of the polymer material include, but not limited to, polypara-phenylene and derivatives thereof, and fluorene and derivatives thereof.

Meanwhile, as for the material to be used as the hole-transport layer (hereinafter, referred to as "hole-transport material"), any material may be selected from known materials and used as the hole-transport material. Examples of the hole-transport material include, but not limited to, aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl (α-NPD), stilbene derivatives, pyrazoline derivatives, polyarylalkanes, 4,4',4'-tris(N-(3-methylphenyl)N-phenylamino)triphenylamine (m-MTDATA), 2,2',7,7'-tetrakis-(N,N-diphenylamino)-9,9'-spirobifluorene, and polymer materials such as polyvinyl carbazole.

In the organic EL element, a buffer layer may be formed between the hole-transport layer and the anode so as to enhance the hole-injection performance. Any material, which may be selected from known materials, may be used as the material to be used in the buffer layer. The above-mentioned hole-transport material doped with 1 wt % to 30 wt % of molybdenum oxide may be more preferably used as the material to be used in the buffer layer, although the material is not limited thereto.

Examples of the conductive material to be used for the anode include materials having a work function of more than about 4 eV, including carbon atom, aluminum, vanadium, iron, cobalt, nickel, tungsten, silver, gold, platinum, palladium and alloys thereof, metal oxides such as tin oxide and indium oxide, which are used in an ITO (indium oxide doped with 5% to 10% of tin oxide) substrate or an NESA substrate, and organic conductive resins such as polythiophene and polypyrrole. It is preferred, however, that the conductive material used for the anode has a higher work function than the conductive material used for the cathode of the element by 0.1 eV or more.

Examples of the conductive material to be used for the cathode include materials having a work function of less than about 4 eV, including magnesium, calcium, tin, lead, titanium, yttrium, lithium, ruthenium, manganese and aluminum, and alloys thereof. Examples of the alloy as used herein include magnesium/silver, magnesium/indium, and lithium/aluminum. The composition ratio of the alloy may be controlled by the temperature of the source for vapor deposition, the atmosphere, the degree of vacuum, and the like, and the composition ratio is not limited. It is preferred, however, that the conductive material used for the cathode has a lower work function than the conductive material used for the anode of the element by 0.1 eV or more.

The anode and the cathode may be formed of two or more layers as the layer construction, if necessary.

In the organic EL element of the present invention, an electron-injection layer may be formed between the electron-transport layer and the cathode so as to enhance the electron-injection performance. Examples of the material to be used in the electron-injection layer include, but not limited to, alkali metal fluorides such as LiF; alkali earth metal fluorides such as $BaF_2$ and $SrF_2$; alkali metal oxides such as $Li_2O$; and alkali earth metal oxides such as RaO and SrO.

At least one side of the organic EL element of the present invention may be preferably transparent over the range of luminescence wavelength emitted by the element. In addition, the substrate may also be preferably transparent.

The transparent electrode may be formed, for example, by vapor deposition, sputtering, or the like, using the conductive material, while setting the conditions to achieve a desired transparency.

The electrode on the luminescent surface may preferably have a light transmittance of 10% or more.

The substrate is not limited as long as it has adequate mechanical and thermal strength, and transparency. A glass substrate, or a transparent resin film may be preferably used.

Examples of the transparent resin film include polyethylene, ethylene-vinyl acetate copolymer, ethylene-vinyl alcohol copolymer, polypropylene, polystyrene, polymethyl methacrylate, polyvinyl chloride, polyvinyl alcohol, polyvinyl butyral, nylon, polyether ether ketone, polysulfone, polyether sulfone, tetrafluoroethylene-perfluoroalkyl vinyl ether copolymer, polyvinyl fluoride, tetrafluoroethylene-ethylene copolymer, tetrafluoroethylene-hexafluoropropylene copolymer, polychlorotrifluoroethylene, polyvinylidene fluoride, polyester, polycarbonate, polyurethane, polyimide, polyetherimide, polyimide, and polypropylene.

In order to enhance the stability against the temperature, the humidity, the atmosphere, and the like, a protective layer may be formed on the surface of the organic EL element of the present invention, or the entire element may be protected by silicone oil, a resin, or the like.

In addition, each layer of the organic EL element may be formed by applying either a dry film-forming method such as vapor deposition, sputtering, plasma and ion plating, or a wet film-forming method such as spin coating, dipping and flow coating. The thickness of each layer may be preferably, but not limited to, from 0.1 nm to 10 μm, more preferably from 0.5 nm to 0.2 μm.

In the case of the wet film-forming method, a thin film may be provided (film-formed), using a composition prepared by dissolving or dispersing the material(s) used for each layer in a solvent such as ethanol, chloroform, tetrahydrofuran, dioxane, toluene, chlorobenzene and ion-exchanged water.

EXAMPLES

The present invention will be more specifically described below with reference to the Examples. However, the scope of the present invention should not be limited to these Examples.

Reference Example 1

Synthesis of (di-μ-chloro-tetrakis(2-phenylpyridinato)diiridium(III))

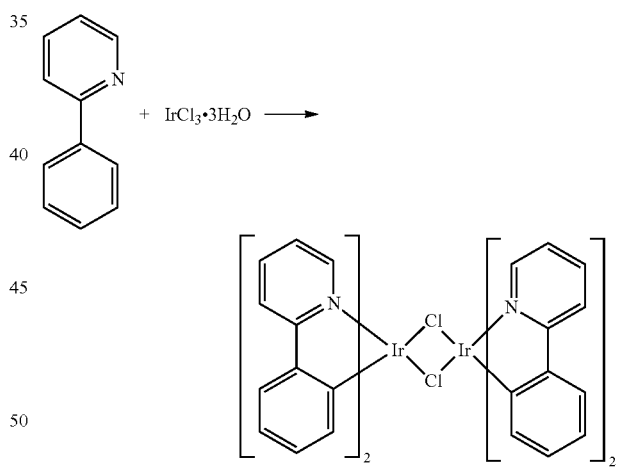

Into a 300 mL two-necked glass flask equipped with a thermometer, a reflux condenser and a stirrer were placed 5.10 g (32.9 mmol) of 2-phenylpyridine and 164 ml of 2-ethoxyethanol. Subsequently, the resultant mixture solution was purged with argon. And then, 4.63 g (13.2 mmol) of iridium trichloride tri-hydrate was added to the mixture solution, and the mixture was reacted under stirring at 120-130° C. for 22 hours. After the completion of the reaction, the reaction liquid was cooled to room temperature, and 25 ml of deionized water was added to the reaction liquid, and then a saturated aqueous solution of sodium hydrogen carbonate was added thereto. And then, the precipitate was collected by filtration, and washed with 60 ml of 2-ethoxyethanol/deionized water (volume ratio; 3/1), and then dried, to provide 3.77 g of di-μ-chloro-tetrakis(2-phenylpyridinato) diiridium(III) as a yellow solid. (Isolation yield: 53%)

Additionally, di-μ-chloro-tetrakis(2-phenylpyridinato)diiridium(III) had the following properties:

$^1$H-NMR (400 MHz, CD$_2$Cl$_2$, δ (ppm)); 9.25 (m, 4H), 7.93 (d, 4H), 7.79 (m, 4H), 7.55 (dd, 4H), 6.90-6.74 (m, 8H), 6.60 (m, 4H), 5.87 (dd, 4H)

FAB-MS (M/Z); 536 (M/2)$^+$, 501, 499

Example 1

Synthesis of (chloro-bis(2-phenylpyridinato)(2-pyrazolyl)iridium(III))

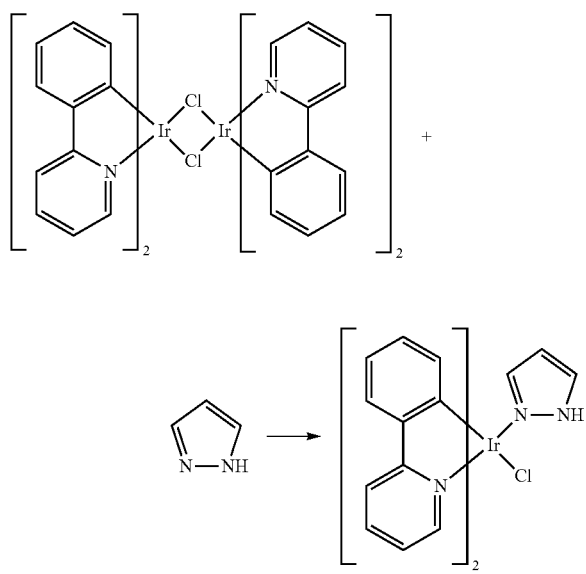

Under argon atmosphere, into a 25 mL Schlenk flask equipped with a stirrer were placed 161 mg (0.15 mmol) of di-μ-chloro-tetrakis(2-phenylpyridinato)diiridium(III), 20.4 mg (0.30 mmol) of pyrazole and 10 ml of tetrahydrofuran. And then, the mixture was reacted under stirring at room temperature for 13 hours. After the completion of the reaction, tetrahydrofuran was distilled off under reduced pressure, and methylene chloride was added to the residue. After the insoluble substance was removed by filtration with Celite, the filtrate was distilled under reduced pressure. The resultant crude reaction product was washed with hexane, to provide 148 mg of the desired compound as a yellow solid. (Isolation yield: 82%)

Additionally, chloro-bis(2-phenylpyridinato)(2-pyrazolyl)iridium(III) was a novel compound, which had the following properties:

$^1$H-NMR (400 MHz, CD$_2$Cl$_2$, δ (ppm)); 13.05 (s, 1H), 9.73 (d, 1H), 7.91-7.89 (m, 1H), 7.84-7.82 (m, 1H), 7.78-7.70 (m, 3H), 7.65-7.64 (m, 1H), 7.61-7.59 (m, 2H), 7.20-7.17 (m, 1H), 7.06-7.02 (m, 1H), 6.95-6.91 (m, 1H), 6.88-6.84 (m, 1H), 6.80-6.73 (m, 2H), 6.70-6.69 (m, 1H), 6.33-6.30 (dd, 1H), 6.23-6.20 (m, 2H)

FAB-MS (M/Z); 605 (M+H)$^+$

Example 2

Synthesis of (tetrakis(2-phenylpyridinato)bis(μ-pyrazolato)diiridium(III), Abbreviation; [Ir(PPy)$_2$Pz]$_2$)

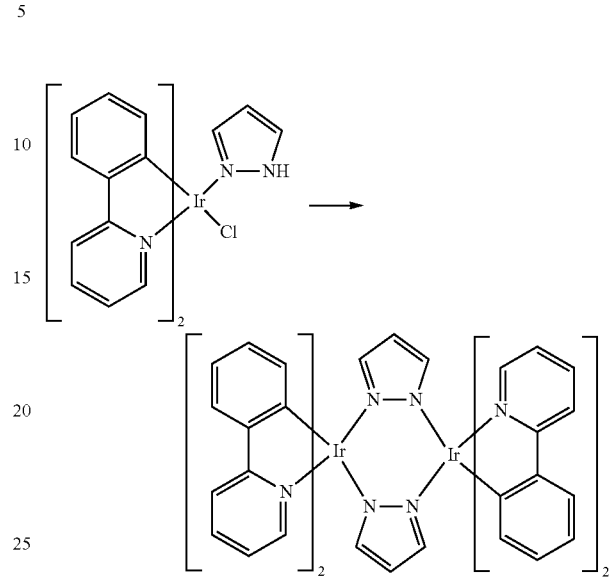

Under argon atmosphere, into a 50 mL Schlenk flask equipped with a stirrer were placed 302 mg (0.50 mmol) of chloro-bis(2-phenylpyridinato)(2-pyrazolyl)iridium(III), which was prepared in the same way as in Example 1, 69 mg (0.53 mmol) of tert-butoxy potassium (t-BuOK (85 wt % product)) and 25 ml of tetrahydrofuran. And then, the mixture was reacted under stirring at room temperature for 13 hours. After the completion of the reaction, tetrahydrofuran was distilled off under reduced pressure, and methylene chloride was added to the residue. After the insoluble substance was removed by filtration, the filtrate was distilled under reduced pressure. The resultant crude reaction product was subjected to column chromatography with silica gel (developing solvent: methylene chloride) for purification, and then the resultant solid was recrystallized with toluene, to provide 74 mg of the desired compound as a yellow solid. (Isolation Yield: 26%)

Additionally, tetrakis(2-phenylpyridinato)bis(μ-pyrazolato) diiridium(III) was a novel compound, which had the following properties:

$^1$H-NMR (400 MHz, CD$_2$Cl$_2$, δ (ppm)); 8.22 (m, 2H), 7.95 (d, 2H), 7.78 (d, 2H), 7.65-7.58 (m, 7H), 7.52-7.48 (m, 2H), 6.86-6.53 (m, 16H), 6.41-6.37 (m, 2H), 6.12-6.10 (m, 2H), 6.03-6.01 (m, 2H), 5.91-5.90 (m, 1H)

FAB-MS (M/Z): 1136 (M+H)$^+$

The Examples will be described in which an organic electroluminescence element was produced using the iridium compound of the present invention [Ir(PPy)$_2$Pz]$_2$ (iridium complex prepared in Example 2).

Example 3

Production of Organic EL Element Comprising the Iridium Complex of the Present Invention An organic EL element comprising a glass substrate 1, an ITO transparent electrode 2, a hole-transport layer 3, a luminescent layer 4, an electron-transport layer 5, an electron-injection layer 6 and an aluminum electrode 7, which were formed on the substrate in that order as illustrated in FIG. 1, was produced by the following process.

A glass with a film of indium tin oxide (hereinafter, abbreviated as "ITO") made by EHC Co., Ltd. was used as a transparent electrode/substrate. A hole-transport layer 3, a luminescent layer 4, an electron-transport layer 5, an electron-injection layer 6 and an aluminum electrode 7 were formed on the substrate in that order by vapor deposition at a vacuum of $5 \times 10^{-4}$ Pa or less, using a vacuum vapor deposition apparatus made by ULVAC KIKO, Inc., to provide an organic EL element as follows.

The vapor deposition was performed by placing the raw material(s) in a crucible, which was placed opposite to the substrate, and heating the material(s) together with the crucible.

A film of 1,1-bis[4-[N,N-di(p-tolyl)amino]phenyl]cyclohexane (hereinafter, abbreviated as "TAPC") as a hole-transport material, which had a thickness of 73 nm, was formed on the substrate, to form a hole-transport layer 3. Subsequently, a film of 9,9'-(2,2'-dimethyl-[1,1'-biphenyl]-4,4'-diyl)bis (9H-carbazole) (hereinafter, abbreviated as "CDBP"): [Ir $(PPy)_2Pz]_2$ (prepared in the same way as in Example 2)=95:5, which had a thickness of 49 nm, was formed thereon as a luminescent layer 4. And then, a film of 3-(4-biphenylyl)-4-phenyl-5-t-butylphenyl-1,2,4-triazole (hereinafter, abbreviated as "TAZ"), which had a thickness of 19 nm, was formed thereon, to form an electron-transport layer 5. Furthermore, a film of lithium fluoride (hereinafter, abbreviated as "LiF"), which had a thickness of 0.5 nm, was formed on the electron-transport layer, to form an electron-injection layer 6. And then, a film of aluminum (Al), which had a thickness of 240 nm, was formed thereon, to form an electrode 7.

The layer construction of the element was briefly described as follows.
Anode 2: ITO (130 nm),
Hole-transport layer 3: TAPC (73 nm),
Luminescent layer 4: CDBP [Ir(PPy)$_2$Pz]$_2$ (49 nm, 95/5),
Electron-transport layer 5: TAZ (19 nm),
Electron-injection layer 6: LiF (0.5 nm),
Cathode 7: Al (240 nm).

The element was energized using the ITO electrode 2 as the anode and the Al electrode 7 as the cathode. When the voltage between the electrodes was increased, the element began to emit green light, which was clearly visible to the naked eye, around +10 V and emitted light with a luminance of 14650 cd/m$^2$ at +24 V.

The current efficiency with respect to the emission of light of the element was calculated by the following formula:

Current Efficiency=(Luminance per unit area)/(Current density per unit area)

The current efficiency calculated in this way was 14.9 cd/A at +20 V.

The emission color of the element was determined, using an organic EL evaluation apparatus EL1003 made by PRECISE GAUGES Co., Ltd. The chromaticity coordinate, which was determined in accordance with JIS Z8701 from the spectrum measured at +24 V of the voltage between the electrodes, was x=0.399 and y=0.478 (by CIE (Commission Internationale de l'Eclairage) colorimetric system).

Reference Example 2

Production of Organic EL Element Comprising a Well-Known Iridium Complex

An organic EL element was produced in the same way as in Example 3, except that a well-known iridium complex, tris (2-phenylpyridinato) iridium(III) (Abbreviation; Ir(ppy)$_3$) was used instead of [Ir(PPy)$_2$Pz]$_2$ used for the luminescent layer in Example 3.

The element was energized using the ITO electrode 2 as the anode and the Al electrode 7 as the cathode. When the voltage between the electrodes was increased, the element began to emit green light, which was clearly visible to the naked eye, around +10 V and emitted light with a luminance of 14500 cd/m$^2$ at +24 V. The current efficiency was 14.8 cd/A at +20 V.

The chromaticity coordinate, which was determined in accordance with JIS 28701 from the spectrum measured at +24 V of the voltage between the electrodes, was x=0.359 and y=0.587 (by CIE (Commission Internationale de l'Eclairage) colorimetric system).

The above-mentioned results revealed that the binuclear metal complex (binuclear iridium complex) of the present invention shows high element performance comparable to the well-known iridium compound.

Reference Example 3

Synthesis of (di-µ-chloro-tetrakis(2-(2,4-difluorophenyl)pyridinato)diiridium(III))

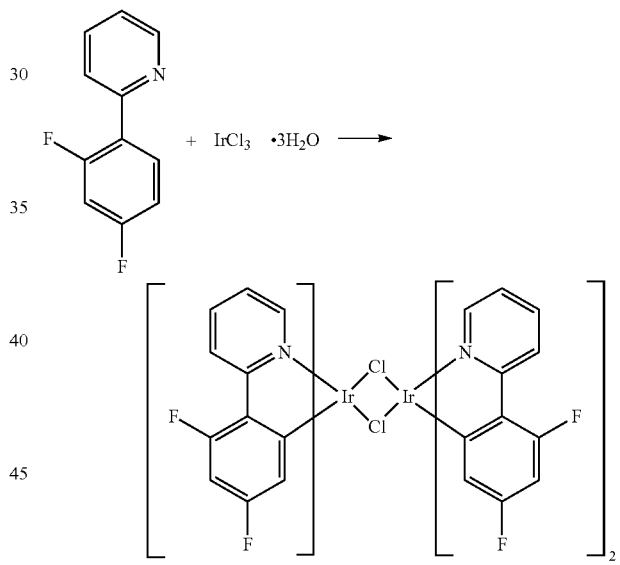

Into a 300 mL two-necked glass flask equipped with a thermometer, a reflux condenser and a stirrer were placed 6.29 g (32.9 mmol) of 2-(2,4-difluorophenyl)pyridine and 164 ml of 2-ethoxyethanol. Subsequently, the resultant mixture solution was purged with argon. And then, 4.63 g (13.2 mmol) of iridium trichloride tri-hydrate was added to the mixture solution, and the mixture was reacted under stirring at 120-130° C. for 21 hours. After the completion of the reaction, the reaction liquid was cooled to room temperature, and 25 ml of deionized water was added to the reaction liquid, and then a saturated aqueous solution of sodium hydrogen carbonate was added thereto. And then, the precipitate was collected by filtration, and washed with 60 ml of 2-ethoxyethanol/deionized water (volume ratio; 3/1), and then dried, to provide 5.09 g of di-µ-chloro-tetrakis(2-(2,4-difluorophenyl)pyridinato)diiridium(III) as a yellow solid. (Isolation yield: 63%)

Additionally, di-μ-chloro-tetrakis(2-(2,4-difluorophenyl)pyridinato)diiridium(III) had the following properties:

$^1$H-NMR (400 MHz, CD$_2$Cl$_2$, δ (ppm)); 9.11 (m, 4H), 8.32 (d, 4H), 7.87 (m, 4H), 6.86 (m, 4H), 6.38 (m, 4H), 5.28 (m, 4H)

FAB-MS (M/Z); 608 (M/2), 573, 571

Example 4

Synthesis of (tetrakis(2-(2,4-difluorophenyl)pyridinato)(μ-biimidazolyl) diiridium(III), Abbreviation; [Ir(dfppy)$_2$BIm]$_2$)

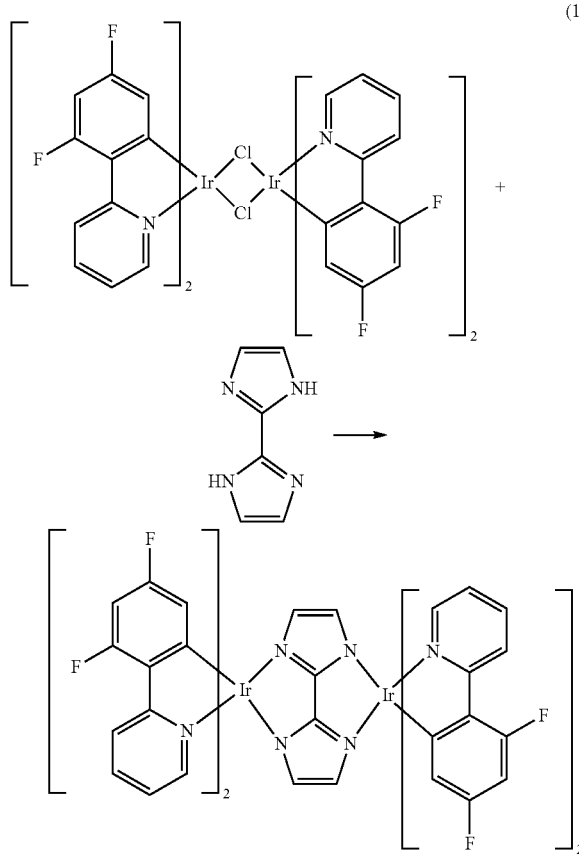

Under argon atmosphere, into a 250 mL Schlenk flask equipped with a stirrer were placed 486 mg (0.40 mmol) of di-μ-chloro-tetrakis(2-(2,4-difluorophenyl)pyridinato)diiridium(III), 54 mg (0.40 mmol) of 2,2'-biimidazole and 80 ml of tetrahydrofuran. And then, the mixture was stirred at room temperature for 1 hour. Subsequently, 111 mg (0.84 mmol) of tert-butoxy potassium (t-BuOK (85 wt % product)) was added to the mixture, and the mixture was reacted under stirring at room temperature for 2 hours. After the completion of the reaction, the reaction liquid was concentrated, and then methylene chloride, water and a saturated aqueous solution of ammonium chloride were added to the resultant concentrate until pH became 7, and the organic phase was separated from the water phase. The resultant organic phase was dried with sodium sulfate, and filtered, and then the filtrate was concentrated. And then, the resultant concentrate was washed with hexane, to provide 441 mg of binuclear iridium complex (1) as a yellow solid. (Isolation yield: 86%)

The obtained binuclear iridium complex (1) was a mixture of two different types of isomers, and the abundance ratio was 60:40. The binuclear iridium complex obtained as the main product (60%) was referred to as "binuclear iridium complex (1a)" and the binuclear iridium complex obtained as the secondary product (40%) was referred to as "binuclear iridium complex (1b)".

Additionally, the binuclear iridium complex (1) was a novel compound, which had the following properties:

$^1$ H-NMR (400 MHz, C$_4$D$_8$O, δ (ppm));

Binuclear iridium complex (1a); 8.17 (d, 4H), 8.13-8.12 (m, 4H), 7.79-7.75 (m, 4H), 7.91-7.15 (m, 4H), 6.49-6.42 (m, 4H), 6.22 (s, 4H), 5.84-5.81 (m, 4H)

Binuclear iridium complex (1b); 8.24 (d, 4H), 7.85-7.81 (m, 4H), 7.74-7.72 (m, 4H), 6.95-6.91 (m, 4H), 6.49-6.42 (m, 4H), 6.24 (s, 4H), 5.77-5.74 (m, 4H)

FD-MS (MIZ): 1276 (M$^+$)

The Examples will be described in which an organic electroluminescence element was produced using the binuclear iridium complex (1) of the present invention (iridium complex prepared in Example 4).

Example 5

Production of Organic EL Element Comprising the Binuclear Iridium Complex of the Present Invention An organic EL element comprising a glass substrate 1, an ITO transparent electrode 2, a hole-transport layer 3, a luminescent layer 4, an electron-transport layer 5, an electron-injection layer 6 and an aluminum electrode 7, which were formed on the substrate in that order as illustrated in FIG. 1, was produced by the following process.

A glass with a film of indium tin oxide (hereinafter, abbreviated as "ITO") made by EHC Co., Ltd. was used as a transparent electrode/substrate. A hole-transport layer 3, a luminescent layer 4, an electron-transport layer 5, an electron-injection layer 6 and an aluminum electrode 7 were formed on the substrate in that order by vapor deposition at a vacuum of 5×10$^{-4}$ Pa or less, using a vacuum vapor deposition apparatus made by ULVAC KIKO, Inc., to provide an organic EL element as follows.

The vapor deposition was performed by placing the raw material(s) in a crucible, which was placed opposite to the substrate, and heating the material(s) together with the crucible.

A film of p,p'-[N,N'-tetra(p-toluyl)dianilino-o,o'biphenyl] (hereinafter, abbreviated as "3DTAPBP") as a hole-transport material, which had a thickness of 60 nm, was formed on the substrate, to form a hole-transport layer 3. Subsequently, a film of triphenyl(4-(9-phenyl-9H-fluorene-9-yl)phenyl)silane (hereinafter, abbreviated as "TPSiF") binuclear iridium complex (1) (prepared in the same way as in Example 4)=95: 5, which had a thickness of 40 nm, was formed thereon as a luminescent layer 4. And then, a film of 3-(4-biphenylyl)-4-phenyl-5-t-butylphenyl-1,2,4-triazole (hereinafter, abbreviated as "TAZ"), which had a thickness of 40 nm, was formed thereon, to form an electron-transport layer 5. Furthermore, a film of lithium fluoride (hereinafter, abbreviated as "LiF"), which had a thickness of 0.5 nm, was formed on the electron-transport layer, to form an electron-injection layer 6. And then, a film of aluminum (Al), which had a thickness of 100 nm, was formed thereon, to form an electrode 7.

The layer construction of the element was briefly described as follows.

Anode 2: ITO (130 nm),
Hole-transport layer 3: 3DTAPBP (60 nm),
Luminescent layer 4: TPSiF: binuclear iridium complex (1) (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +15 V and emitted light with a luminance of 872.3 cd/m$^2$ at +30 V. The current efficiency was 1.88 cd/A at +24 V.

The emission color of the element was determined, using an organic EL evaluation apparatus EL1003 made by PRECISE GAUGES Co., Ltd. The chromaticity coordinate, which was determined in accordance with JIS Z8701 from the spectrum measured at +20 V of the voltage between the electrodes, was x=0.249 and y=0.200 (by CIE (Commission Internationale de l'Eclairage) colorimetric system).

Reference Example 4

Production of Organic EL Element Comprising a Well-Known Iridium Complex

An organic EL element was produced in the same way as in Example 5, except that a well-known iridium complex, bis(2-(2,4-difluorophenyl)pyridinato)picolinato iridium(III) (Abbreviation; FIrpic) was used instead of the binuclear iridium complex (1) used for the luminescent layer in Example 5.

The element was energized using the ITO electrode 2 as the anode and the Al electrode 7 as the cathode. When the voltage between the electrodes was increased, the element began to emit light-blue light, which was clearly visible to the naked eye, around +17 V and emitted light with a luminance of 480.8 cd/m$^2$ at +27 V. The current efficiency was 2.16 cd/A at +24 V.

The chromaticity coordinate, which was determined in accordance with JIS Z8701 from the spectrum measured at +20 V of the voltage between the electrodes, was x=0.280 and y=0.293 (by CIE (Commission Internationale de l'Eclairage) colorimetric system).

The above-mentioned results revealed that the binuclear metal complex (binuclear iridium complex) of the present invention shows high element performance comparable to the well-known iridium compound.

Reference Example 5

Synthesis of (di-μ-chloro-tetrakis(2',6'-difluoro-2,3'-bipyridinato)diiridium(III))

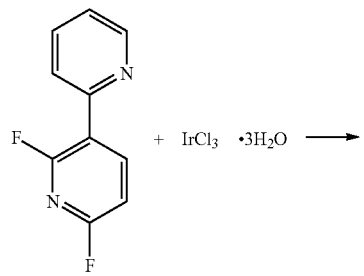

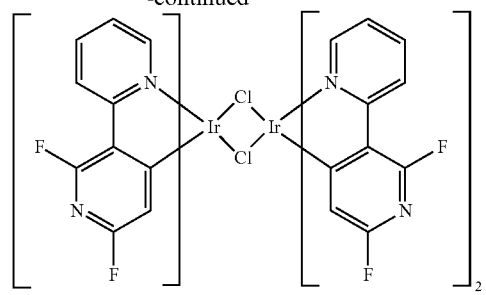

Into a 100 mL two-necked glass flask equipped with a thermometer, a reflux condenser and a stirrer were placed 2.80 g (14.6 mmol) of 2',6'-difluoro-2,3'-bipyridine and 73 ml of 2-ethoxyethanol. Subsequently, the resultant mixture solution was purged with argon. And then, 2.07 g (5.84 mmol) of iridium trichloride tri-hydrate was added to the mixture solution, and the mixture was reacted under stirring at 120-130° C. for 20 hours. After the completion of the reaction, the reaction liquid was cooled to room temperature, and 25 ml of deionized water was added to the reaction liquid, and then a saturated aqueous solution of sodium hydrogen carbonate was added thereto. And then, the precipitate was collected by filtration, and washed with 10 ml of 2-ethoxyethanol/deionized water (volume ratio; 3/1), and then dried, to provide 1.75 g of di-μ-chloro-tetrakis(2',6'-difluoro-2,3'-bipyridinato)diiridium(III) as a yellow solid. (Isolation yield: 49%)

Additionally, di-μ-chloro-tetrakis(2',6'-difluoro-2,3'-bipyridinato)diiridium(III) had the following properties:

$^1$H-NMR (400 MHz, CD$_2$Cl$_2$, δ (ppm)); 9.06 (m, 4H), 8.34 (m, 4H), 8.00 (m, 4H), 6.98 (m, 4H), 5.27 (m, 4H)

FAB-MS (M/Z); 1221 (M+H)$^+$, 610, 575

Reference Example 6

Synthesis of (di-μ-chloro-tetrakis(3-methyl-1-phenylimidazoline-2-ylidene)diiridium(III))

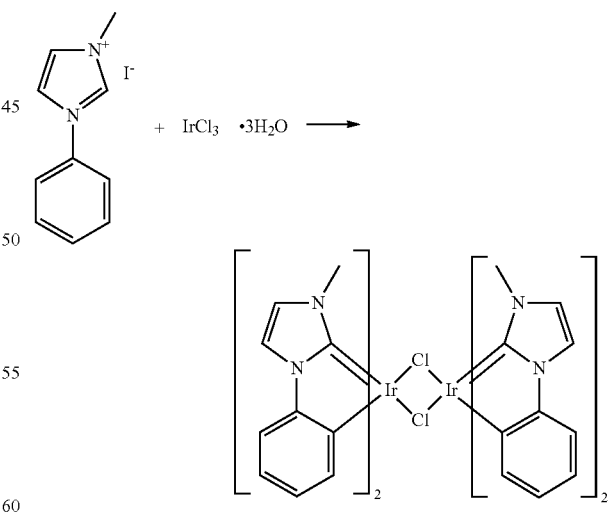

Into a 300 mL four-necked glass flask equipped with a thermometer, a reflux condenser and a stirrer were placed 2.82 g (9.84 mmol) of N-methyl-N'-phenyl imidazolium iodide and 180 ml of 2-ethoxyethanol. Subsequently, the resultant mixture solution was purged with argon. And then, after the flask was covered with an aluminum foil, 1.06 g (3.00 mmol) of iridium trichloride tri-hydrate and 1.27 g (5.49 mmol) of silver oxide were added to the mixture solution, and the mixture was reacted under stirring at 120-130° C. for 16 hours. After the completion of the reaction, the reaction liquid was cooled to room temperature, and then the solvent was removed from the reaction liquid. The desired compound was extracted with 100 ml of methylene chloride from the resultant solid, and then the solvent was removed from the mixture. Subsequently, 3 ml of methylene chloride and 20 ml of methanol were added to the resultant solid, and then the resultant mixture was filtered because a white solid was precipitated. And then, the filtrate was concentrated, and methanol was added to the resultant concentrate again, and then the resultant mixture was filtered because a white solid was precipitated. These precipitates were dried, to provide 216 mg of di-μ-chloro-tetrakis(3-methyl-1-phenylimidazoline-2-ylidene) diiridium(III) as a white solid. (Isolation yield: 7%)

Additionally, di-μ-chloro-tetrakis(3-methyl-1-phenylimidazoline-2ylidene)diiridium(III) had the following properties:

$^1$H-NMR (400 MHz, CD$_2$Cl$_2$, δ (ppm)); 7.58 (d, 4H), 7.16 (d, 4H), 6.98 (dd, 4H), 6.72 (dt, 4H), 6.44 (dt, 4H), 6.09 (dd, 4H), 3.91 (s, 12H)

Reference Example 7

Synthesis of (di-μ-chloro-tetrakis(1-phenylpyrazolato)diiridium(III))

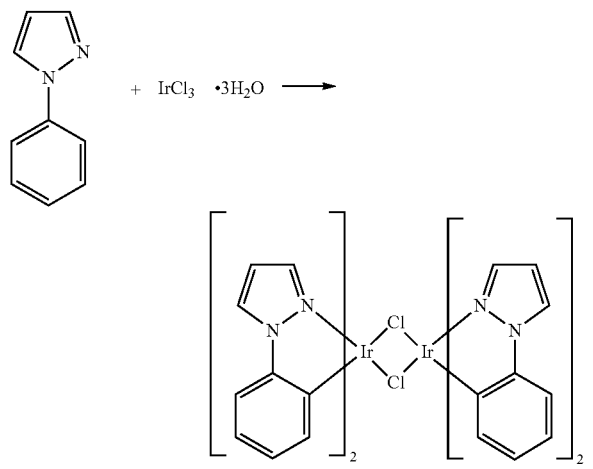

Into a 200 mL two-necked glass flask equipped with a thermometer, a reflux condenser and a stirrer were placed 2.81 g (19.5 mmol) of 1-phenylpyrazole, 100 ml of 2-ethoxyethanol and 33 ml of deionized water. Subsequently, the resultant mixture solution was purged with argon. And then, 2.64 g (7.80 mmol) of iridium trichloride tri-hydrate was added to the mixture solution, and the mixture was reacted under stirring at 120-130° C. for 9 hours. After the completion of the reaction, the reaction liquid was cooled to room temperature, and a saturated aqueous solution of sodium hydrogen carbonate was added to the reaction liquid. And then, the precipitate was collected by filtration, and washed with 26 ml of 2-ethoxyethanol/deionized water (volume ratio; 3/1), and then dried, to provide 3.44 g of di-μ-chloro-tetrakis(1-phenylpyrazolato)diiridium(III) as a pale yellow solid. (Isolation yield: 86%)

Additionally, di-μ-chloro-tetrakis(1-phenylpyrazolato) had the following properties:

$^1$H-NMR (400 MHz, CD$_2$Cl$_2$, δ (ppm)); 8.19 (m, 4H), 7.82 (m, 4H), 7.19 (m, 4H), 6.84 (m, 4H), 6.68 (m, 4H), 6.53 (m, 4H), 5.94 (m, 4H)

FAB-MS (M/Z); 1028 (M+H)$^+$, 519, 479

Reference Example 8

Synthesis of (di-μ-chloro-tetrakis(1-methyl-2-phenylimidazolato)diiridium(III))

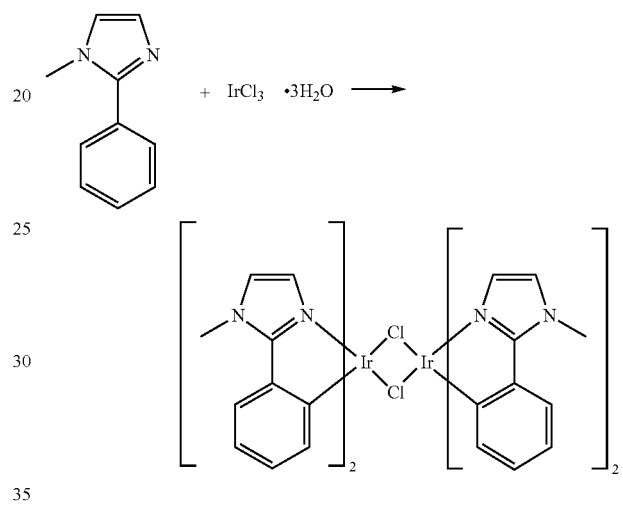

Into a 200 mL two-necked glass flask equipped with a thermometer, a reflux condenser and a stirrer were placed 3.28 g (20.7 mmol) of 1-methyl-2-phenylimidazole and 100 ml of 2-ethoxyethanol. Subsequently, the resultant mixture solution was purged with argon. And then, 3.0 g (8.3 mmol) of iridium trichloride tri-hydrate was added to the mixture solution, and the mixture was reacted under stirring at 120-130° C. for 21 hours. After the completion of the reaction, the reaction liquid was cooled to room temperature, and 100 ml of deionized water was added to the reaction liquid, and then a saturated aqueous solution of sodium hydrogen carbonate was added thereto. And then, the precipitate was collected by filtration, and washed with 20 ml of 2-ethoxyethanol/deionized water (volume ratio; 1/1), and then dried, to provide a black solid. Subsequently, 300 ml of methylene chloride was added to the resultant black solid, and the mixture was stirred. And then, the precipitate was collected by filtration, and washed with 200 ml of methylene chloride. The filtrate and the washings obtained were concentrated under reduced pressure. The resultant crude product was washed with 5 ml of methylene chloride, to provide 1.69 g of di-μ-chloro-tetrakis(1-methyl-2-phenylimidazolato)diiridium(III) as a yellowish green solid. (Isolation yield: 37%)

Additionally, di-μ-chloro-tetrakis(1-methyl-2-phenylimidazolato)diiridium(III) had the following properties:

$^1$H-NMR (400 MHz, CD$_2$Cl$_2$, δ (ppm)); 7.37 (m, 4H), 7.27 (d, 4H), 6.93 (d, 4H), 6.74 (dd, 4H), 6.54 (dd, 4H), 6.05 (dd, 4H), 4.05 (s, 12H)

FAB-MS (M/Z); 542 (M/2)$^+$, 1083, 1085 (M+1)

Example 6

Synthesis of (chloro-bis(1-methyl-2-phenylimidazolato)(2-pyrazolyl)iridium(III)

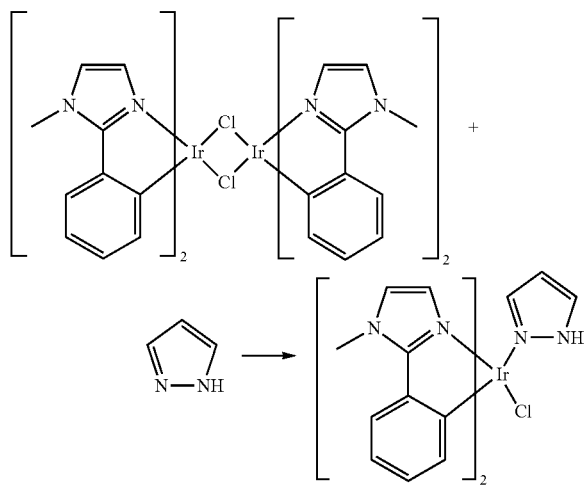

Under argon atmosphere, into a 25 mL Schlenk flask equipped with a stirrer were placed 109 mg (0.10 mmol) of di-μ-chloro-tetrakis(1-methyl-2-phenylimidazolato)diiridium(III), 13.6 mg (0.20 mmol) of pyrazole and 7 ml of methylene chloride. And then, the mixture was reacted under stirring at room temperature for 28 hours. After the completion of the reaction, methylene chloride was distilled off under reduced pressure, and tetrahydrofuran was added to the residue, and then the resultant mixture was filtered. The resultant crude reaction product was washed with tetrahydrofuran, to provide 106 mg of the desired compound as a yellowish green solid. (Isolation yield: 86%)

Additionally, chloro-bis(1-methyl-2-phenylimidazolato) (2-pyrazolyl)iridium(III) was a novel compound, which had the following properties:

$^1$H-NMR (400 MHz, $CD_2Cl_2$, δ (ppm)); 13.5 (brs, 1H), 7.60 (m, 1H), 7.56 (d, 1H), 7.43 (m, 2H), 6.96 (m, 1H), 6.90-6.77 (m, 4H), 6.72 (m, 2H), 6.43 (dd, 1H), 6.37 (dd, 1H), 6.33 (d, 1H), 6.20 (m, 4.05 (s, 6H)

FAB-MS (MO; 611 (M+H)$^+$

Example 7

Synthesis of (chloro-bis(2',6'-difluoro-2,3'-bipyridinato)(2-pyrazolyl)iridium(III))

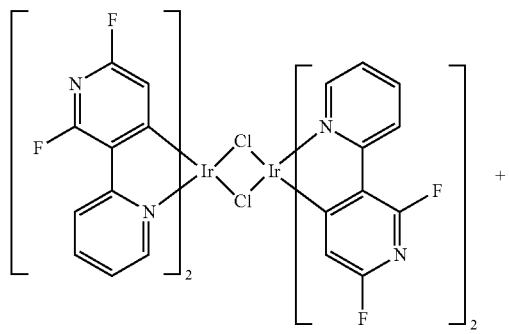

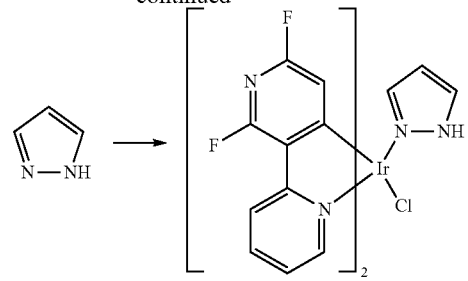

Under argon atmosphere, into a 50 mL Schlenk flask equipped with a stirrer were placed 244 mg (0.2 mmol) of di-μ-chloro-tetrakis(2',6'-difluoro-2,3'-bipyridinato)diiridium(III), 27.2 mg (0.40 mmol) of pyrazole and 20 ml of tetrahydrofuran. Subsequently, the mixture was reacted under stirring at room temperature for 14 hours, and then tetrahydrofuran was distilled off under reduced pressure. The resultant crude reaction product was washed with hexane, to provide 252 mg of the desired compound as a pale yellow solid. (Yield: 93%)

Additionally, chloro-bis(2',6'-difluoro-2,3'-bipyridinato) (2-pyrazolyl)iridium(III) was a novel compound, which had the following properties:

$^1$H-NMR (400 MHz, $CD_2Cl_2$, δ (ppm); 12.89 (s, 1H), 9.74-9.72 (m, 11-1), 8.30-8.28 (m, 1H), 8.22-8.20 (m, 1H), 7.94-7.87 (m, 2H), 7.71-7.69 (m, 2H), 7.36-7.32 (m, 1H) 7.21-7.18 (m, 1H), 6.84-6.83 (m, 1H), 6.34-6.32 (m, 1H), 5.79-6.78 (m, 1H), 5.63-5.62 (m, 1H)

FAB-MS (M/Z): 679 (M+H)$^+$

Example 8

Synthesis of (chloro-bis(3-methyl-1-phenylimidazoline-2-ylidene)(2-pyrazolyl)irridium(III))

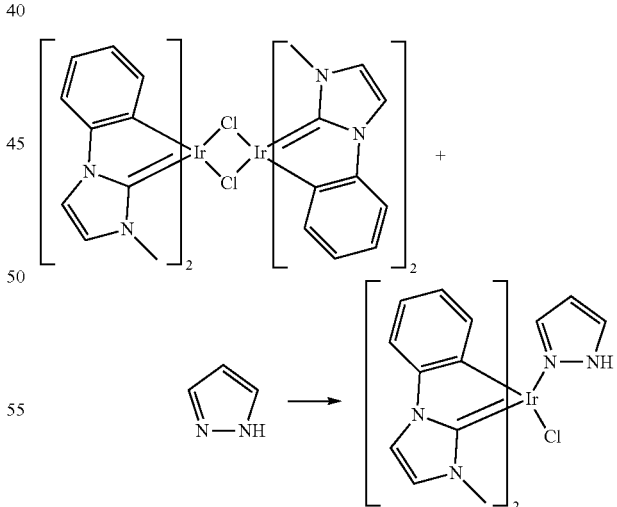

Under argon atmosphere, into a 30 mL Schlenk flask equipped with a stirrer were placed 163 mg (0.15 mmol) of di-μ-chloro-tetrakis(3-methyl-1-phenylimidazoline-2-ylidene) diiridium(III), 20.4 mg (0.30 mmol) of pyrazole and 15 ml of tetrahydrofuran. And then, the mixture was reacted under stirring at room temperature for 5 hours. After the completion of the reaction, tetrahydrofuran was distilled off under reduced pressure, and methylene chloride was added to the residue. After the insoluble substance was removed by filtration, the filtrate was distilled under reduced pressure. The resultant crude reaction product was washed with hexane, to provide 171 mg of the desired compound as a pale brown solid. (Yield: 93%)

Additionally, chloro-bis(3-methyl-1-phenylimidazoline-2-ylidene)(2-pyrazolyl)iridium(III) was a novel compound, which had the following properties:

$^1$H-NMR (400 MHz, CDCl$_3$, δ (ppm); 13.13 (s, 1H), 7.53-7.52 (m, 1H), 7.43-7.40 (m, 2H), 7.02-6.95 (m, 3H), 6.89 (d, 1H), 6.84-6.78 (m, 1H), 6.76-6.71 (m, 1H), 6.64 (s, 1H), 6.60-6.54 (m, 2H), 644-6.37 (m, 2H), 6.15-6.13 (m, 1H), 4.28 (s, 3H), 3.13 (s, 3H)

FAB-MS (M/Z): 611 (M+H)$^+$

Example 9

Synthesis of (chloro-bis(1-phenylpyrazolato)(2-pyrazolyl)iridium(III))

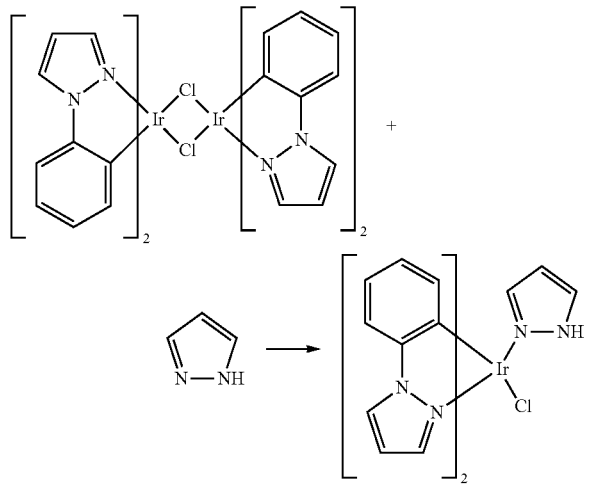

Under argon atmosphere, into a 50 mL Schlenk flask equipped with a stirrer were placed 206 mg (0.2 mmol) of di-μ-chloro-tetrakis(1-phenylpyrazolato)diiridium(III), 27.2 mg (0.4 mmol) of pyrazole and 20 ml of tetrahydrofuran. And then, the mixture was reacted under stirring at room temperature for 5 hours. After the completion of the reaction, tetrahydrofuran was distilled off under reduced pressure. The resultant crude reaction product was washed with diethyl ether, to provide 205 mg of the desired compound as a white solid. (Isolation yield: 88%)

Additionally, chloro-bis(1-phenylpyrazolato)(2-pyrazolyl) iridium (III) was a novel compound, which had the following properties:

$^1$H-NMR (400 MHz, CD$_2$Cl$_2$, δ (ppm); 12.94 (s, 1H), 8.23-8.22 (m, 1H), 8.10-8.09 (m, 1H), 8.06-8.05 (m, 1H), 7.65-7.64 (m, 1H), 7.22-7.20 (m, 2H), 7.01 (m, 1H), 6.96-6.86 (m, 3H), 6.76-6.69 (m, 2H), 6.65-6.64 (m, 1H), 6.60-6.58 (m, 1H), 6.33-6.31 (m, 1H), 6.25-6.23 (m, 2H)

FAB-MS (M/Z): 583 (M+H)$^+$

Example 10

Synthesis of (chloro-bis(2-(2,4-difluorophenyl)pyridinato)(2-pyrazolyl)iridium(III))

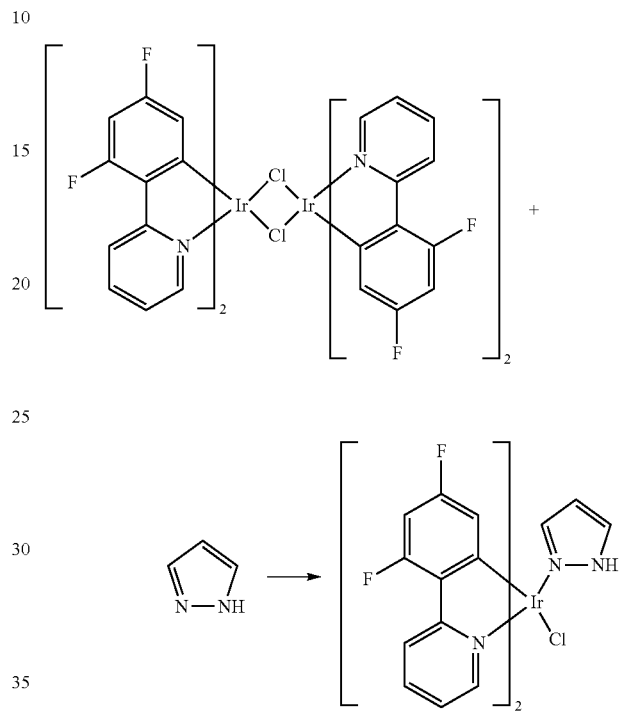

Under argon atmosphere, into a 50 mL Schlenk flask equipped with a stirrer were placed 243 mg (0.2 mmol) of di-μ-chloro-tetrakis(2-(2,4-difluorophenyl)pyridinato)diiridium(III), 27.2 mg (0.4 mmol) of pyrazole and 20 ml of tetrahydrofuran. And then, the mixture was reacted under stirring at room temperature for 5 hours. After the completion of the reaction, tetrahydrofuran was distilled off under reduced pressure, and methylene chloride was added to the residue. After the insoluble substance was removed by filtration, the filtrate was distilled under reduced pressure. The resultant crude reaction product was washed with hexane, to provide 230 mg of the desired compound as a yellow solid. (Isolation yield: 85%)

Additionally, chloro-bis(2-(2,4-difluorophenyl)pyridinato)(2-pyrazolyl)iridium(III) was a novel compound, which had the following properties:

$^1$H-NMR (400 MHz, CD$_2$Cl$_2$, δ (ppm); 12.96 (s, 1H), 9.74-9.72 (m, in), 8.29-8.27 (m, 1H), 8.21-8.18 (m, 1H), 7.82-7.78 (m, 2H), 7.69-7.66 (m, 2H), 7.25-7.21 (m, 1H), 7.10-7.07 (m, 1H), 6.78-6.77 (m, 1H), 6.51-6.45 (m, 1H), 6.41-6.35 (m, 1H), 6.29-6.27 (m, 1H), 5.80-5.78 (m, 1H), 5.66-5.63 (m, 1H)

FAB-MS (M/Z): 677 (M+H)$^+$

Example 11

Synthesis of (tetrakis(1-phenylpyrazolato)bis(μ-pyrazolato)diiridium(III), Abbreviation; [Ir(PPz)$_2$Pz]$_2$)

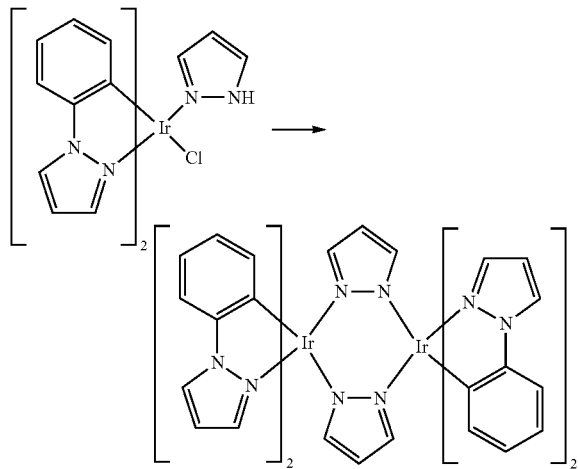

Under argon atmosphere, into a 100 mL Schlenk flask equipped with a stirrer were placed 378 mg (0.65 mmol) of chloro-bis(1-phenylpyrazolato)(2-pyrazolyl)iridium(III) and 33 ml of tetrahydrofuran. And then, the suspension was cooled to −78° C. with dry ice/ethanol, and then 90 mg (0.68 mmol) of tert-butoxy potassium (t-BuOK (85 wt % product)) was added to the suspension. Subsequently, the resultant mixture was warmed gradually, and then the mixture was reacted under stirring at −15° C. for 1 hour. After the completion of the reaction, tetrahydrofuran was distilled off under reduced pressure, and methylene chloride was added to the residue. After the insoluble substance was removed by filtration, the filtrate was distilled under reduced pressure. The resultant crude reaction product was subjected to column chromatography with silica gel (developing solvent: methylene chloride) for purification, and then the resultant solid was washed with ethyl acetate, to provide 224 mg of the desired compound as a white solid. (Isolation yield: 63%)

Additionally, tetrakis(1-phenylpyrazolato)bis(μ-pyrazolato)diiridium(III) was a novel compound, which had the following properties:

$^1$H-NMR (400 MHz, CD$_2$Cl$_2$, δ (ppm)); 8.04-8.03 (m, 4H), 7.26-7.23 (dd, 4H), 7.02 (d, 4H), 6.93-6.89 (m, 4H), 6.71-6.67 (m, 4H), 6.28-6.27 (m, 8H), 6.01-5.99 (dd, 4H), 5.82-5.81 (m, 2H)

FD-MS (M/Z): 1090 M$^+$

Example 12

Synthesis of (tetrakis(1-methyl-2-phenylimidazolato)bis(μ-pyrazolato)diiridium(III), Abbreviation; [Ir(PIm)$_2$Pz]$_2$)

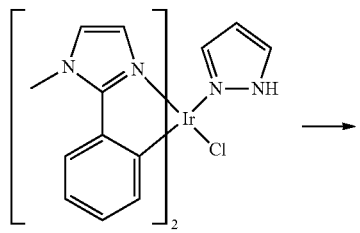

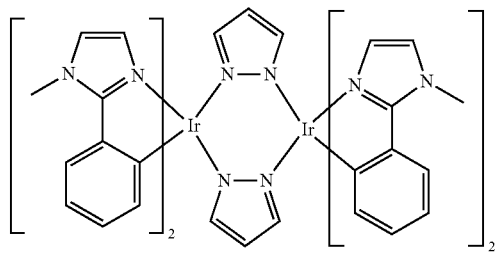

Under argon atmosphere, into a 50 mL Schlenk flask equipped with a stirrer were placed 61 mg (0.10 mmol) of chloro-bis(1-methyl-2-phenylimidazolato)(2-pyrazolyl)iridium(III), 13.2 mg (0.10 mmol) of tert-butoxy potassium (t-BuOK (85 wt % product)) and 10 ml of tetrahydrofuran. And then, the mixture was reacted under stirring at room temperature for 24 hours. After the completion of the reaction, the precipitate was collected by filtration, and washed with water and tetrahydrofuran, to provide 23 mg of the desired compound as a yellow solid. (Isolation yield: 37%)

Additionally, tetrakis(1-methyl-2-phenylimidazolato)bis(μ-pyrazolato)diiridium(III) was a novel compound, which had the following properties:

$^1$H-NMR (400 MHz, CD$_2$Cl$_2$, δ (ppm)); 7.45 (dd, 4H), 6.97 (d, 4H), 6.82 (m, 4H), 6.65 (m, 4H), 6.52 (d, 4H), 6.12 (dd, 4H), 5.73 (t, 2H), 5.64 (d, 4H), 5.28 (s, 12H)

FD-MS (M/Z): 1146, 1148

Example 13

Synthesis of (tetrakis(2',6'-difluoro-2,3'-bipyridinato)(μ-biimidazolyl)diiridium(III), Abbreviation; [Ir(df-pypy)$_2$BIm]$_2$)

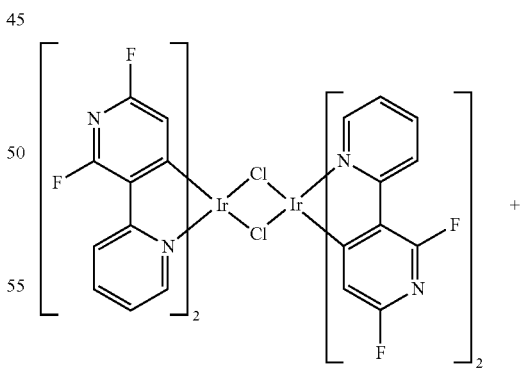

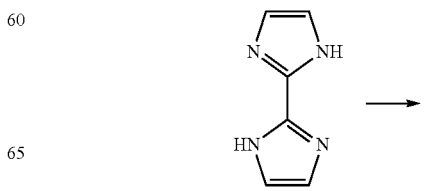

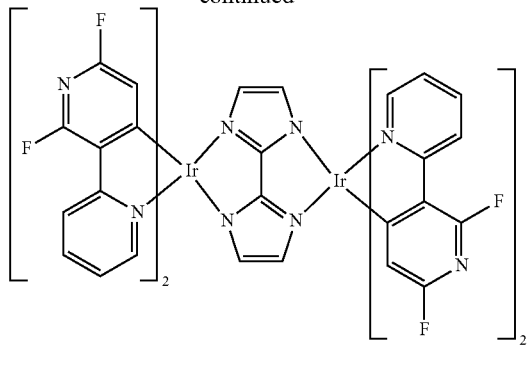

Under argon atmosphere, into a 100 mL Schlenk flask equipped with a stirrer were placed 366 mg (0.30 mmol) of di-μ-chloro-tetrakis(2',6'-difluoro-2,3'-bipyridinato)diiridium(III), 40 mg (0.30 mmol) of 2,2'-biimidazole and 60 ml of tetrahydrofuran. And then, the mixture was stirred at room temperature for 3.5 hours. Subsequently, 83 mg (0.63 mmol) of tert-butoxy potassium (t-BuOK (85 wt % product)) was added to the mixture, and the mixture was reacted under stirring at room temperature for 15 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride: 0.5% triethylamine) for purification, to provide 110 mg of the desired compound as a pale yellow solid. (Isolation yield: 28%)

Additionally, tetrakis(2',6'-difluoro-2,3'-bipyridinato)(μ-biimidazolyl)diiridium(III) was a novel compound, which had the following properties:

$^1$H-NMR (400 MHz, $CD_2Cl_2$, δ (ppm)); 8.27 (dd, 4H), 7.89-7.84 (m, 4H), 7.67 (m, 4H), 6.89-6.93 (m, 4H), 6.33 (s, 4H), 5.78 (t, 4H)

Example 14

Synthesis of (tetrakis(1-phenylpyrazolato)(μ-biimidazolyl)diiridium(III), Abbreviation; [Ir(ppz)$_2$BIm]$_2$)

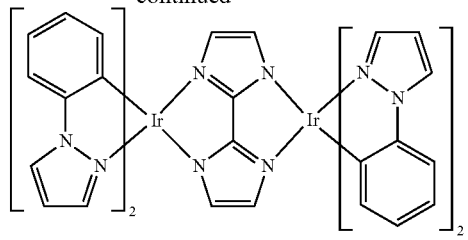

Under argon atmosphere, into a 100 mL Schlenk flask equipped with a stirrer were placed 308 mg (0.30 mmol) of di-μ-chloro-tetrakis(1-phenylpyrazolato)diiridium(III), 40 mg (0.30 mmol) of 2,2'-biimidazole and 60 ml of tetrahydrofuran. And then, the mixture was stirred at room temperature for 7 hours. Subsequently, 83 mg (0.63 mmol) of tert-butoxy potassium (t-BuOK (85 wt % product)) was added to the mixture, and the mixture was reacted under stirring at room temperature for 16 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride: 0.5% triethylamine) for purification, to provide 180 mg of the desired compound as a pale ocher solid. (Isolation yield: 55%)

Additionally, tetrakis(1-phenylpyrazolato)(μ-biimidazolyl) diiridium(III) was a novel compound, which had the following properties:

$^1$H-NMR (400 MHz, $CD_2Cl_2$, δ (ppm)); 8.35 (dd, 4H), 7.29 (dd, 4H), 6.76-6.80 (m, 8H), 6.61-6.56 (m, 4H), 6.50-6.48 (m, 4H), 6.39-6.39 (dd, 4H), 6.18 (s, 4H)

FD-MS (M/Z): 1088 M$^+$

Example 15

Synthesis of (tetrakis(2-(2,4-fluorophenyl)pyrazolato)(μ-biimidazolyl)diiridium(III), Abbreviation; [Ir(dfppz)$_2$BIm]$_2$)

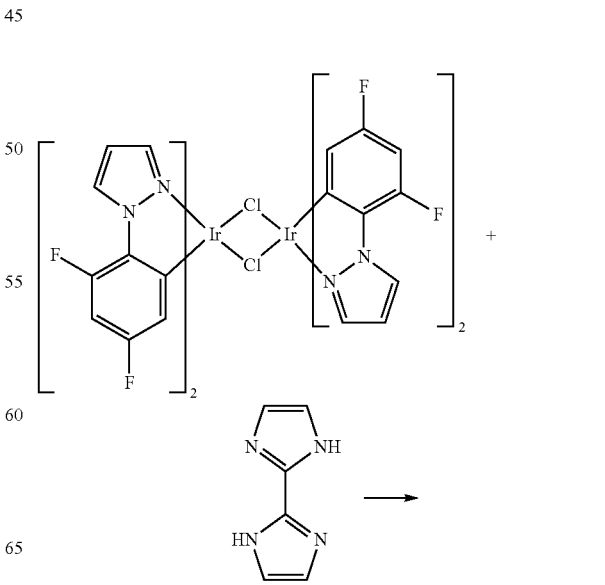

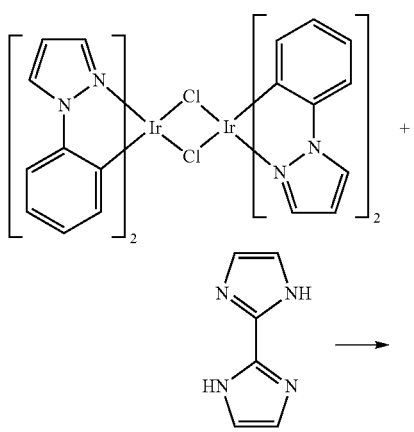

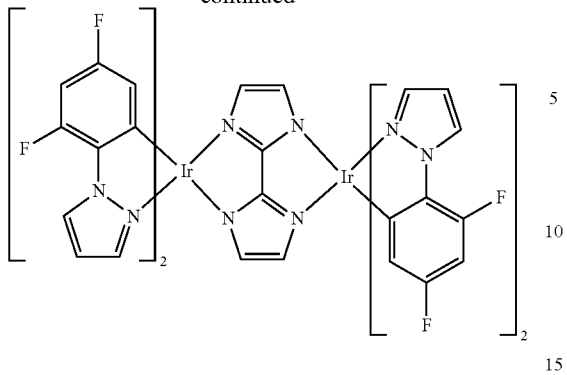

Under argon atmosphere, into a 100 mL Schlenk flask equipped with a stirrer were placed 234 mg (0.20 mmol) of di-μ-chloro-tetrakis(2-(2,4-fluorophenyl)pyrazolato)diiridium(III), 27 mg (0.20 mmol) of 2,2'-biimidazole and 40 ml of tetrahydrofuran. And then, the mixture was stirred at room temperature for 16 hours. Subsequently, 55 mg (0.42 mmol) of tert-butoxy potassium (t-BuOK (85 wt % product)) was added to the mixture, and the mixture was reacted under stirring at room temperature for 10 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride: 0.5% triethylamine) for purification, to provide 155 mg of the desired compound as a pale yellow solid. (Yield: 63%)

The desired compound obtained was a mixture of isomers, and the product ratio was Isomer 1 (main product): Isomer 2=60:40.

Additionally, tetrakis(2-(2,4-fluorophenyl)pyrazolato)(μ-biimidazolyl)diiridium(III) was a novel compound, which had the following properties:

$^1$H-NMR (400 MHz, $C_4D_8O$, δ (ppm))

Isomer 1; 8.38 (d, 4H), 7.24 (d, 4H), 6.65-6.57 (m, 8H), 6.26 (s, 4H), 5.87 (dd, 4H)

Isomer 2; 8.45 (d, 4H), 6.85 (d, 4H), 6.65-6.57 (m, 8H), 6.29 (s, 4H), 5.83 (dd, 4H)

FD-MS (M/Z): 1232 M$^+$

Example 16

Synthesis of (tetrakis(2-phenylpyridinato)(μ-biimidazolyl)diiridium(III), Abbreviation; [Ir(ppy)$_2$BIm]$_2$)

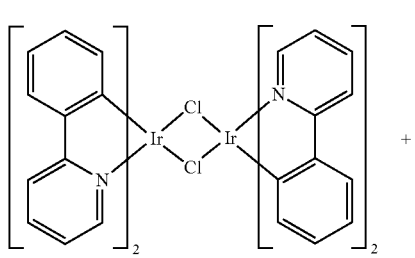

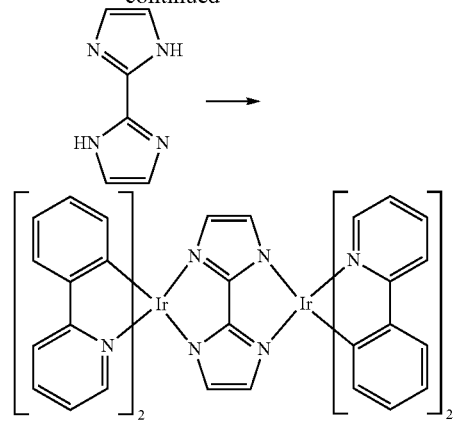

Under argon atmosphere, into a 100 mL Schlenk flask equipped with a stirrer were placed 322 mg (0.30 mmol) of di-μ-chloro-tetrakis(2-phenylpyridinato)diiridium(III), 40 mg (0.30 mmol) of 2,2'-biimidazole and 60 ml of tetrahydrofuran. And then, the mixture was stirred at room temperature for 13 hours. Subsequently, 83 mg (0.63 mmol) of tert-butoxy potassium (t-BuOK (85 wt % product)) was added to the mixture, and the mixture was reacted under stirring at room temperature for 24 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride/hexane (volume ratio; 3/1): 0.5% triethylamine) for purification, to provide 113 mg of the desired compound as a yellow solid. (Yield: 33%)

The desired compound obtained was a mixture of isomers, and the product ratio was Isomer 1 (main product): Isomer 2=61:39.

Additionally, tetrakis(2-phenylpyridinato)(μ-biimidazolyl)diiridium(III) was a novel compound, which had the following properties:

$^1$H-NMR (400 MHz, $C_4D_8O$, δ (ppm))

Isomer 1; 8.18 (dd, 4H), 7.86 (d, 4H), 7.70-7.55 (m, 8H), 6.81-6.72 (m, 8H), 6.66-6.62 (m, 4H), 6.38 (dd, 4H), 6.11 (s, 4H)

Isomer 2; 7.92 (d, 4H), 7.78 (dd, 4H), 7.70-7.55 (m, 8H), 6.81-6.72 (m, 8H), 6.66-6.62 (m, 4H), 6.32 (dd, 4H), 6.13 (s, 4H)

FD-MS (M/Z): 1132 M$^+$

Example 17

Synthesis of (tetrakis(3-methyl-1-phenylimidazoline-2-ylidene)(μ-biimidazolyl)diiridium(III), Abbreviation; [Ir(mpi)$_2$BIm]$_2$)

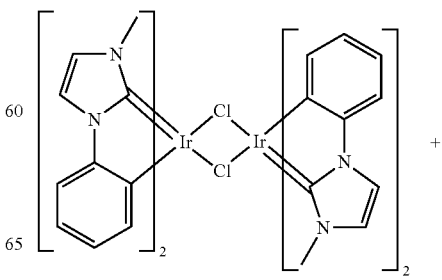

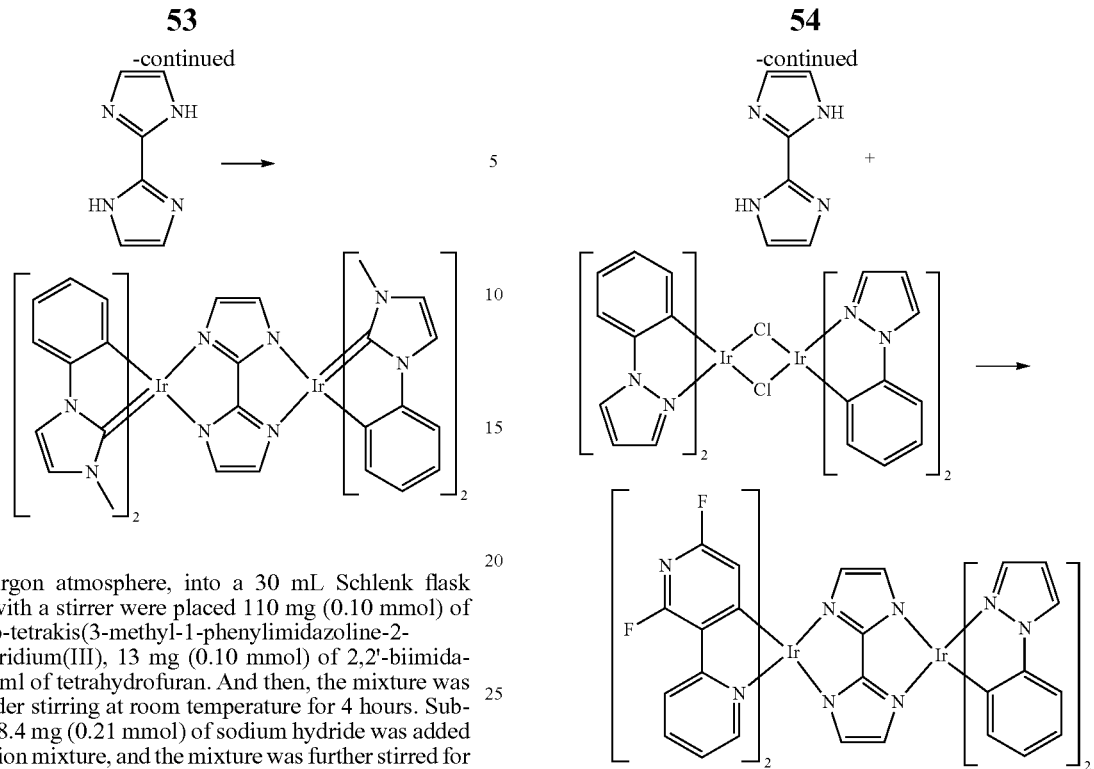

Under argon atmosphere, into a 30 mL Schlenk flask equipped with a stirrer were placed 110 mg (0.10 mmol) of di-μ-chloro-tetrakis(3-methyl-1-phenylimidazoline-2-ylidene)diiridium(III), 13 mg (0.10 mmol) of 2,2'-biimidazole and 2 ml of tetrahydrofuran. And then, the mixture was reacted under stirring at room temperature for 4 hours. Subsequently, 8.4 mg (0.21 mmol) of sodium hydride was added to the reaction mixture, and the mixture was further stirred for 19 hours. After the completion of the reaction, the solvent was distilled off under reduced pressure, and the reaction mixture was concentrated until the solvent content became about 3 ml. Subsequently, 20 ml of diethyl ether was added to the resultant mixture. And then, the precipitate was collected by filtration, and dried under reduced pressure, to provide 92.6 mg of tetrakis(1-methyl-3-phenylimidazoline-2-ylidene)(μ-biimidazolyl)diiridium as a brownish white solid. (Yield: 81%)

The desired compound obtained was a mixture of isomers, and the product ratio was Isomer 1 (main product): Isomer 2=53:43.

Additionally, tetrakis(1-methyl-3-phenylimidazoline-2-ylidene)(μ-biimidazolyl)diiridium had the following properties:

$^1$H-NMR (400 MHz, CD$_2$Cl$_2$, δ (ppm));

Isomer 1: 7.45 (d, 4H), 7.04 (dd, 4H), 6.93 (d, 4H), 6.80 (dt, 4H), 6.62-6.44 (m, 8H), 6.15 (s, 4H), 3.03 (s, 12H)

Isomer 2: 7.43 (d, 4H), 7.03 (dd, 4H), 6.91 (d, 4H), 6.79 (dt, 4H), 6.62-6.44 (m, 8H), 6.14 (s, 4H), 3.41 (s, 12H)

Example 18

Synthesis of (bis(1-phenylpyrazolato)bis(2',6'-difluoro-2,3'-bipyridinato)(μ-biimidazolyl)diiridium (III), Abbreviation; [Ir(ppz)(dfpypy)BIm]$_2$)

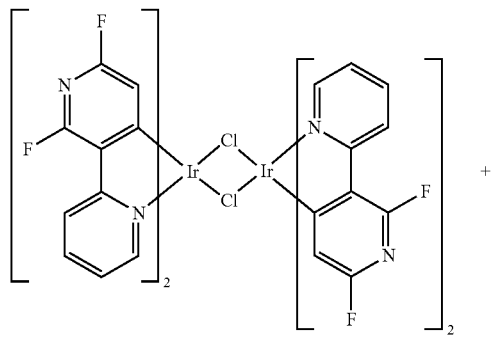

Under argon atmosphere, into a 30 mL Schlenk flask equipped with a stirrer were placed 61 mg (0.05 mmol) of di-μ-chloro-tetrakis(2',6'-difluoro-2,3'-bipyridinato)diiridium(III), 13 mg (0.10 mmol) of 2,2'-biimidazole and 10 ml of tetrahydrofuran. And then, the mixture was stirred at room temperature for 3 hours. Subsequently, 28 mg (0.21 mmol) of tert-butoxy potassium (t-BuOK (85 wt % product)) was added to the mixture, and the mixture was reacted under stirring at room temperature for 4 hours. And then, 51 mg (0.05 mmol) of di-μ-chloro-tetrakis(1-phenylpyrazolato)diiridium(III) was added to the mixture, and the mixture was reacted under stirring at room temperature for 14 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride/hexane (volume ratio; 2/1)) for purification, to provide 15 mg of the desired compound as a pale yellow solid. (Yield: 13%)

The desired compound obtained was a mixture of isomers, and the product ratio was Isomer 1 (main product): Isomer 2=88:12.

Additionally, bis(1-phenylpyrazolato)bis(2',6'-difluoro-2,3'-bipyridinato)(μ-biimidazolyl)diiridium(III) was a novel compound, which had the following properties:

$^1$H-NMR (400 MHz, CD$_2$Cl$_2$, δ (ppm))

Isomer 1; 8.24 (dd, 2H), 8.09 (dd, 2H), 7.86-7.82 (m, 2H), 7.74-7.72 (m, 2H), 7.23 (dd, 2H), 7.00-6.96 (m, 2H), 6.94-6.90 (m, 2H), 6.76 (dd, 2H), 6.74-6.70 (m, 2H), 6.47-6.46 (m, 2H), 6.37 (dd, 2H), 6.33 (d, 2H), 6.28 (d, 2H), 5.81 (m, 2H)

Isomer 2; 8.19 (dd, 2H), 8.08 (m, 2H), 8.03 (dd, 2H), 7.80 (dd, 2H), 7.22-7.11 (m, 6H), 6.93-6.88 (m, 6.74-6.70 (m, 2H), 6.53-6.52 (m, 2H), 6.42 (dd, 2H), 6.32 (d, 2H), 6.28 (d, 2H), 5.85 (m, 2H)

FD-MS (M/Z): 1184 M$^+$

Example 19

Synthesis of (tetrakis(2',6'-difluoro-2,3'-bipyridinato)(μ-bibenzimidazolyl)diiridium(III), Abbreviation; [Ir(dfpypy)₂BBIm]₂)

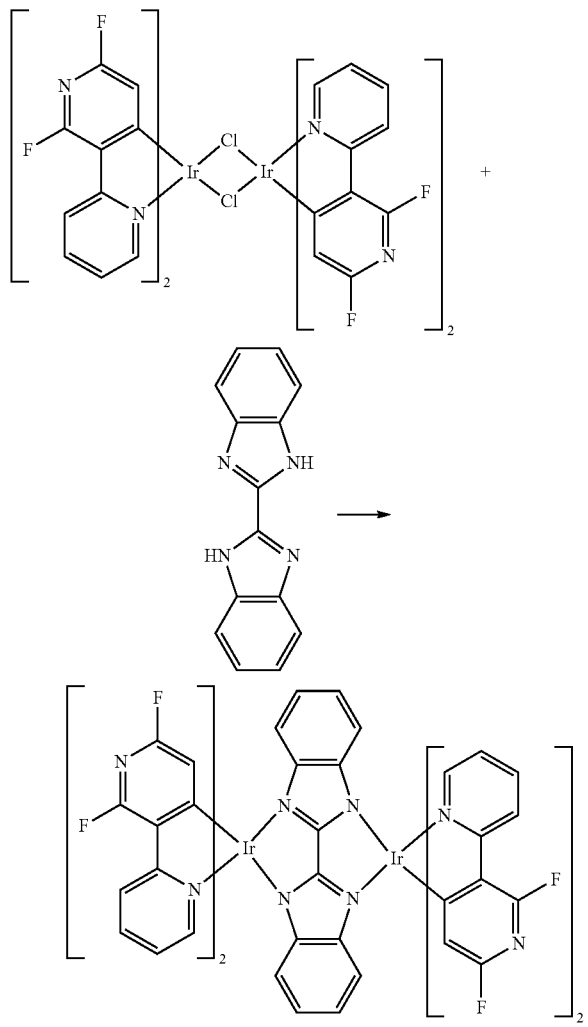

Under argon atmosphere, into a 50 mL Schlenk flask equipped with a stirrer were placed 122 mg (0.10 mmol) of di-μ-chloro-tetrakis(2',6'-difluoro-2,3'-bipyridinato)diiridium(III), 23 mg (0.10 mmol) of 2,2'-bibenzimidazole and 20 ml of tetrahydrofuran. And then, the mixture was stirred at room temperature for 7 hours. Subsequently, 28 mg (0.21 mmol) of tert-butoxy potassium (t-BuOK (85 wt % product)) was added to the mixture, and the mixture was reacted under stirring at room temperature for 16 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride) for purification, to provide 22 mg of the desired compound as a pale yellow solid. (Yield: 16%)

Additionally, tetrakis(2',6'-difluoro-2,3'-bipyridinato)(μ-bibenzimidazolyl)diiridium(III) was a novel compound, which had the following properties:

$^1$H-NMR (400 MHz, CD$_2$Cl$_2$, δ (ppm)); 8.27 (d, 4H), 7.84-7.79 (m, 4H), 7.72-7.70 (m, 4H), 6.85-6.81 (m, 8H), 6.38-6.35 (m, 4H), 5.97-5.96 (m, 4H)

FD-MS (MIZ): 1380 M⁺

Example 20

Synthesis of (tetrakis(2-(2,4-fluorophenyl)pyrazolato)(μ-bibenzimidazolyl)diiridium(III), Abbreviation; [Ir(dfppz)₂BBIm]₂)

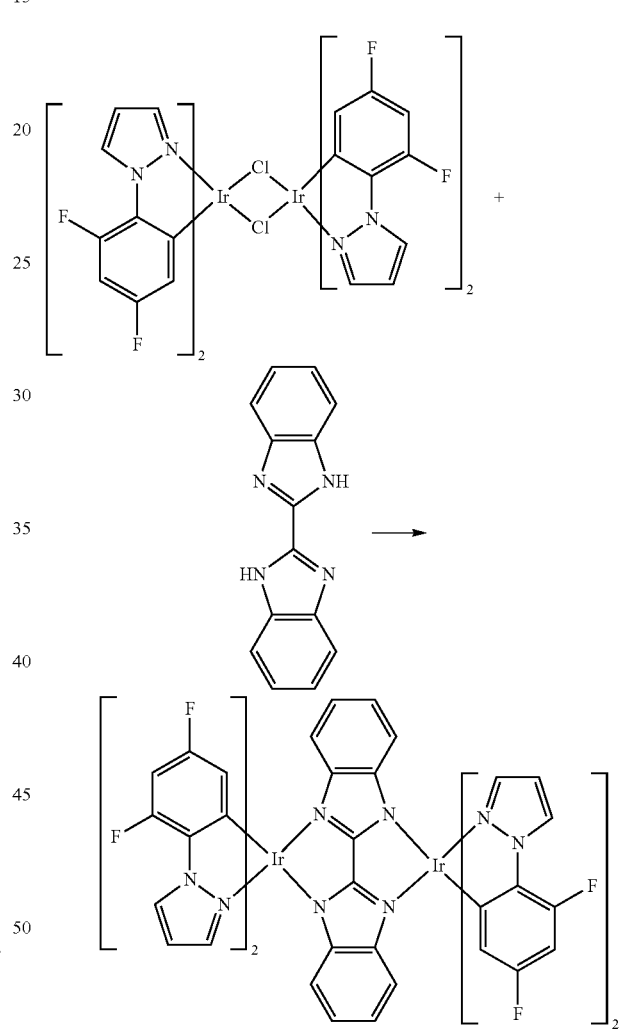

Under argon atmosphere, into a 100 mL Schlenk flask equipped with a stirrer were placed 293 mg (0.25 mmol) of di-μ-chloro-tetrakis(2-(2-(2,4-fluorophenyl)pyrazolato)diiridium(III), 59 mg (0.25 mmol) of 2,2'-bibenzimidazole and 50 ml of tetrahydrofuran. And then, the mixture was stirred at room temperature for 5 hours. Subsequently, 69 mg (0.53 mmol) of tert-butoxy potassium (t-BuOK (85 wt % product)) was added to the mixture, and the mixture was reacted under stirring at room temperature for 16 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride/hexane (volume ratio; 2/1)) for purification, to provide 236 mg of the desired compound as a pale yellow solid. (Yield: 71%)

The desired compound obtained was a mixture of isomers, and the product ratio was Isomer 1 (main product): Isomer 2=57:43.

Additionally, tetrakis(2-(2,4-fluorophenyl)pyrazolato)(μ-bibenzimidazolyl)diiridium(III) was a novel compound, which had the following properties:

$^1$H-NMR (400 MHz, $C_4D_8O$, δ (ppm))

Isomer 1; 8.45 (d, 4H), 6.84 (d, 4H), 6.81-6.70 (m, 8H), 6.55-6.53 (m, 4H), 6.36-6.31 (m, 4H), 6.03-6.00 (dd,4H)

Isomer 2; 8.39 (d, 4H), 7.22 (d, 4H), 6.81-6.70 (m, 8H), 6.55-6.53 (m, 4H), 6.36-6.31 (m, 4H), 6.08-6.05 (dd, 4H)

FD-MS (MO: 1332 M$^+$

Example 21

Synthesis of (bis(2',6'-difluoro-2,3'-bipyridinato)bis(2-(2,4-fluorophenyl)pyrazolato)(μ-bibenzimidazolyl)diiridium(III), Abbreviation; [Ir(dfpypy)(dfppz)BBIm]$_2$)

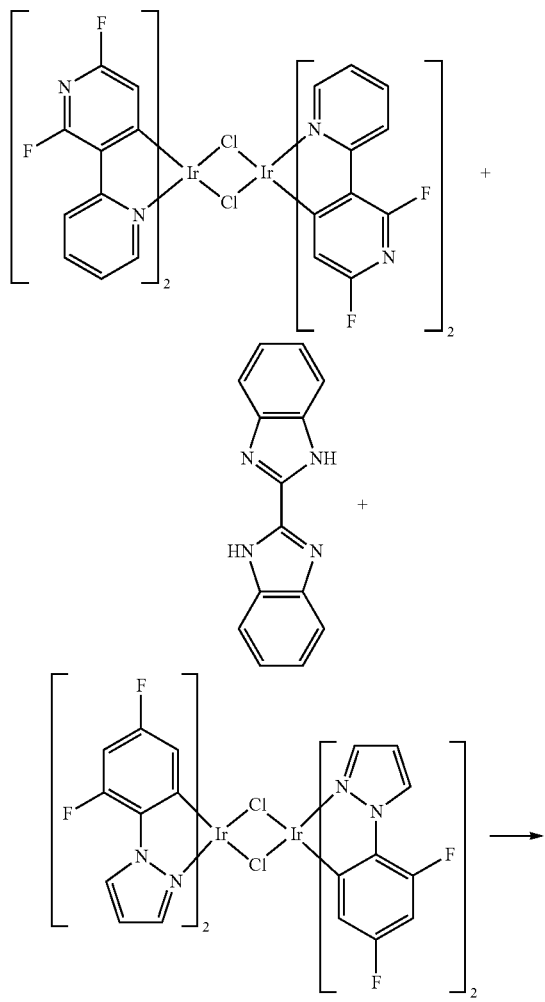

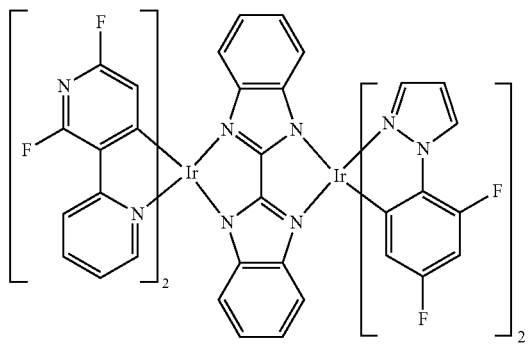

Under argon atmosphere, into a 50 mL Schlenk flask equipped with a stirrer were placed 122 mg (0.10 mmol) of di-μ-chloro-tetrakis(2',6'-difluoro-2,3'-bipyridinato)diiridium(III), 47 mg (0.20 mmol) of 2,2'-bibenzimidazole and 20 ml of tetrahydrofuran. And then, the mixture was stirred at room temperature for 1 hour. Subsequently, 55 mg (0.42 mmol) of tert-butoxy potassium (t-BuOK (85 wt% product)) was added to the mixture, and the mixture was reacted under stirring at room temperature for 12 hours. And then, 117 mg (0.10 mmol) of di-μ-chloro-tetrakis(2-(2,4-fluorophenyl)pyrazolato)diiridium(III) was added to the mixture, and the mixture was reacted under stirring at room temperature for 5 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride) for purification, to provide 180 mg of the desired compound as a yellow solid. (Yield: 66%)

The desired compound obtained was a mixture of isomers, and the product ratio was Isomer 1 (main product): Isomer 2=63:37.

Additionally, bis(2',6'-difluoro-2,3'-bipyridinato)bis(2-(2,4-fluorophenyl)pyrazolato)(μ-bibenzimidazolyl)diiridium(III) was a novel compound, which had the following properties:

$^1$H-NMR (400 MHz, $CD_2Cl_2$, δ (ppm))

Isomer 1; 8.33 (d, 2H), 8.27-8.25 (m, 2H), 7.80-7.73 (m, 4H), 6.90-6.87 (m, 2H), 6.83-6.80 (m, 4H), 6.75 (d, 2H), 6.70-6.67 (m, 2H), 6.43-6.41 (m, 2H), 6.38-6.33 (m, 4H), 6.06-6.03 (m, 2H), 6.00-5.99 (m, 2H)

Isomer 2; 8.26 (d, 2H), 8.20-8.21 (m, 2H), 8.00-7.98 (m, 2H), 7.80-7.78 (m, 2H), 7.05 (d, 2H), 7.04-7.00 (m, 2H), 6.83-6.80 (m, 4H), 6.70-6.67 (m, 2H), 6.47-6.46 (m, 2H), 6.38-6.33 (m, 4H), 6.10-6.08 (m, 2H), 6.04-6.02 (m, 2H)

FD-MS (M/Z): 1356 M$^+$

Example 22

Synthesis of (bis(2',6'-difluoro-2,3'-bipyridinato)bis(3-methyl-1-(3,5-difluorophenyl)imidazoline-2-ylidene)(μ-bibenzimidazolyl)diiridium(III), Abbreviation; [Ir(dfpypy)(dfmpi)BBIm]$_2$)

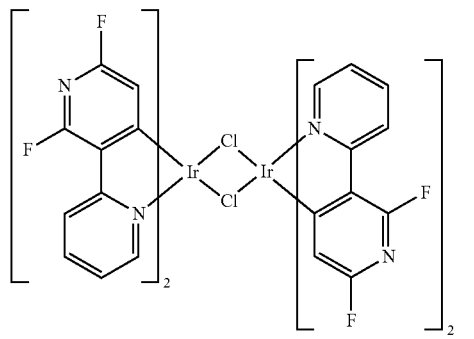

+

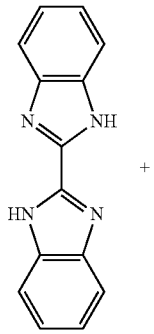

+

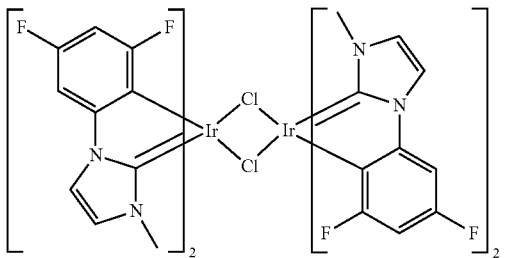

→

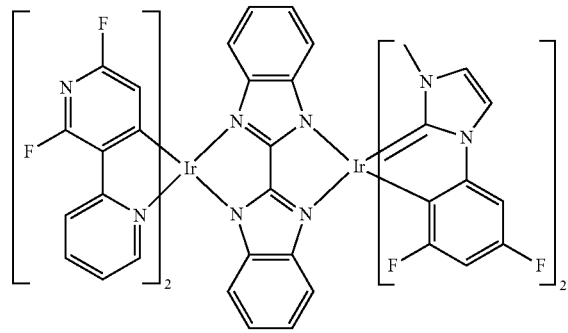

Under argon atmosphere, into a 50 mL Schlenk flask equipped with a stirrer were placed 92 mg (0.08 mmol) of di-μ-chloro-tetrakis(2',6'-difluoro-2,3'-bipyridinato)diiridium(III), 35 mg (0.15 mmol) of 2,2'-bibenzimidazole and 10 ml of tetrahydrofuran. And then, the mixture was stirred at room temperature for 1 hour. Subsequently, 42 mg (0.32 mmol) of tert-butoxy potassium (t-BuOK (85 wt % product)) was added to the mixture, and the mixture was reacted under stirring at room temperature for 16 hours. And then, 106 mg (0.08 mmol) of di-μ-chloro-tetrakis(3-methyl-1-(3,5-difluorophenyl)imidazoline-2-ylidene)diiridium(III) was added to the mixture, and the mixture was reacted under stirring at room temperature for 24 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride) for purification, to provide 89 mg of the desired compound as a yellow solid. (Yield: 43%)

The desired compound obtained was a mixture of isomers, and the product ratio was Isomer 1 (main product): Isomer 2=51:49.

Additionally, bis(2',6'-difluoro-2,3'-bipyridinato)bis(3-methyl-1-(3,5-difluorophenyl)imidazoline-2-ylidene)(μ-bibenzimidazolyl)diiridium(III) was a novel compound, which had the following properties:

$^1$H-NMR (400 MHz, CD$_2$Cl$_2$, δ (ppm))

Isomer 1; 8.26-8.24 (m, 2H), 7.86-7.79 (m, 4H), 7.36 (d, 2H), 6.98-6.96 (m, 2H), 6.88-6.85 (m, 2H), 6.82-6.77 (m, 4H), 6.74-6.73 (m, 2H), 6.34-6.28 (m, 4H), 6.20-6.16 (m, 2H), 6.02-6.01 (m, 2H), 2.50 (s, 6H)

Isomer 2; 8.26-8.24 (m, 2H), 8.02-8.00 (m, 2H), 7.83-7.79 (m, 2H), 7.29 (d, 2H), 7.00-6.97 (m, 2H ), 6.88-6.85 (m, 2H), 6.82-6.77 (m, 4H), 6.74-6.73 (m, 2H), 6.34-6.28 (m, 4H), 6.20-6.16 (m, 2H), 5.98-5.97 (m, 2H), 3.04 (s, 6H)

FD-MS (M/Z): 1384 M$^+$

Example 23

Synthesis of (tetrakis(2-(2,4-difluorophenyl)pyridinato)(μ-dimethyloxamidato)diiridium(III), Abbreviation; [Ir(dfppy)$_2$DMO]$_2$)

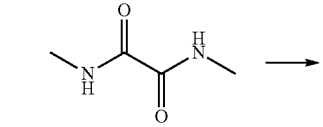

+

-continued

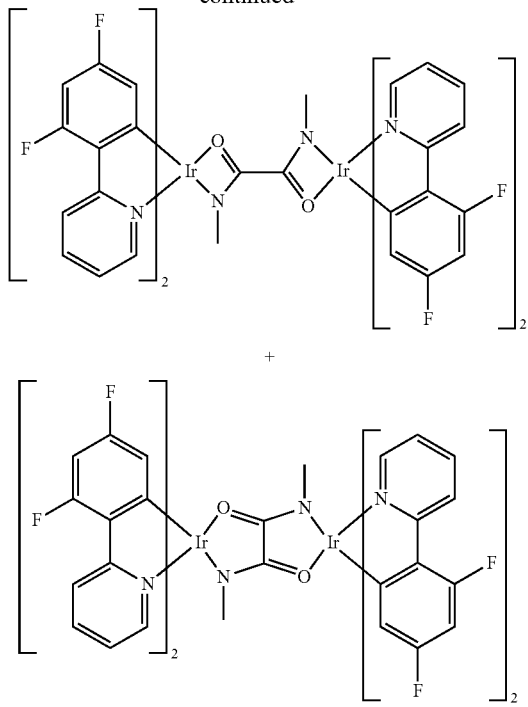

Under argon atmosphere, into a 50 mL Schlenk flask equipped with a stirrer were placed 122 mg (0.10 mmol) of di-μ-chloro-tetrakis(2-(2,4-difluorophenyl)pyridinato)diiridium(III), 12 mg (0.10 mmol) of N,N'-dimethyloxamide and 20 ml of tetrahydrofuran. And then, the mixture was stirred at room temperature for 1 hour. Subsequently, 28 mg (0.21 mmol) of tert-butoxy potassium (t-BuOK (85 wt % product)) was added to the mixture, and the mixture was reacted under stirring at room temperature for 3 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride/hexane (volume ratio; 2/1)) for purification, to provide 59 mg of the desired compound as a yellow solid. (Yield: 47%)

The desired compound obtained was a mixture of at least four different types of isomers, and the product ratio was estimated to be Isomer 1 (main product): Isomer 2: Isomer 3: Isomer 4=30:29:28:13.

Additionally, tetrakis(2-(2,4-difluorophenyl)pyridinato)(μ-dimethyloxamidato)diiridium(III) was a novel compound, which had the following properties:

$^1$H-NMR (400 MHz, CD$_2$Cl$_2$, δ (ppm))

Isomer 1; 8.70-8.04 (m, 8H), 7.89-7.80 (m, 4H), 7.35-7.06 (m, 4H), 6.41-6.34 (m, 4H), 5.72-5.58 (m, 4H), 2.52 (s, 6H)

Isomer 2; 8.70-8.04 (m, 8H), 7.89-7.80 (m, 4H), 7.35-7.06 (m, 4H), 6.41-6.34 (m, 4H), 5.72-5.58 (m, 4H), 2.53 (s, 6H)

Isomer 3; 810-8.04 (m, 8H), 7.89-7.80 (m, 4H), 7.35-7.06 (m, 4H), 6.41-6.34 (m, 4H), 5.72-5.58 (m, 4H), 2.56 (s, 6H)

Isomer 4; 8.70-8.04 (m, 8H), 7.89-7.80 (m, 4H), 7.35-7.06 (m, 4H), 6.41-6.34 (m, 4H), 5.72-5.58 (m, 4H), 2.54 (s, 6H)

FD-MS (M/Z): 1258 M$^+$

Example 24

Synthesis of (tetrakis(2',6'-difluoro-2,3'-bipyridinato)(μ-dimethyloxamidato)diiridium(III), Abbreviation; [Ir(dfpypy)$_2$DMO]$_2$)

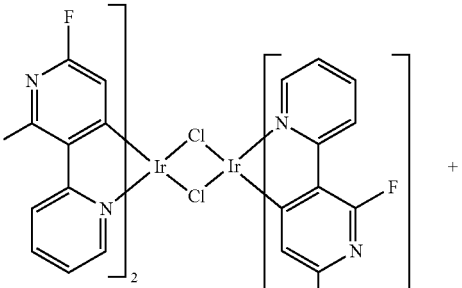

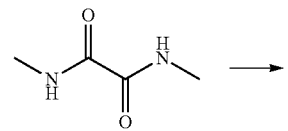

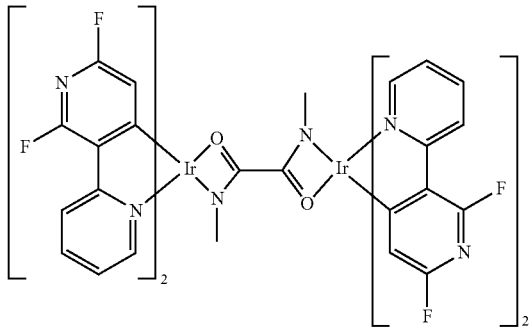

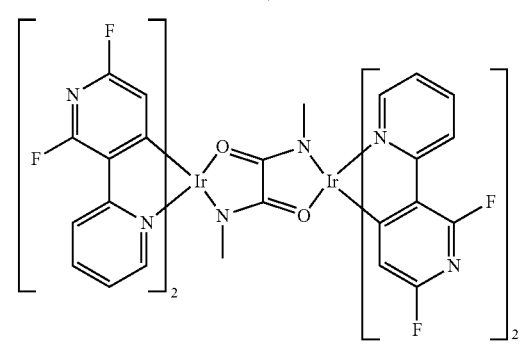

Under argon atmosphere, into a 50 mL Schlenk flask equipped with a stirrer were placed 122 mg (0.10 mmol) of di-μ-chloro-tetrakis(2',6'-difluoro-2,3'-bipyridinato)diiridium(III), 12 mg (0.10 mmol) of N,N'-dimethyloxamide, 28 mg (0.21 mmol) of tert-butoxy potassium (t-BuOK (85 wt % product)) and 20 ml of tetrahydrofuran. And then, the mixture was reacted under stirring at room temperature for 20 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was washed with methanol, and then recrystallized (solvent: acetone/diethyl ether (volume ratio; 1/2)) for purification, to provide 65 mg of the desired compound as a yellow solid. (Yield: 52%)

The desired compound obtained was a mixture of at least three different types of isomers, and the product ratio was estimated to be Isomer 1 (main product): Isomer 2: Isomer 3=33:27:20.

Additionally, tetrakis(2-(2,4-difluorophenyl)pyridinato) (μ-dimethyloxamidato)diiridium(III) was a novel compound, which had the following properties:

$^1$H-NMR (400 MHz, CD$_2$Cl$_2$, δ (ppm))
N—Me group of Isomer 1; 2.58 (s, 6H)
N—Me group of Isomer 2; 2.59 (s, 6H)
N—Me group of Isomer 3; 2.56 (s, 6H)
FD-MS (MO: 1262 M$^+$ Example 25

Synthesis of (tetrakis(1-phenylpyrazolato)(μ-1,4-benzoquinonato-2,5-diolato)diiridium(III), Abbreviation; [Ir(ppz)$_2$BQ]$_2$)

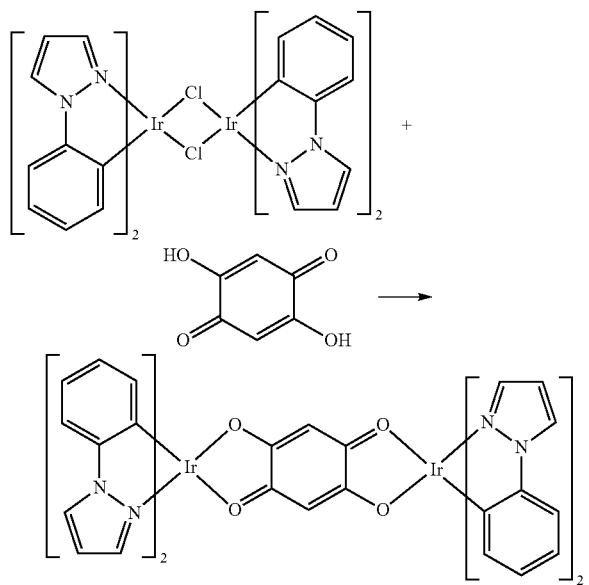

Under argon atmosphere, into a 30 mL Schlenk flask equipped with a stirrer were placed 150 mg (0.15 mmol) of di-μ-chloro-tetrakis(1-phenylpyrazolato)diiridium(III), 21 mg (0.15 mmol) of benzoquinone, 10 ml of toluene and 0.8 ml (0.30 mmol) of potassium hexamethyldisilazide (0.5M toluene solution). And then, the mixture was reacted under stirring at 100° C. for 29 hours. After the completion of the reaction, the solvent was distilled off under reduced pressure. Subsequently, 30 ml of dichloromethane was added to the residue, and then the resultant mixture was filtered. The filtrate was concentrated and dried under reduced pressure, to provide 129.7 mg of tetrakis(1-phenylpyrazolato)(μ-1,4-benzoquinonato-2,5-diolato)diiridium(III) as a brown solid. (79%)

Additionally, tetrakis(1-phenylpyrazolato)(μ-1,4-benzoquinonato-2,5-diolato)diiridium(III) had the following properties:

$^1$H-NMR (400 MHz, d-DMF, δ (ppm)); 8.93 (d, 4H), 7.67 (d, 4H), 7.63 (d, 4H), 6.89 (t, 4H), 6.86 (t, 4H), 6.64 (t, 4H), 6.13 (d, 4H), 5.70 (s, 2H)

FD-MS (M/Z): 1096 M$^+$

Example 26

Synthesis of (tetrakis(1-phenylpyrazolato)(2,5-pyrazinedicarboxylate)diiridium(III), Abbreviation; [Ir(ppz)$_2$25PDC]$_2$)

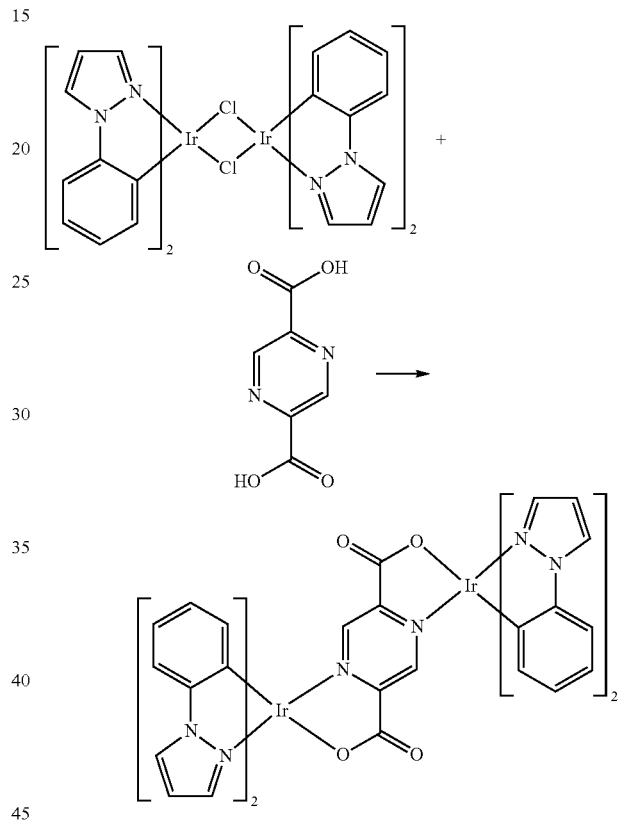

Under argon atmosphere, into a 30 mL Schlenk flask equipped with a stirrer were placed 150 mg (0.15 mmol) of di-μ-chloro-tetrakis(1-phenylpyrazolato)diiridium(III), 25 mg (0.15 mmol) of 2,5-pyrazinedicarboxylic acid, 16.2 mg (0.30 mmol) of sodium methoxide and 20 ml of methanol. And then, the mixture was reacted under stirring at room temperature for 4 hours. Subsequently, the precipitate was collected by filtration, and washed with diethyl ether and methanol, and then dried under reduced pressure, to provide 59.9 mg of tetrakis(1-phenylpyrazolato)(2,5-pyrazinedicarboxylate)diiridium(III) as a dark green solid. (36%)

Additionally, tetrakis(1-phenylpyrazolato)(2,5-pyrazinedicarboxylate)diiridium(III) had the following properties:

$^1$H-NMR (400 MHz, CD$_3$CN, δ (ppm)); 8.40 (s, 2H), 8.36 (d, 2H), 8.32 (d, 2H), 7.52 (d, 2H), 7.41 (d, 2H), 7.40 (td, 4H), 7.01 (td, 2H), 6.93 (td, 2H), 6.81 (td, 2H), 6.72 (td, 2H), 6.68 (t, 2H), 6.63 (t, 2H), 6.35 (dd, 2H), 6.04 (dd, 2H)

FD-MS (M/Z): 1124 M$^+$

Example 27

Synthesis of (tetrakis(1-phenylpyrazolato)(2,3-pyrazinedicarboxylate)diiridium(III), Abbreviation; [Ir(ppz)$_2$23PDC]$_2$)

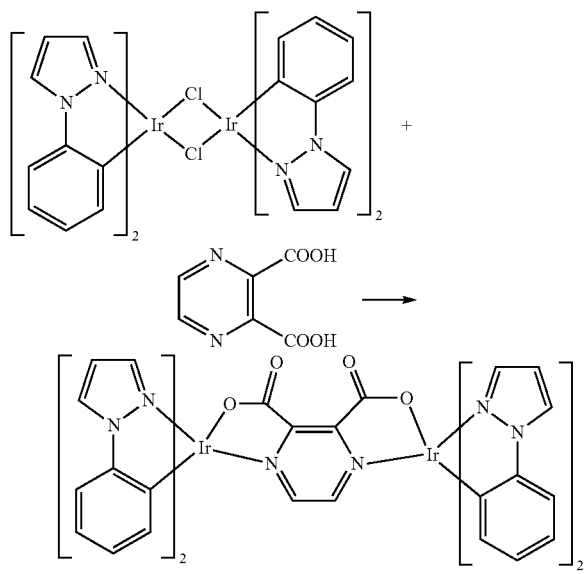

Under argon atmosphere, into a 30 mL Schlenk flask equipped with a stirrer were placed 150 mg (0.15 mmol) of di-μ-chloro-tetrakis(1-phenylpyrazolato)diiridium(III), 25 mg (0.15 mmol) of 2,3-pyrazinedicarboxylic acid, 16 mg (0.30 mmol) of sodium methoxide and 20 ml of methanol. And then, the mixture was reacted under stirring at room temperature for 24 hours. Subsequently, the precipitate was collected by filtration, and washed with methanol, and then dried under reduced pressure, to provide 97.3 mg of tetrakis(1-phenylpyrazolato)(2,3-pyrazinedicarboxylate)diiridium(III) as a dark brown solid. (58%)

Additionally, tetrakis(1-phenylpyrazolato)(2,3-pyrazinedicarboxylate)diiridium(III) had the following properties:

$^1$H-NMR (400 MHz, CD$_3$CN, δ (ppm)); 8.94 (d, 2H), 8.87 (d, 2H), 8.03 (s, 2H), 7.84 (d, 2H), 7.66 (d, 2H), 7.62 (d, 2H), 7.24 (d, 2H), 6.95-6.85 (m, 6H), 6.74-6.62 (m, 6H), 6.18 (dd, 2H), 6.09 (dd, 2H)

FD-MS (M/Z): 1080 (M−44)

Example 28

Synthesis of (tetrakis(1-phenylpyrazolato)(imidazole-2-carboxylate)diiridium(III), Abbreviation; [Ir(ppz)$_2$IC]$_2$)

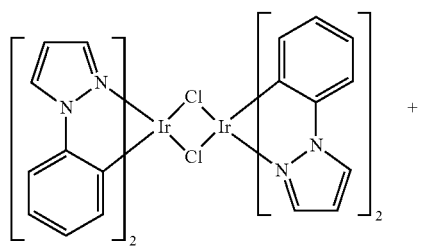

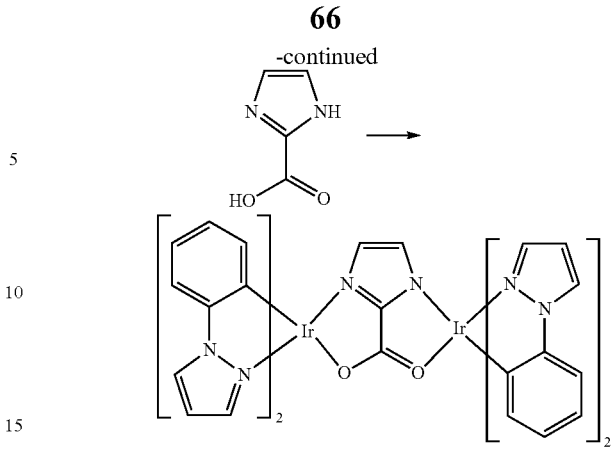

Under argon atmosphere, into a 50 mL two-necked eggplant flask equipped with a stirrer were placed 150 mg (0.15 mmol) of di-μ-chloro-tetrakis(1-phenylpyrazolato)diiridium(III), 17 mg (0.15 mmol) of imidazole-2-carboxylic acid, 30 ml of toluene and 0.6 ml (0.30 mmol) of potassium hexamethyldisilazide (0.5 M toluene solution). And then, the mixture was reacted under stirring at 100° C. for 24 hours. After the completion of the reaction, the solvent was distilled off under reduced pressure. Subsequently, 30 ml of dichloromethane was added to the residue, and then the resultant mixture was filtered. The filtrate was concentrated, and then the resultant concentrate was washed with diethyl ether. And then, the resultant reaction product was subjected to column chromatography with silica gel (developing solvent: methylene chloride-methanol (30:1)) for purification, to provide 68 mg of tetrakis(1-phenylpyrazolato)(imidazole-2-carboxylate)diiridium(III) as a white solid. (42%)

Additionally, tetrakis(1-phenylpyrazolato)(imidazole-2-carboxylate) diiridium(III) had the following properties:

$^1$H-NMR (400 MHz, d-DMF, δ (ppm)); 8.92 (t, 2H), 8.83 (d, 2H), 7.69-7.63 (m, 6H), 7.32 (d, 1H), 6.93-6.72 (m, 9H), 6.68-6.58 (m, 4H), 6.46 (d, 2H), 6.34-6.20 (m, 4H)

FD-MS (M/Z): 1068 M$^+$

Example 29

Production of Organic EL Element Comprising the Iridium Complex of the Present Invention An organic EL element was produced in the same way as in Example 5, except that the binuclear iridium complex [Ir(dfpypy)$_2$BIm]$_2$ (prepared in the same way as in Example 13)=95:5 was used instead of the binuclear iridium complex (1) used for the luminescent layer 4 in Example 5.

The layer construction of the element was briefly described as follows.

Anode 2: ITO (130 nm),
Hole-transport layer 3: 3DTAPBP (60 nm),
Luminescent layer 4: TPSiF: binuclear iridium complex [Ir(dfpypy)$_2$BIm]$_2$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +13 V and emitted light with a luminance of 510.8 cd/m$^2$ at +27 V. The current efficiency was 1.02 cd/A at +19 V.

In addition, the chromaticity coordinate, which was determined in accordance with JIS Z8701 from the spectrum measured at +23 V of the voltage between the electrodes, was x=0.128 and y=0.183 (by CIE (Commission Internationale de l'Eclairage) colorimetric system).

Example 30

Production of Organic EL Element Comprising the Iridium Complex of the Present Invention An organic EL element was produced in the same way as in Example 5, except that the binuclear iridium complex [Ir(dfpypy)$_2$BBIm]$_2$ (prepared in the same way as in Example 19)=95:5 was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF: binuclear iridium complex [Ir(dfpypy)$_2$BBIm]$_2$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +10 V and emitted light with a luminance of 1212 cd/m$^2$ at +26 V. The current efficiency was 1.71 cd/A at +17 V.

In addition, the chromaticity coordinate, which was determined in accordance with JIS Z8701 from the spectrum measured at +20 V of the voltage between the electrodes, was x=0.131 and y=0.222 (by CIE (Commission Internationale de l'Eclairage) colorimetric system).

Example 31

Production of Organic EL Element Comprising the Iridium Complex of the Present Invention An organic EL element was produced in the same way as in Example 5, except that the binuclear iridium complex [Ir(dfpypy)(dfppz)BBIm]$_2$ (prepared in the same way as in Example 21)=95:5 was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF: binuclear iridium complex [Ir(dfpypy)(dfppz)BBIm]$_2$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +11 V and emitted light with a luminance of 429.7 cd/m$^2$ at +26 V. The current efficiency was 0.81 cd/A at +19 V.

In addition, the chromaticity coordinate, which was determined in accordance with JIS Z8701 from the spectrum measured at +22 V of the voltage between the electrodes, was x=0.126 and y=0.182 (by CIE (Commission Internationale de l'Eclairage) colorimetric system).

Example 32

Production of Organic EL Element Comprising the Iridium Complex of the Present Invention An organic EL element was produced in the same way as in Example 5, except that the binuclear iridium complex [Ir(dfppy)$_2$DMO]$_2$ (prepared in the same way as in Example 23)=95:5 was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF: binuclear iridium complex [Ir(dfppy)$_2$DMO]$_2$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +8 V and emitted light with a luminance of 3173 cd/m$^2$ at +24 V. The current efficiency was 5.33 cd/A at +17 V.

In addition, the chromaticity coordinate, which was determined in accordance with JIS Z8701 from the spectrum measured at +20 V of the voltage between the electrodes, was x=0.203 and y=0.494 (by CIE (Commission Internationale de l'Eclairage) colorimetric system).

Reference Example 9

Production of Organic EL Element Comprising a Well-Known Iridium Complex

An organic EL element was produced in the same way as in Example 5, except that a well-known iridium complex, tris(2',6'-difluoro-2,3'-bipyridinato)iridium(III) (Abbreviation; Ir(dfpypy)$_3$) was used instead of the binuclear iridium complex used for the luminescent layer in Example 5.

The layer construction of the element was briefly described as follows.
Anode 2: ITO (130 nm),
Hole-transport layer 3: 3DTAPBP (60 nm),
Luminescent layer 4: TPSiF Ir(dfppy)$_3$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit light-blue light, which was clearly visible to the naked eye, around +15 V and emitted light with a luminance of 142 cd/m$^2$ at +22 V. The current efficiency was 0.35 cd/A at +19 V.

In addition, the chromaticity coordinate, which was determined in accordance with JIS Z8701 from the spectrum measured at +20 V of the voltage between the electrodes, was x=0.142 and y=0.134 (by CIE (Commission Internationale de l'Eclairage) colorimetric system).

Example 33

Production of Organic EL Element Comprising the Iridium Complex of the Present Invention An element was produced in the same way as in Example 5, except that the binuclear iridium complex [Ir(dfpypy)(dfmpi)BBIm]$_2$ (prepared in the same way as in Example 22) was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF: [Ir(dfpypy)(dfmpi)BBIm]$_2$ (40 nm, 95/5),
Electron-transport layer 5: TAZ (40 nm),
Electron-injection layer 6: LiF (0.5 nm),
Cathode 7: Al (100 nm).

The element was energized using the ITO electrode 2 as the anode and the Al electrode 7 as the cathode. When the voltage between the electrodes was increased, the element began to emit blue light, which was clearly visible to the naked eye, around +13 V and emitted light with a luminance of 569 cd/m$^2$ at +28 V. The current efficiency was 1.62 cd/A at +23 V.

In addition, the chromaticity coordinate, which was determined in accordance with JIS Z8701 from the spectrum measured at +23 V of the voltage between the electrodes, was x=0.130 and y=0.193 (by CIE (Commission Internationale de l+Eclairage) colorimetric system).

Example 34

Production of Organic EL Element Comprising the Iridium Complex of the Present Invention An element was produced in the same way as in Example 5, except that the binuclear iridium complex [Ir(dfpypy) 2DMO]$_2$ (prepared in the same way as in Example 24) was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF [Ir(dfpypy)$_2$DMO]$_2$ (40 nm, 95/5),
Electron-transport layer 5: TAZ (40 nm),
Electron-injection layer 6: LiF (0.5 am),
Cathode 7: Al (100 nm).

The element was energized using the ITO electrode 2 as the anode and the Al electrode 7 as the cathode. When the voltage between the electrodes was increased, the element began to emit blue light, which was clearly visible to the naked eye, around +12 V and emitted light with a luminance of 1705 cd/m$^2$ at +28 V. The current efficiency was 2.75 cd/A at +20 V.

In addition, the chromaticity coordinate, which was determined in accordance with JIS 28701 from the spectrum measured at +20 V of the voltage between the electrodes, was x=0.226 and y=0.211 (by CIE (Commission Internationale de l'Eclairage) colorimetric system).

Example 35

Production of Organic EL Element Comprising the Iridium Complex of the Present Invention An element was produced in the same way as in Example 5, except that the binuclear iridium complex [Ir(dfpypy)$_2$TMBBIm]$_2$ (prepared in the same way as in Example 38) was used instead of the binuclear iridium complex used for the luminescent layer 4 in Example 5.

The layer construction of the element was briefly described as follows.
Anode 2: ITO (130 nm),
Hole-transport layer 3: 3DTAPBP (60 nm),
Luminescent layer 4: TPSiF [Ir(dfpypy)$_2$TMBBIm]$_2$ (40 am, 95/5),
Electron-transport layer 5: TAZ (40 am),
Electron-injection layer 6: LiF (0.5 nm),
Cathode 7: Al (100 nm)

The element was energized using the ITO electrode 2 as the anode and the Al electrode 7 as the cathode. When the voltage between the electrodes was increased, the element began to emit blue light, which was clearly visible to the naked eye, around +13 V and emitted light with a luminance of 579 cd/m$^2$ at +29 V. The current efficiency was 1.66 cd/A at +18 V.

In addition, the chromaticity coordinate, which was determined in accordance with JIS Z8701 from the spectrum measured at +23 V of the voltage between the electrodes, was x=0.124 and y=0.181 (by CIE (Commission Internationale de l'Eclairage) colorimetric system).

Example 36

Synthesis of (tetrakis(2',6'-difluoro-4-methyl-2,3'-bipyridinato)(μ-bibenzimidazolyl)diiridium(III), Abbreviation; [Ir(dfpyMepy)$_2$BBIm]$_2$)

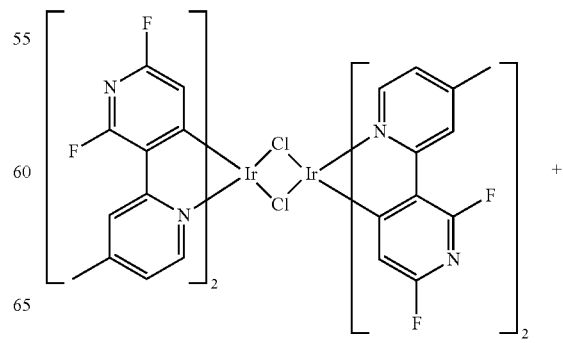

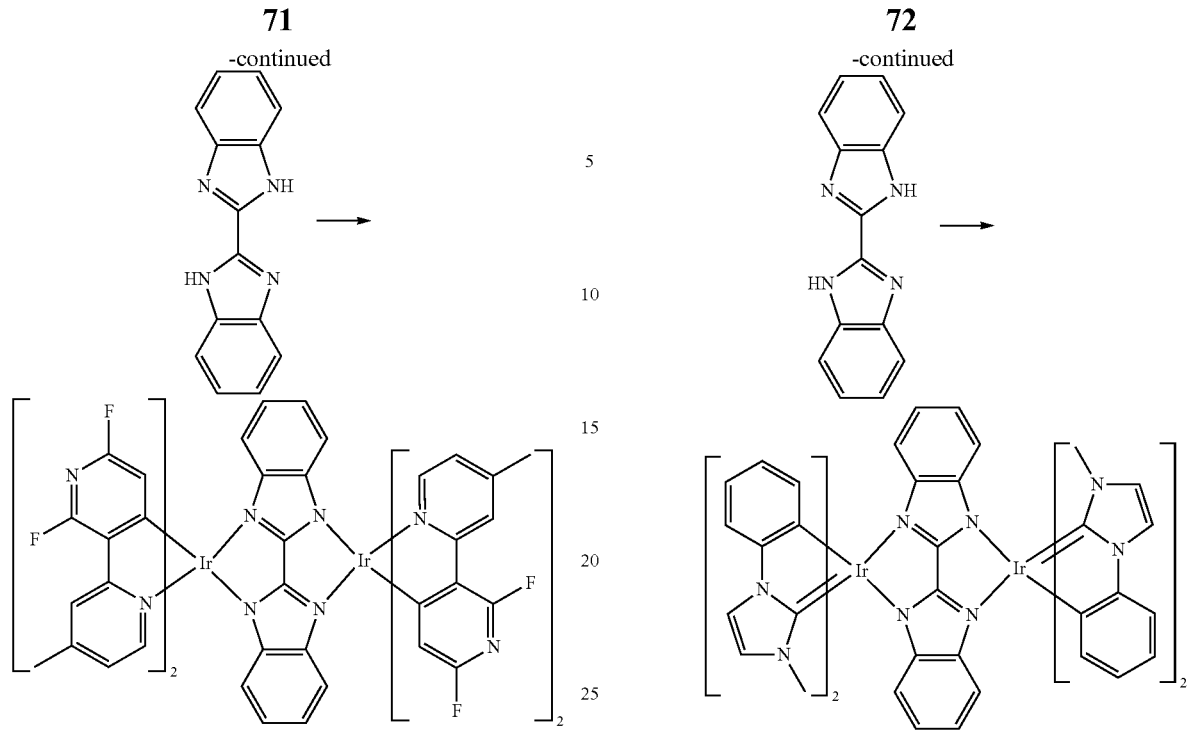

Under argon atmosphere, into a 50 mL Schlenk flask equipped with a stirrer were placed 191 mg (0.15 mmol) of di-μ-chloro-tetrakis(2',6'-difluoro-4-methyl-2,3'-bipyridinato)diiridium(III), 35 mg (0.15 mmol) of 2,2'-bibenzimidazole, 42 mg (0.32 mmol) of tert-butoxy potassium (t-BuOK (85 wt % product)) and 15 ml of tetrahydrofuran. And then, the mixture was reacted under stirring at room temperature for 17 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride) for purification, to provide 60 mg of the desired compound as a pale yellow solid. (Yield: 28%)

Additionally, tetrakis(2',6'-difluoro-4-methyl-2,3'-bipyridinato)(μ-bibenzimidazolyl)diiridium(III) was a novel compound, which had the following properties:

$^1$H-NMR (400 MHz, CD$_2$Cl$_2$, δ (ppm)); 8.08 (s, 4H), 7.52 (d, 4H), 6.84-6.80 (m, 4H), 6.63-6.61 (m, 4H), 6.37-6.33 (m, 4H), 5.99-5.98 (m, 4H), 2.53 (s, 12H)

FD-MS (M/Z): 1436, 1438

Example 37

Synthesis of (tetrakis(3-methyl-1-phenylimidazoline-2-ylidene)(μ-bibenzimidazolyl)diiridium(III), Abbreviation; [Ir(pmi)$_2$BBIm]$_2$)

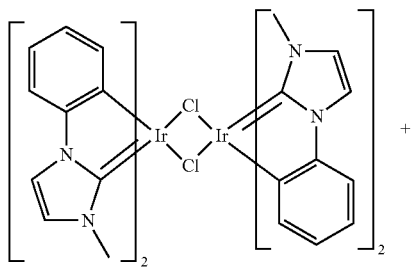

Under argon atmosphere, into a 100 mL Schlenk flask equipped with a stirrer were placed 108 mg (0.10 mmol) of (di-μ-chloro-tetrakis(3-methyl-1-phenylimidazoline-2-ylidene)diiridium(III), 23 mg (0.10 mmol) of 2,2'-bibenzimidazole, 28 mg (0.21 mmol) of tert-butoxy potassium (t-BuOK (85 wt % product)) and 10 ml of tetrahydrofuran. And then, the mixture was reacted under stirring at room temperature for 21 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride/hexane (volume ratio; 2/1)) for purification, to provide 102 mg of the desired compound as a pale yellow solid. (Yield: 82%)

The desired compound obtained was a mixture of isomers, and the product ratio was Isomer 1 (main product): Isomer 2=52:48.

Additionally, tetrakis(3-methyl-1-phenylimidazoline-2-ylidene)(μ-bibenzimidazolyl)diiridium(III) was a novel compound, which had the following properties:

$^1$H-NMR (400 MHz, CD$_2$Cl$_2$, δ (ppm))

Isomer 1; 7.95 (d, 4H), 7.35-7.32 (m, 4H), 7.23-7.21 (m, 4H), 6.89-6.84 (m, 4H), 6.65-6.51 (m, 12H), 5.94-5.90 (m, 4H), 2.77 (s, 12H)

Isomer 2; 7.97 (d, 4H), 7.35-7.32 (m, 4H), 7.23-7.21 (m, 4H), 6.89-6.84 (m, 4H), 6.65-6.51 (m, 12H), 5.94-5.90 (m, 4H), 3.14 (s, 12H)

FD-MS (M/Z): 1245, 1247

Example 38

Synthesis of (tetrakis(2',6'-difluoro-2,3'-bipyridinato)(μ-tetramethylbibenzoimidazolyl)diiridium(III), Abbreviation; [Ir(dfpypy)₂TMBBIm]₂)

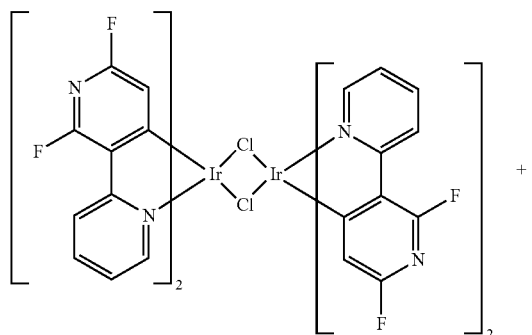

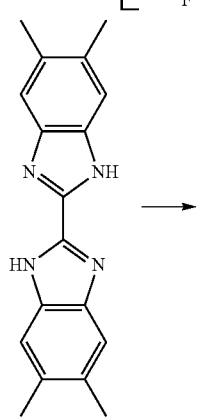

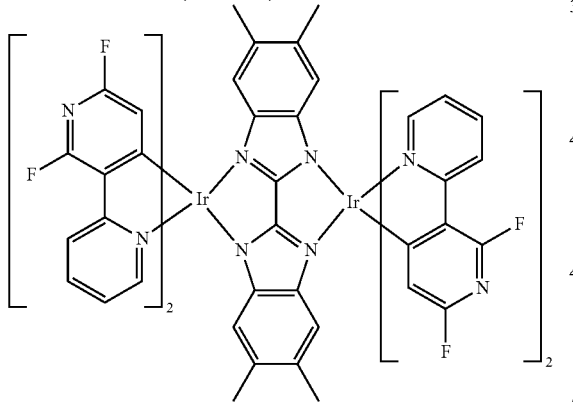

Under argon atmosphere, into a 50 mL Schlenk flask equipped with a stirrer were placed 122 mg (0.10 mmol) of di-μ-chloro-tetrakis(2',6'-difluoro-2,3'-bipyridinato) diiridium(III), 29 mg (0.10 mmol) of 5,5',6,6'-tetramethylbibenzoimidazole, 28 mg (0.21 mmol) of tert-butoxy potassium (t-BuOK (85 wt % product)) and 10 ml of tetrahydrofuran. And then, the mixture was reacted under stirring at room temperature for 15 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride) for purification, to provide 87 mg of the desired compound as a pale yellow solid. (Yield: 61%)

The desired compound obtained was a mixture of isomers, and the product ratio was Isomer 1 (main product): Isomer 2=60:40.

Additionally, tetrakis(2',6'-difluoro-2,3'-bipyridinato)(μ-tetramethylbibenzoimidazolyl)diiridium(III) was a novel compound, which had the following properties:

$^1$-NMR (400 MHz, CD$_2$Cl$_2$, δ (ppm))

Isomer 1; 8.27-8.25 (m, 4H), 7.82-7.78 (m, 4H), 7.70-7.69 (m, 4H), 6.82-6.79 (m, 4H), 6.07 (s, 4H), 5.98-5.97 (m, 4H), 2.02 (s, 12H)

Isomer 2; 8.21-8.19 (m, 4H), 7.99-7.98 (m, 4H), 7.77-7.73 (m, 4H), 7.01-6.98 (m, 4H), 6.06 (s, 4H), 6.02-6.01 (m, 4H), 2.03 (s, 12H)

FD-MS (M/Z): 1436 M⁺

Example 39

Synthesis of (tetrakis(3-methyl-1-phenylimidazoline-2-ylidene)(μ-dimethyloxamidato)diiridium(III), Abbreviation; [Ir(mpi)₂DMO]₂)

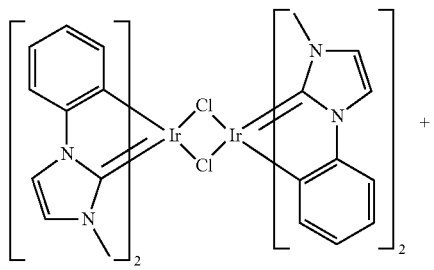

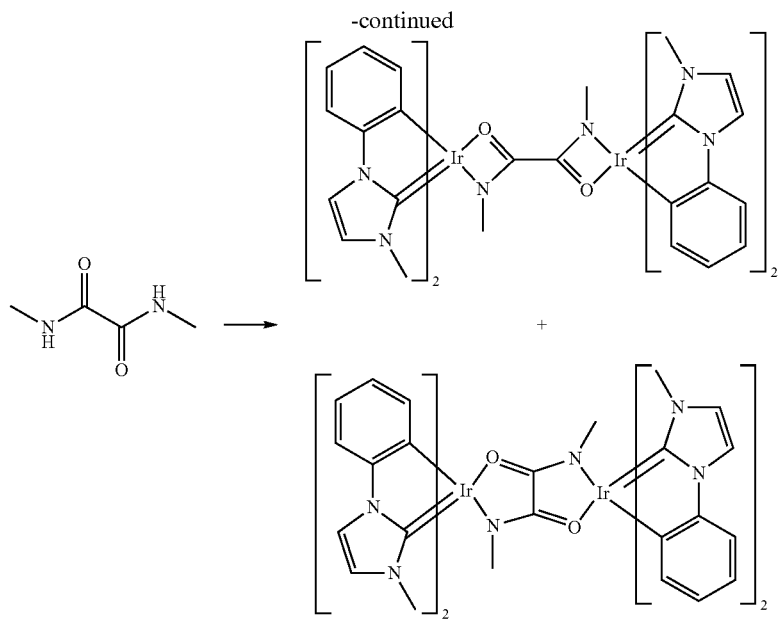

Under argon atmosphere, into a 50 mL Schlenk flask equipped with a stirrer were placed 217 mg (0.20 mmol) of di-μ-chloro-tetrakis(3-methyl-1-phenylimidazoline-2-ylidene)diiridium(III), 23 mg (0.20 mmol) of N,N'-dimethyloxamide, 55 mg (0.42 mmol) of tert-butoxy potassium (t-BuOK (85 wt % product)) and 20 ml of tetrahydrofuran. And then, the mixture was reacted under stirring at room temperature for 22 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with alumina (developing solvent: methylene chloride) for purification, to provide 113 mg of the desired compound as a pale yellow solid. (Yield: 50%)

The desired compound obtained was a mixture of four different types of isomers.

The desired compound obtained was a mixture of isomers, and the product ratio was Isomer 1 (main product): Isomer 2: Isomer 3: Isomer 4=55:36:5.4:3.6.

Additionally, tetrakis(3-methyl-1-phenylimidazoline-2-ylidene)(μ-dimethyloxamidato)diiridium(III) was a novel compound, which had the following properties:

$^1$H-NMR (400 MHz, $CD_2Cl_2$, δ (ppm))

Isomer 1; 7.50-7.44 (m, 4H), 7.09-6.97 (m, 8H), 6.76-6.73 (m, 4H), 651-6.49 (m, 4H), 6.47-6.13 (m, 4H), 3.96 (s, 6H), 3.82 (s, 6H), 2.47 (s, 6H)

Isomer 2; 7.50-7.44 (m, 4H), 7.09-6.97 (m, 8H), 6.76-6.73 (m, 4H), 6.51-6.49 (m, 4H), 6.47-6.13 (m, 4H), 3.75 (s, 6H), 3.56 (s, 6H), 2.48 (s, 6H)

Isomer 3; 7.50-7.44 (m, 4H), 7.09-6.97 (m, 8H), 6.76-6.73 (m, 4H), 6.51-6.49 (m, 4H), 6.47-6.13 (m, 4H), 3.92 (s, 6H), 3.88 (s, 6H), 2.48 (s, 6H)

Isomer 4; 7.50-7.44 (m, 4H), 7.09-6.97 (m, 8H), 6.76-6.73 (m, 4H), 6.51-6.49 (m, 4H), 6.47-6.13 (m, 4H), 3.82 (s, 6H), 3.66 (s, 6H), 2.49 (s, 6H)

FD-MS (M/Z): 1126 M$^+$

Example 40

Synthesis of (tetrakis(2,4-difluorophenylpyridinato)(μ-2,2'-bipyridinato-3,3'-diolato)diiridium(III), Abbreviation; [Ir(dfppy)$_2$bpo]$_2$)

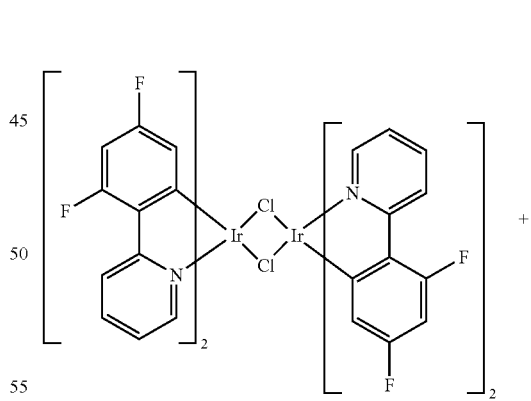

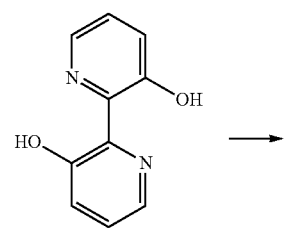

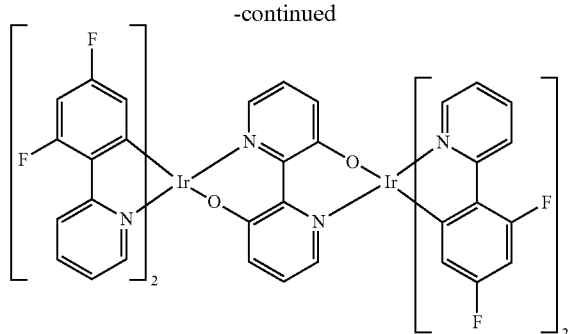

Under argon atmosphere, into a 50 mL Schlenk flask equipped with a stirrer were placed 122 mg (0.10 mmol) of (di-μ-chloro-tetrakis(2,4-difluorophenylpyridinato)diiridium(III), 19 mg (0.10 mmol) of 2,2'-bipyridine-3,3'-diol, 28 mg (0.21 mmol) of tert-butoxy potassium (t-BuOK (85 wt % product)) and 20 ml of tetrahydrofuran. And then, the mixture was reacted under stirring at room temperature for 3 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: methylene chloride/ethyl acetate (volume ratio; 10/1-10/2)) for purification, to provide 99 mg of the desired compound as a yellow solid. (Yield: 74%)

The desired compound obtained was a mixture of isomers, and the product ratio was Isomer 1 (main product): Isomer 2=47:27.

Additionally, tetrakis(2,4-difluorophenylpyridinato)(μ-2,2'-bipyridinato-3,3'-diolato)diiridium(III) was a novel compound, which had the following properties:

$^1$H-NMR (400 MHz, CD$_2$Cl$_2$, δ (ppm))

Isomer 1; 9.03 (d, 2H), 8.39 (d, 2H), 8.33 (d, 2H), 8.15 (d, 2H), 7.82 (dd, 2H), 7.64 (dd, 2H), 7.15 (dd, 2H), 6.91 (dd, 2H), 6.74-6.76 (m, 2H), 6.37-6.45 (m, 6H), 6.19-6.16 (m, 2H), 6.00-5.98 (m, 2H), 3.33-5.32 (m, 2H)

Isomer 2; 8.59 (d, 2H), 8.39 (d, 2H), 8.14 (d, 2H), 7.85 (dd, 2H), 7.61 (dd, 2H), 7.24 (d, 2H), 7.08-7.04 (m, 4H), 6.84 (dd, 2H), 6.58-6.54 (m, 2H), 6.47-6.35 (m, 6H), 5.76-5.73 (m, 2H), 5.54-5.49 (m, 2H)

FD-MS (M/Z):

Isomer 1; 1330, 1332

Isomer 2; 1330, 1332

Example 41

Synthesis of tetrakis(3-methyl-1-phenylimidazoline-2-ylidene)(μ-2,2'-bipyridinato-3,3'-diolato)diiridium (III), Abbreviation; [Ir(mpi)$_2$bpo]$_2$)

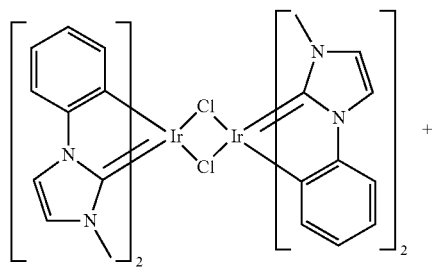

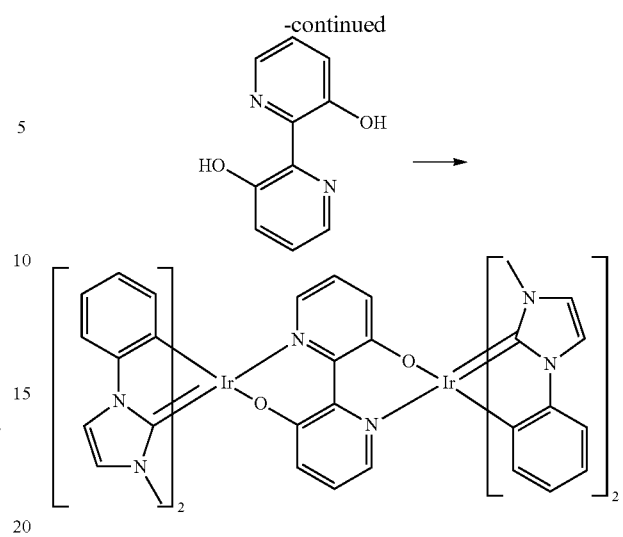

Under argon atmosphere, into a 50 mL Schlenk flask equipped with a stirrer were placed 108 mg (0.10 mmol) of di-μ-chloro-tetrakis(3-methyl-1-phenylimidazoline-2-ylidene)diiridium(III), 19 mg (0.10 mmol) of 2,2'-bipyridine-3,3-diol, 28 mg (0.21 mmol) of tert-butoxy potassium (t-BuOK (85 wt % product)) and 20 ml of tetrahydrofuran. And then, the mixture was reacted under stirring at room temperature for 18.5 hours. After the completion of the reaction, tetrahydrofuran was distilled off under reduced pressure, and then methylene chloride was added to the residue, and the insoluble substance was removed by filtration. The filtrate was concentrated under reduced pressure. The resultant crude reaction product was subjected to column chromatography with silica gel (developing solvent: ethyl acetate) for purification, to provide 64 mg of the desired compound as a yellow solid. (Yield: 55%)

Additionally, tetrakis(3-methyl-1-phenylimidazoline-2-ylidene)(μ-2,2'-bipyridinato-3,3'-diolato)diiridium(III) was a novel compound, which had the following properties:

$^1$H-NMR (400 MHz, CD$_2$Cl$_2$, δ (ppm)); 7.44 (d, 2H), 7.41 (d, 2H), 7.09-7.06 (m, 2H), 7.06-7.01 (d, 2H), 6.96-6.95 (m, 2H), 6.90 (d, 2H), 6.80-6.75 (m, 6H), 6.52-6.43 (m, 6H), 6.37-6.34 (m, 2H), 6.23-6.20 (m, 2H), 6.16-6.14 (m, 2H), 3.83 (s, 6H), 3.13 (s, 6H)

FD-MS (M/Z): 1198

Example 42

Synthesis of (tetrakis(2',6'-difluoro-2,3'-bipyridinato)(μ-2,5-pyrazinedicarboxylate)diiridium(III), Abbreviation; [Ir(dfpypy)$_2$25PDC]$_2$)

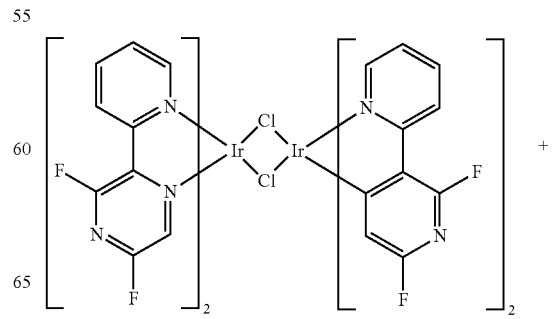

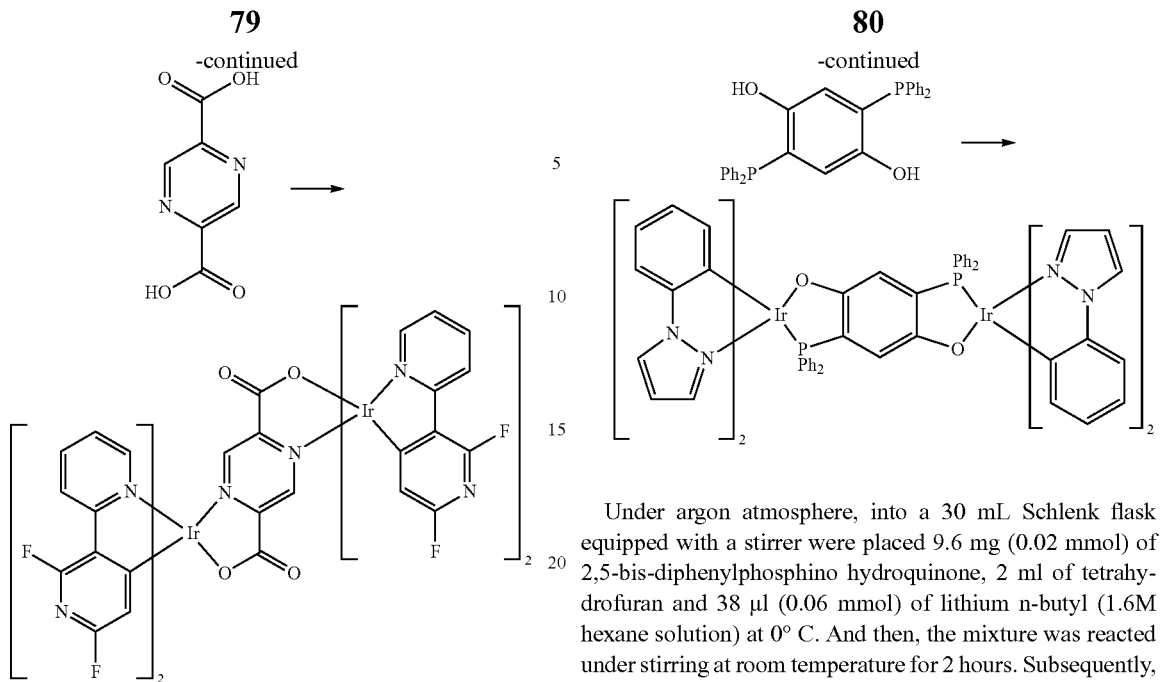

Under argon atmosphere, into a 30 mL Schlenk flask equipped with a stirrer were placed 31 mg (0.15 mmol) of 2,5-pyrazinedicarboxylic acid, 16 mg (0.30 mmol) of sodium methoxide and 20 ml of methanol. And then, the mixture was reacted under stirring at room temperature for 2 hours. After the solvent was distilled off under reduced pressure, 184 mg (0.15 mmol) of di-μ-chloro-tetrakis(2',6'-difluoro-2,3'-bipyridinato)diiridium(III) and 25 ml of 2-ethoxyethanol were added to the residue, and then the resultant mixture was reacted under stirring at 110° C. for 20 hours. After the completion of the reaction, the solvent was distilled off under reduced pressure. Subsequently, 30 ml of dichloromethane was added to the concentrate, and then the resultant mixture was filtered. The precipitate collected by filtration was washed with pure water, and then dried under reduced pressure, to provide 166 mg of tetrakis(2',6'-difluoro-2,3'-bipyridinato)(μ-2,5-pyrazinedicarboxylate)diiridium(III) as an orange solid. (84%)

Additionally, tetrakis(2',6'-difluoro-2,3'-bipyridinato)(μ-2,5-pyrazinedicarboxylate)diiridium(III) had the following properties:

$^1$H-NMR (400 MHz, d-DMF, δ (ppm)); 8.64 (d, 2H), 8.51 (s, 2H), 8.46-8.24 (m, 6H), 8.17 (dt, 2H), 7.92 (dd, 2H), 7.73 (ddd, 2H), 7.15 (ddd, 2H), 6.01 (s, 2H), 5.50 (s, 2H)

FD-MS (M/Z): 1316 M$^+$

Example 43

Synthesis of (tetrakis(1-phenylpyrazolato)(μ-2,5-bisdiphenylphosphino-1,4-benzoquinolato)diiridium (III), Abbreviation; [Ir(ppz)$_2$DPPHQ]2)

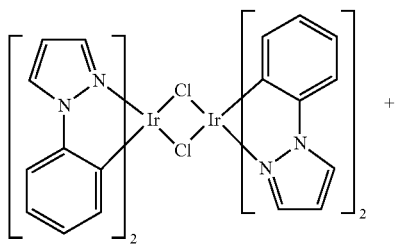

Under argon atmosphere, into a 30 mL Schlenk flask equipped with a stirrer were placed 9.6 mg (0.02 mmol) of 2,5-bis-diphenylphosphino hydroquinone, 2 ml of tetrahydrofuran and 38 μl (0.06 mmol) of lithium n-butyl (1.6M hexane solution) at 0° C. And then, the mixture was reacted under stirring at room temperature for 2 hours. Subsequently, 21 mg (0.02 mmol) of di-μ-chloro-tetrakis(1-phenylpyrazolato)diiridium(III) was added to the reaction mixture, and then the resultant mixture was reacted under stirring at 80° C. for 19 hours. After the completion of the reaction, the solvent was distilled off under reduced pressure. Subsequently, 30 ml of dichloromethane was added to the concentrate, and then the resultant mixture was filtered. The filtrate was concentrated under reduced pressure, and then dried, to provide 18.4 mg of tetrakis(1-phenylpyrazolato)(μ-2,5-bisdiphenylphosphino-1,4-benzoquinolato)diiridium(III) as a yellow solid. (64%)

Additionally, tetrakis(1-phenylpyrazolato)(μ-2,5-bisdiphenylphosphino-1,4-hydroquinolato)diiridium(III) had the following properties:

$^1$H-NMR (400 MHz, CD$_2$Cl$_2$, δ (ppm)); 8.03 (d, 2H), 7.79 (t, 4H), 7.67 (d, 2H), 7.44-6.62 (m, 36H), 6.30 (dt, 4H), 6.20 (t, 2H)

FD-MS (M/Z): 1434 M$^-$

Example 44

Synthesis of (tetrakis(1-phenylpyrazolato)(μ-4,10-diazachrysenolato)diiridium(III), Abbreviation; [Ir(ppz)$_2$DAC]$_2$)

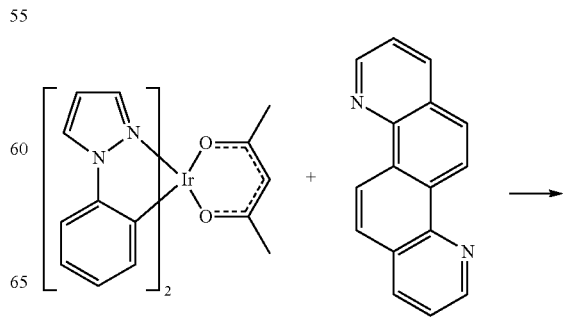

-continued

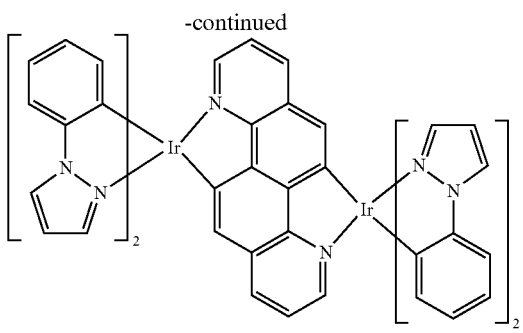

Under argon atmosphere, into a 30 mL Schlenk flask equipped with a stirrer were placed 45.8 mg (0.08 mmol) of bis(1-phenylpyrazolato)(acetylacetonato)iridium(III), 4.6 mg (0.02 mmol) of 4,10-diazachrysene and 6 ml of glycerin. And then, the mixture was reacted under stirring at 180° C. for 3 hours. After the completion of the reaction, 20 ml of ion-exchanged water was added to the reaction mixture, and then the resultant mixture was filtered. The precipitate collected by filtration was washed with diethyl ether, and then dried under reduced pressure, to provide 22.0 mg of black solid containing the desired compound.

FD-MS (M/Z): 1186 M+

Example 45

Synthesis of (bis(1-methyl-2-phenylimidazolato) (biimidazolyl)iridium(III) chloride)

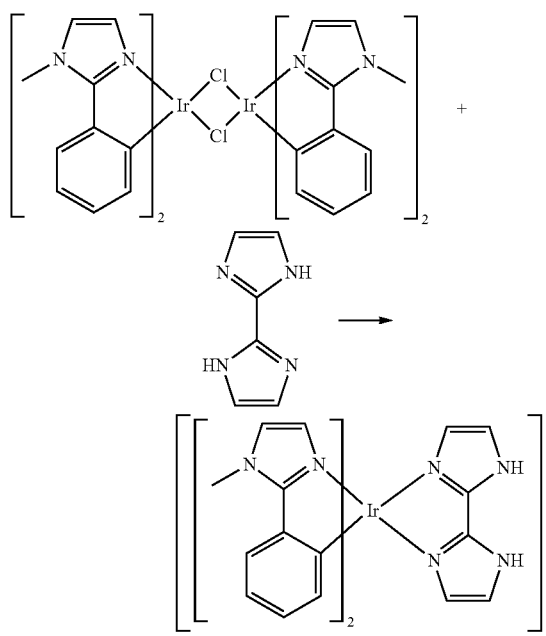

Under argon atmosphere, into a 50 mL Schlenk flask equipped with a stirrer were placed 109 mg (0.10 mmol) of di-μ-chloro-tetrakis(1-phenylpyrazolato)diiridium(III), 13 mg (0.10 mmol) 1 mg of 2,2'-biimidazole and 20 ml of tetrahydrofuran. And then, the mixture was reacted under stirring at room temperature for 5 hours, and at bath temperature of 50° C. for 11 hours. After the completion of the reaction, the reaction solution was filtered, and then the filtrate was concentrated under reduced pressure, to provide 25 mg of the desired compound as a brown solid. (Yield; 20%)

Additionally, bis(1-methyl-2-phenylimidazolato)(biimidazolyl)iridium(III) chloride was a novel compound, which had the following properties:

$^1$H-NMR (400 MHz, $CD_2Cl_2$, δ (ppm)); 14.1 (brs, 2H), 7.48 (dd, 2H), 7.08 (m, 2H), 6.92 (m, 2H), 6.83 (d, 2H), 6.78 (m, 2H), 6.60-6.52 (m, 4H), 6.30 (d, 2H), 4.05 (s, 6H)

FD-MS (M/Z): 640 (M-35)

Industrial Applicability

According to the present invention, there may be provided a binuclear metal complex, which is useful as a material for an organic electroluminescence element, for example, and an organic electroluminescence element comprising the same.

Description Of The Main Symbols 1. glass substrate
2. ITO transparent electrode
3. hole-transport layer
4. luminescent layer
5. electron-transport layer
6. electron-injection layer
7. aluminum electrode

The invention claimed is:

1. A binuclear metal complex represented by the formula (1):

$$(L^1)_m[M^1(L)_qM^2](L^2)_n \quad (1)$$

wherein the moiety represented by the formula: $[M^1(L)_qM^2]$ represents a structure represented by the formula (3):

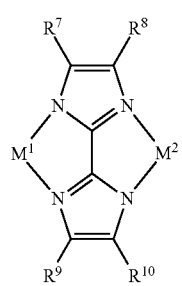

wherein $M^1$ and $M^2$ may be the same as, or different from each other, and each independently represents Ru, Os, Rh, Ir or Pd, and $R^7$, $R^8$, $R^9$ and $R^{10}$ may be the same as, or different from each other, and each independently represents a hydrogen atom or an alkyl group or a halogen atom; or a structure represented by the formula (4):

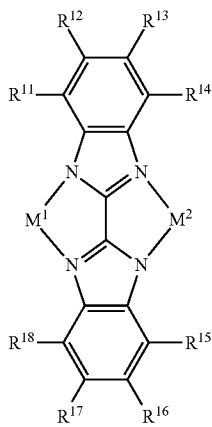

(4)

wherein
M¹ and M² may be the same as, or different from each other, and each independently represents Ru, Os, Rh, Ir or Pd, and
R¹¹, R¹², R¹³, R¹⁴, R¹⁵, R¹⁶, R¹⁷ and R¹⁸ may be the same as, or different from each other, and each independently represents a hydrogen atom or an alkyl group or a halogen atom;
L¹ represents a ligand coordinated to the metal atom M¹,
L² represents a ligand coordinated to the metal atom M², and
m and n represent the numbers of L¹ and L², respectively, and each independently represents an integer of 1 or greater, with the proviso that
in the cases where m is 2 or greater, two or more ligands L¹s may be the same as, or different from each other, and
in the cases where n is 2 or greater, two or more ligands L²s may be the same as, or different from each other, and
at least one of L¹s and/or at least one of L²s is a pyridylpyridine compound represented by formula (12):

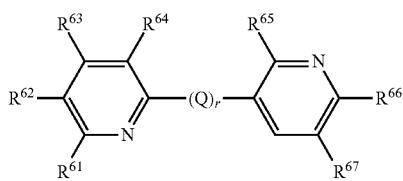

(12)

wherein
R⁶¹ to R⁶⁷ may be the same as, or different from each other, and each independently represents a hydrogen atom, or a linear or branched alkyl group having 1 to 10 carbon atoms, or a halogen atom,
Q represents methylene, and
r represents 0 or 1.

2. The binuclear metal complex as claimed in claim 1, wherein in the formula (1),
each of L¹s and L²s is a bidentate ligand, and
m and n are 2,
with the proviso that
L¹ and L² may be the same as, or different from each other,
two L¹s may be the same as, or different from each other, and
two L²s may be the same as, or different from each other.

3. The binuclear metal complex as claimed in claim 1, wherein in the formula (1),
each of M¹ and M² is Ir,
each of L¹s and L²s is any one of the bidentate ligands represented by formula (12), and
m and n are 2,
with the proviso that
L¹ and L² may be the same as, or different from each other,
two L¹s may be the same as, or different from each other, and
two L²s may be the same as, or different from each other.

4. The binuclear metal complex as claimed in claim 3, wherein
two L¹s are the same as each other, and
two L²s are the same as each other,
with the proviso that
L¹ and L² may be the same as, or different from each other.

5. An organic electroluminescence element, comprising a binuclear metal complex as claimed in claim 1.

* * * * *

UNITED STATES PATENT AND TRADEMARK OFFICE
CERTIFICATE OF CORRECTION

PATENT NO. : 9,029,541 B2
APPLICATION NO. : 13/990928
DATED : May 12, 2015
INVENTOR(S) : Osamu Fujimura et al.

Page 1 of 2

It is certified that error appears in the above-identified patent and that said Letters Patent is hereby corrected as shown below:

Specification
Col. 7, line 40, "$L^1$" should be --$L^1$s--.
Col. 9, line 19, "$R"^{119}$" should be --$R^{119}$--.
Col. 10, line 20, "It" should be --Ir.--.
Col. 10, line 34, "complexs," should be --complexes,--.
Col. 10, line 51, "complexs," should be --complexes,--.
Col. 13, line 6, "$R^{101}{}_{to}R^{106}$" should be --$R^{101}$ to $R^{106}$--.
Col. 21, line 14, "diethylamine," should be --diethylamino,--.
Col. 21, line 32, "he" should be --be--.
Col. 24, line 44, "morpholine," should be --morpholino,--.
Col. 30, line 18, "(µ-" should be --(p- --.
Col. 30, line 53, "polypara-phenylene" should be --poly-para-phenylene--.
Col. 36, line 11, "JIS 28701" should be --JIS Z8701--.
Col. 38, line 15, "(MIZ):" should be --(M/Z):--.
Col. 41, line 17, "ylidene) diiridium" should be --ylidene)diiridium--.
Col. 41, line 20, "2ylidene)" should be --2-ylidene)--.
Col. 43, line 46, "(m," should be --(m, 1H),--.
Col. 43, line 47, "(MO;" should be --(M/Z);--.
Col. 44, line 28, "(m, 11-1)," should be --(m, 1H),--.
Col. 44, line 29, "1H)" should be --1H),--.
Col. 44, line 64, "ylidene) diiridium" should be --ylidene)diiridium--.
Col. 45, line 14, "644" should be --6.44--.
Col. 46, line 60, "(m, in)," should be --(m, 1H),--.
Col. 49, line 42, below "4H)" insert --FD-MS (M/Z): 1280 $M^+$--.
Col. 54, line 64, "(m," should be --(m, 2H),--.
Col. 56, line 7, "(MIZ):" should be --(M/Z):--.
Col. 57, line 19, "(MO:" should be --(M/Z):--.
Col. 61, line 62, "810-8.04" should be --8.70-8.04--.
Col. 63, line 17, "(MO:" should be --(M/Z):--.

Signed and Sealed this
Fifteenth Day of March, 2016

Michelle K. Lee
*Director of the United States Patent and Trademark Office*

CERTIFICATE OF CORRECTION (continued)
U.S. Pat. No. 9,029,541 B2

Specification
Col. 67, line 2, "JIS 28701" should be --JIS Z8701--.
Col. 67, line 34, "JIS 28701" should be --JIS Z8701--.
Col. 67, line 66, "JIS 28701" should be --JIS Z8701--.
Col. 68, line 33, "JIS 28701" should be --JIS Z8701--.
Col. 68, line 66, "JIS 28701" should be --JIS Z8701--.
Col. 69, line 36, "1+Eclairage)" should be --l'Eclairage)--.
Col. 69, line 56, "am)," should be --nm),--.
Col. 69, line 66, "JIS 28701" should be --JIS Z8701--.
Col. 70, line 22, "am," should be --nm,--.
Col. 70, line 25, "am)," should be --nm),--.
Col. 70, line 27, "nm)" should be --nm).--.
Col. 74, line 31, "$^1$-NMR" should be --$^1$H-NMR--.
Col. 75, line 59, "651" should be --6.51--.
Col. 78, line 26, "3,3-diol," should be --3,3'-diol,--.

Col. 78, lines 56-67, " 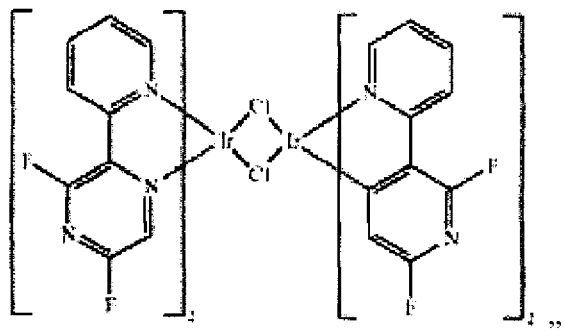 "

should be -- 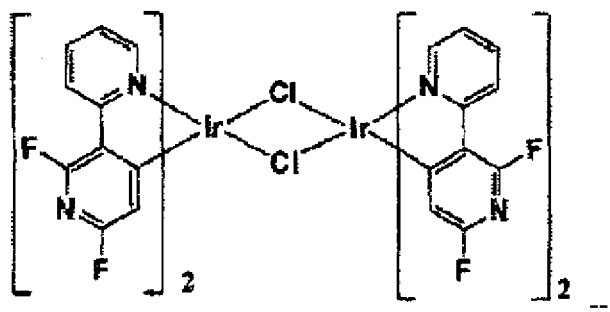 --.

Col. 79, line 45, "2,5 -pyrazinedicarboxylate)" should be --2,5-pyrazinedicarboxylate)--.
Col. 79, line 56, "Q]2)" should be --Q]$_2$)--.
Col. 80, line 45, "M"" should be --M$^+$--.